United States Patent
Rosenzweig et al.

(10) Patent No.: US 10,772,974 B2
(45) Date of Patent: Sep. 15, 2020

(54) COMPOSITIONS AND METHODS FOR CARDIAC REGENERATION

(71) Applicants: Beth Israel Deaconess Medical Center, Inc., Boston, MA (US); Children's Medical Center Corporation, Boston, MA (US)

(72) Inventors: Anthony Rosenzweig, Newton, MA (US); Vassilios J. Bezzerides, Brookline, MA (US)

(73) Assignees: Beth Israel Deaconess Medical Center, Inc., Boston, MA (US); Children's Medical Center Corporation, Boston, MA (US)

( * ) Notice: Subject to any disclaimer, the term of this patent is extended or adjusted under 35 U.S.C. 154(b) by 643 days.

(21) Appl. No.: 15/037,195

(22) PCT Filed: Nov. 18, 2014

(86) PCT No.: PCT/US2014/066037
§ 371 (c)(1),
(2) Date: May 17, 2016

(87) PCT Pub. No.: WO2015/074010
PCT Pub. Date: May 21, 2015

(65) Prior Publication Data
US 2016/0287724 A1 Oct. 6, 2016

Related U.S. Application Data

(60) Provisional application No. 61/905,515, filed on Nov. 18, 2013.

(51) Int. Cl.
*A61K 48/00* (2006.01)
*C07K 14/47* (2006.01)
*C12N 15/86* (2006.01)

(52) U.S. Cl.
CPC ........ *A61K 48/005* (2013.01); *A61K 48/0058* (2013.01); *A61K 48/0075* (2013.01); *C07K 14/47* (2013.01); *C12N 15/86* (2013.01); *C12N 2710/00041* (2013.01); *C12N 2710/10343* (2013.01); *C12N 2750/14143* (2013.01); *C12N 2830/006* (2013.01); *C12N 2830/008* (2013.01)

(58) Field of Classification Search
CPC .............. A61K 48/005; A61K 48/0075; A61K 48/0058; C12N 15/86; C12N 2830/008; C12N 2710/10343; C12N 2830/006; C12N 2710/00041; C12N 2750/14143; C07K 14/47
USPC ....... 514/44 R; 435/320.1; 424/199.1, 233.1; 530/350
See application file for complete search history.

(56) References Cited

FOREIGN PATENT DOCUMENTS

WO WO-2007/062827 A1 6/2007
WO WO 2007/062827 * 7/2007

OTHER PUBLICATIONS

Bostrom et al. (2010) Cell, vol. 143, 1072-1083.*
Wolfram et al. (2013) J. Am. Heart Assoc., vol. 2, e000119, DOI: 10.1161/JAHA.113.000119, pp. 1-11.*
Nagai et al. (2012) Am J. Heart Circ. Physiol., vol. 303, H501-H512.*
Wolfram et al. (2013) J Am Heart Assoc., vol. 2, e000119, pp. 1-11.*
Liu et al., "miR-222 Is Necessary for Exercise-Induced Cardiac Growth and Protects Against Pathological Cardiac Remodeling," Abstract 238, American Heart Association's Basic Cardiovascular Sciences 2014 Scientific Sessions: "Pathways to Cardiovascular Therapeutics," 2014; see also *Circulation Research*, 115(1)Suppl 1:229 (2014).
Boström et al., "C/EBPb Controls Exercise-Induced Cardiac Growth and Protects against Pathological Cardiac Remodeling," *Cell*, 143:1072-1083 (2010).
Caroli et al., "Potential therapeutic role of microRNAs in ischemic heart disease," *J. Cardiol.* 61:315-320 (2013).
Chistiakov et al., "Strategies to deliver microRNAs as potential therapeutics in the treatment of cardiovascular pathology," *Drug Deliv.*, 19(8):392-405 (2012).
Ding et al., "MicroRNAs in cardiac hypertrophy: angels or devils," *Wiley Interdisciplinary Reviews: RNA*, 2(1):124-134 (2010).
Felli et al., "MicroRNAs 221 and 222 inhibit normal erythropoiesis and erythroleukemic cell growth via kit receptor down-modulation," *Proc. Natl. Acad. Sci. USA*, 102(50):18081-18086 (2005).
Huang and Jia, "Construction of HCC-targeting artificial miRNAs using natural miRNA precursors," *Exper. Thera. Med.*, 6:209-215 (2013).
Liu et al., "Cell-specific effects of miR-221/222 in vessels: Molecular mechanism and therapeutic application," *J. Molec. Cell. Cardiol.*, 52:245-255 (2012).
Liu et al., "miR-222 Is Necessary for Exercise-Induced Cardiac Growth and Protects against Pathological Cardiac Remodeling," *Cell Metabolism*, 21:584-595 (2015).
Liu et al., EMBASE Caesar accession No. 1153, "MIR-222 is necessary for excercise-induced cardiac growth and protects against pathological cardiac remodeling," 4 pages (2015).
Ryall et al., "Phenotypic screen quantifying differential regulation of cardiac myocyte hypertrophy identifies CITED4 regulation of myocyte elongation," *J. Molec. Cell. Cardiol.*, 72:74-84 (2014).

(Continued)

*Primary Examiner* — Anne Marie S Wehbe
(74) *Attorney, Agent, or Firm* — McCarter & English, LLP

(57) ABSTRACT

The invention relates to the use of a CITED4 polypeptide and/or a microRNA-222 or precursor (e.g., pre-miR-222) or mimic thereof, for treating a cardiovascular disease or pathological condition, such as heart failure, myocardial infarction, and for promoting post-myocardial infarction cardiac remodeling in heart tissue.

20 Claims, 21 Drawing Sheets
Specification includes a Sequence Listing.

(56) References Cited

OTHER PUBLICATIONS

Wszolek et al., "A MicroRNA expression profile defining the invasive bladder tumor phenotype," *Urologic Oncology: Seminars and Original Investigations*, 29:794-801 (2011).

Zhang et al., "Dysregulation of angiogenesis-related microRNAs in endothelial progenitor cells from patients with coronary artery disease," *Biochem. Biophys. Res. Comm.*, 405:42-46 (2011).

Zhang et al., "MicroRNA Deregulation in Right Ventricular Outflow Tract Myocardium in Nonsyndromic Tetralogy of Fallot," *Canadian J. Cardiol.*, 29:1695-1703 (2013).

* cited by examiner

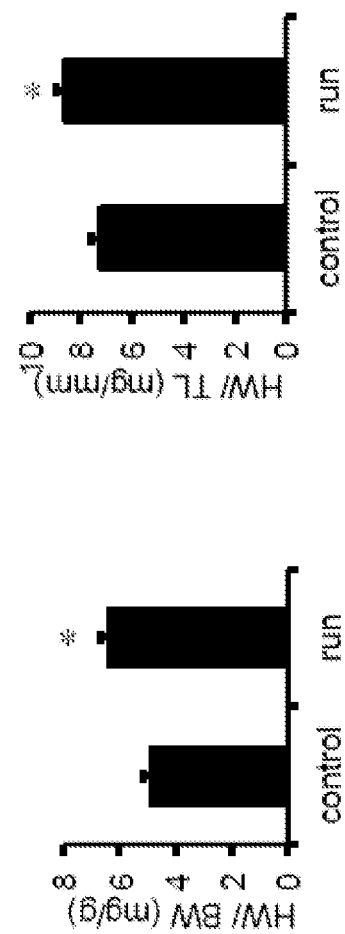
FIG. 9A FIG. 9B FIG. 9C FIG. 9D

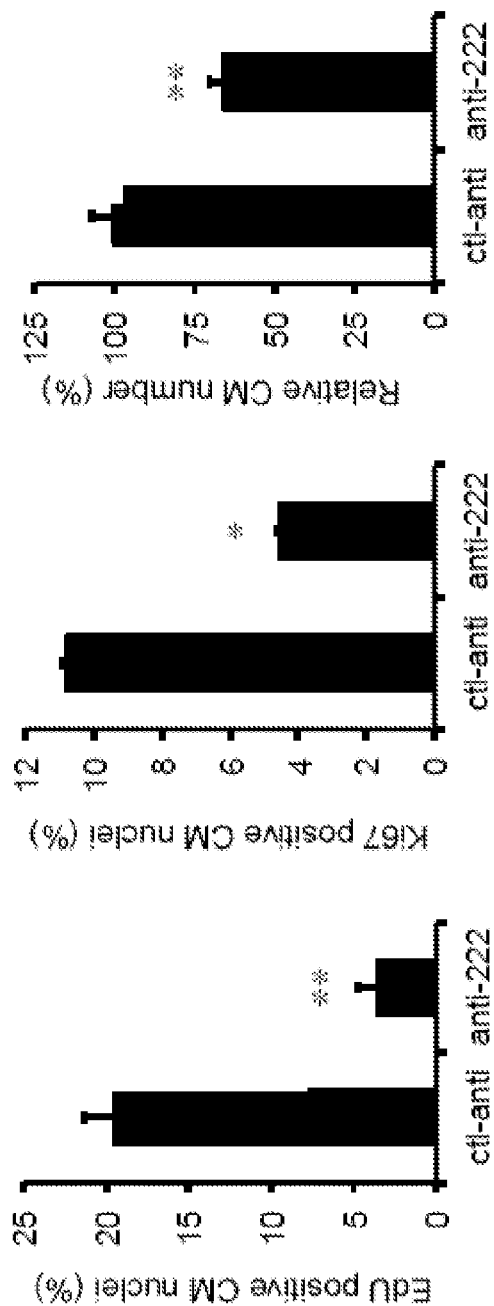
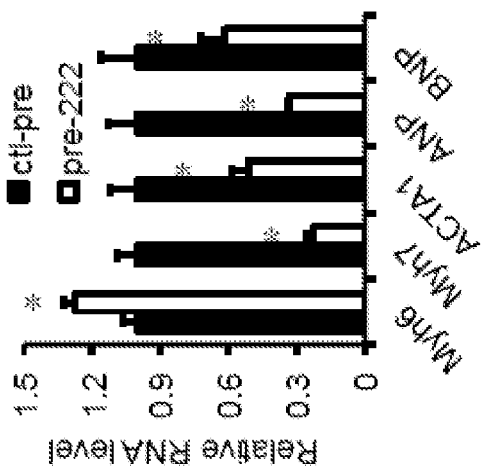
FIG. 11D
FIG. 11E

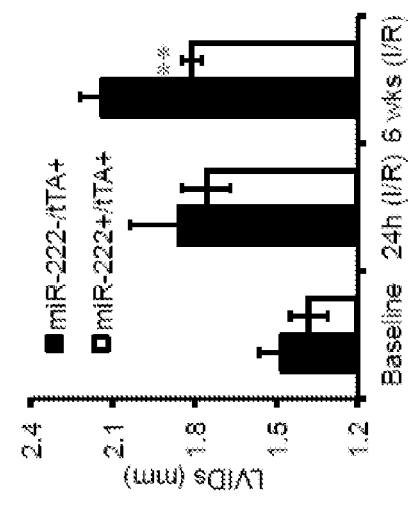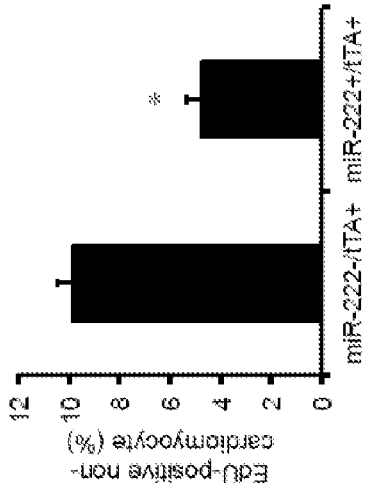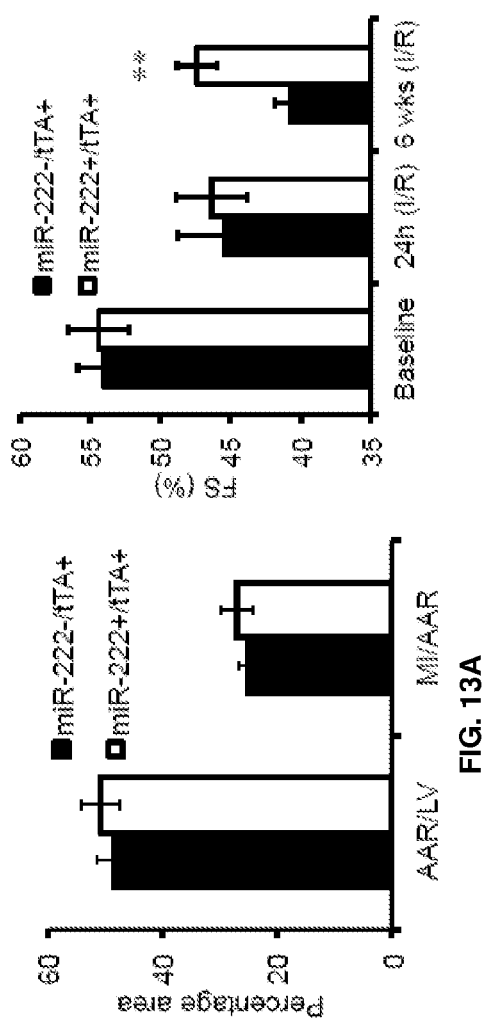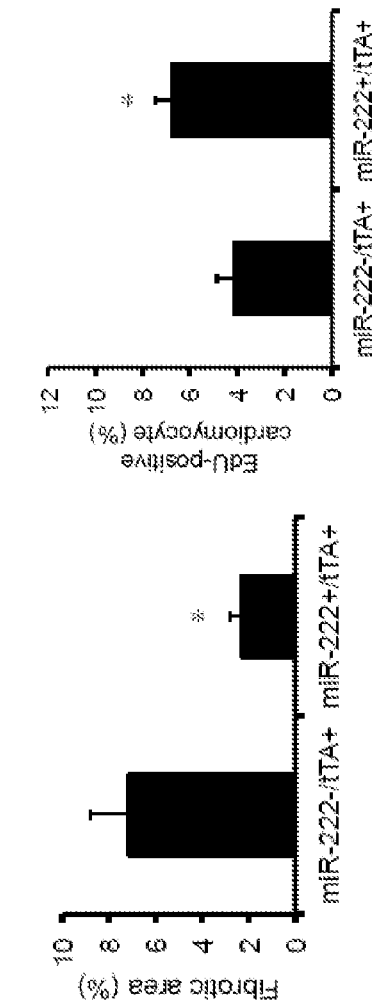
FIG. 13A
FIG. 13B
FIG. 13C
FIG. 13D

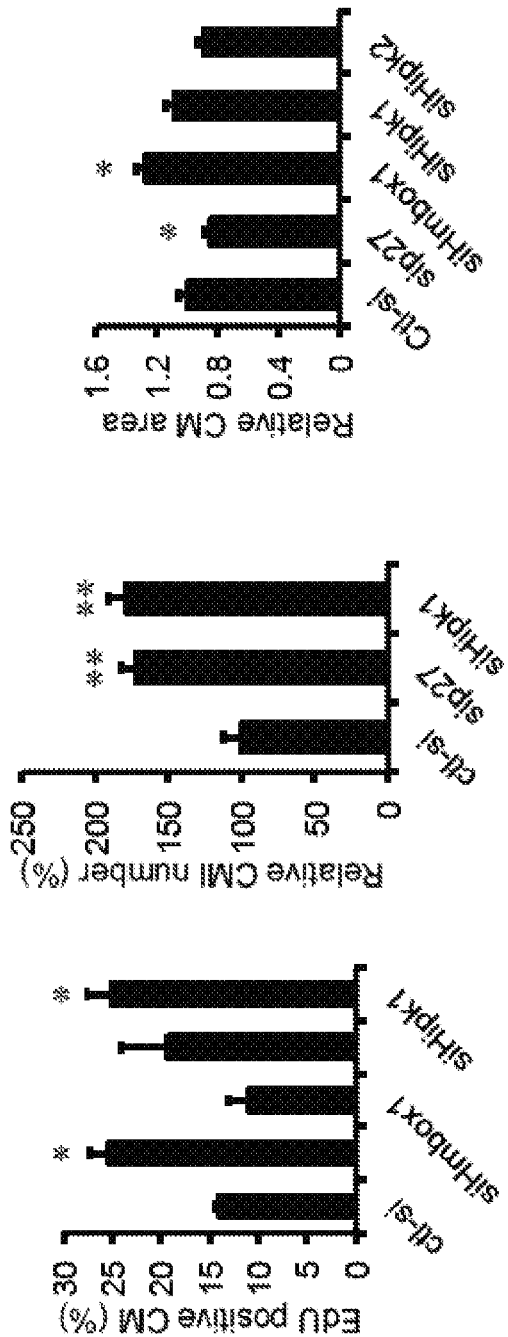
FIG. 14F
FIG. 14E
FIG. 14D
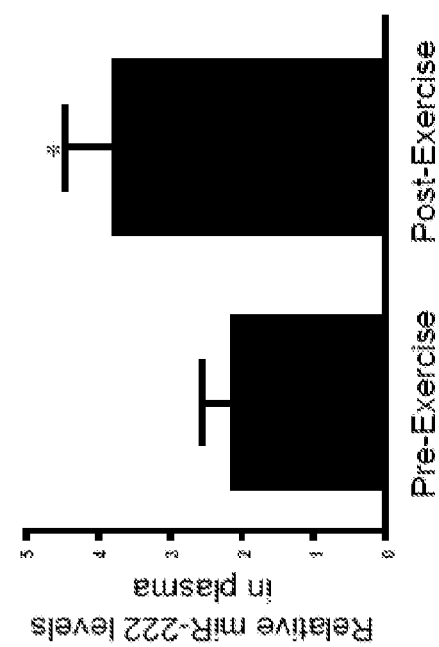
FIG. 15

SEQUENCE LISTING

<160> NUMBER OF SEQ ID NOS: 4

<210> SEQ ID NO 1
<211> LENGTH: 110
<212> TYPE: RNA
<213> ORGANISM: Homo sapiens

<400> SEQUENCE: 1
gcugcuggaa gguguaggua cccucaaugg cucaguagcc aguguagauc cugucuuucg    60
uaaucagcag cuacaucugg cuacuggguc ucgauggca ucuucuagcu               110

<210> SEQ ID NO 2
<211> LENGTH: 22
<212> TYPE: RNA

```
<213> ORGANISM: Homo sapiens

<400> SEQUENCE: 2
cucaguagcc aguguagauc cu                                              22

<210> SEQ ID NO 3
<211> LENGTH: 184
<212> TYPE: PRT
<213> ORGANISM: Homo sapiens

<400> SEQUENCE: 3

Met Ala Asp His Leu Met Leu Ala Glu Gly Tyr Arg Leu Val Gln Arg
1               5                   10                  15

Pro Pro Ser Ala Ala Ala His Gly Pro His Ala Leu Arg Thr Leu
            20                  25                  30

Pro Pro Tyr Ala Gly Pro Gly Leu Asp Ser Gly Leu Arg Pro Arg Gly
            35                  40                  45

Ala Pro Leu Gly Pro Pro Pro Arg Gln Pro Gly Ala Leu Ala Tyr
    50                  55                  60

Gly Ala Phe Gly Pro Pro Ser Ser Phe Gln Pro Phe Pro Ala Val Pro
65                  70                  75                  80

Pro Pro Ala Ala Gly Ile Ala His Leu Gln Pro Val Ala Thr Pro Tyr
                85                  90                  95

Pro Gly Arg Ala Ala Ala Pro Pro Asn Ala Pro Gly Gly Pro Pro Gly
            100                 105                 110

Pro Gln Pro Ala Pro Ser Ala Ala Ala Pro Pro Pro Ala His Ala
            115                 120                 125

Leu Gly Gly Met Asp Ala Glu Leu Ile Asp Glu Glu Ala Leu Thr Ser
    130                 135                 140

Leu Glu Leu Glu Leu Gly Leu His Arg Val Arg Glu Leu Pro Glu Leu
145                 150                 155                 160

Phe Leu Gly Gln Ser Glu Phe Asp Cys Phe Ser Asp Leu Gly Ser Ala
                165                 170                 175

Pro Pro Ala Gly Ser Val Ser Cys
            180

<210> SEQ ID NO 4
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gtagccagat gtagc                                                      15
```

COMPOSITIONS AND METHODS FOR CARDIAC REGENERATION

REFERENCE TO RELATED APPLICATIONS

This application is a 35 U.S.C. § 371 national stage filing of International Application No. PCT/US2014/066037, filed Nov. 18, 2014, which claims the benefit of U.S. provisional application No. 61/905,515, filed on Nov. 18, 2013. The entire contents of each of the foregoing applications are incorporated herein by reference.

GOVERNMENT SUPPORT

This invention was made with government support under HL110733, HL114352, HL007572, HL073734, GM007226 and TR000901 awarded by NIH. The government has certain rights in the invention.

BACKGROUND OF THE INVENTION

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. A particularly severe manifestation of heart disease is myocardial infarction. Myocardial infarction (MI), more commonly known as a heart attack, is a medical condition that occurs when the blood supply to a part of the heart is interrupted, most commonly due to rupture of a vulnerable plaque. The resulting ischemia or oxygen shortage causes damage and potential death of heart tissue. It is the leading cause of death for both men and women throughout the world. In the United States alone, coronary heart disease is responsible for 1 in 5 deaths, and some 7,200,000 men and 6,000,000 women are living with some form of coronary heart disease. Of these, 1,200,000 people suffer a new or recurrent coronary attack every year, and about 40% of them die as a result of the attack. This means that roughly every 65 seconds, an American dies of a coronary event.

Many MI events are either "silent" or are clinically unrecognized, but are nonetheless encompassed within this definition. The appearance of cardiac markers in the circulation generally indicates myocardial necrosis and is a useful adjunct to diagnosis. Such markers included ST-elevation MI (STEMI), non-ST-elevation MI (NSTEMI), and unstable angina.

If impaired blood flow to the heart lasts long enough, it triggers an ischemic cascade, where the heart cells die from necrosis and a collagen scar forms in their place. Recent studies indicate that cell death from apoptosis also plays a role in the process of tissue damage subsequent to myocardial infarction. As a result, the patient's heart will be permanently damaged. This scar tissue also puts the patient at risk for potentially life threatening arrhythmias, and may result in the formation of a ventricular aneurysm that can rupture with catastrophic consequences. Injured heart tissue conducts electrical impulses more slowly than normal heart tissue. The difference in conduction velocity between injured and uninjured tissue can trigger re-entry or a feedback loop that is believed to be the cause of many lethal arrhythmias. Cardiac output and blood pressure may fall to dangerous levels, which can lead to further coronary ischemia and extension of the infarct.

In addition to the direct effects on the infarcted tissue, adjacent tissues in the border zone around the infarct undergo a pathologic remodeling triggered by altered gene regulation. This remodeling results in further myocyte loss, hyperplasia and the further deposition of collagen in this region. Secondarily to the infarct, the remote myocardium responds to the infarct by cardiomyocyte hypertrophy and the onset of interstitial fibrosis. Thus, while the damage to the infarcted tissue maybe largely irreparable by the time an MI is diagnosed and addressed clinically, the further changes due to post-MI remodeling present a more likely point of therapeutic intervention.

Although the adult heart was traditionally been viewed as incapable of generating new cardiomyocytes, it is now believed that the heart has some limited capacity for regeneration and repair after injury, such as MI (Science 338 (6114):1549-50, 2012). This has been shown both in animal models and in humans (Science 324 (5923): 98-102, 2009). However, little is known about the signals that regulate formation of new cardiomyocytes in the adult heart, a process termed cardiomyogenesis, or how to exploit this therapeutically.

MicroRNAs (miRNAs) are small, non-protein coding RNAs of about 18 to about 25 nucleotides in length that are derived from individual miRNA genes, from introns of protein coding genes, or from poly-cistronic transcripts that often encode multiple, closely related miRNAs. See review by Carrington et al. (Science 301(5631):336-338, 2003). MiRNAs are thought to act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al., Cellular & Molecular Immunology 3:411-419, 2006) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. When an miRNA base pairs perfectly with an mRNA target, it is thought that it promotes mRNA degradation. More commonly, miRNAs form imperfect heteroduplexes with target mRNAs, affecting either mRNA stability or inhibiting mRNA translation.

SUMMARY OF THE INVENTION

One aspect of the invention provides a method of promoting physiological cardiomyocyte growth or proliferation in vivo, the method comprising promoting, in an adult subject in need thereof, expression or activity of a CITED4 (CBP/p300-Interacting Transactivator with ED-rich carboxy-terminal Domain 4) polypeptide or a functional fragment or fusion protein thereof from an expression construct.

In a related aspect, the invention provides a method of treating a heart disease treatable by cardiomyocyte regeneration and/or proliferation, the method comprising promoting, in an adult subject in need thereof, expression or activity of a CITED4 (CBP/p300-Interacting Transactivator with ED-rich carboxy-terminal Domain 4) polypeptide or a functional fragment or fusion protein thereof from an expression construct.

In yet another related aspect, the invention provides a method of promoting physiological cardiomyocyte growth or proliferation, the method comprising increasing the level of microRNA-222 (miR-222) or a precursor (e.g., pre-miR-222) or a mimic thereof in a cardiomyocyte or precursor thereof.

In still another related aspect, the invention provides a method of treating a heart disease treatable by cardiomyocyte regeneration and/or proliferation, the method comprising increasing, in an adult subject in need thereof, the level of miR-222 or a precursor (e.g., pre-miR-222) or a mimic thereof.

In certain embodiments, the expression or activity of the CITED4 polypeptide, or the level of miR-222, is increased in a cardiomyocyte of the subject.

In certain embodiments, the expression or activity of the CITED4 polypeptide, or the level of miR-222, is increased by administering to the subject an expression construct encoding the CITED4 polypeptide, or miR-222.

In certain embodiments, the expression construct is administered by intravenous administration; by direct injection into cardiac tissue; or by oral, transdermal, sustained release, controlled release, delayed release, suppository, subcutaneous, intramuscular, catheter or sublingual administration.

In certain embodiments, the expression construct is a viral vector, such as an adenoviral vector or an adeno-associated viral (AAV) vector, the latter of which may be AAV1, AAV2, or AAV9, or a combination thereof.

In certain embodiments, the AAV vector is delivered to the subject via intracoronary infusion.

In certain embodiments, the expression of CITED4 or level of miR-222 is increased in the cardiomyocyte or precursor thereof by contacting the cardiomyocyte or precursor thereof with a synthetic, modified RNA.

In certain embodiments, the heart disease is myocardial infarction or ischemic injury; adverse remodeling after ischemic injury or infarction; myocarditis; heart failure (congestive), cardiomyopathy (e.g., ischemic cardiomyopathy, dilated cardiomyopathy, hypertrophic cardiomyopathy, restrictive cardiomyopathy, alcoholic cardiomyopathy, viral cardiomyopathy, tachycardia-mediated cardiomyopathy, stress-induced (takotsubo) cardiomyopathy, amyloid cardiomyopathy, arrhythmogenic right ventricular dysplasia, or unclassified cardiomyopathy, left ventricular noncompaction or endocardial fibroelastosis); valvular heart disease (e.g., aortic stenosis, aortic regurgitation, mitral stenosis, mitral regurgitation, mitral prolapse, pulmonary stenosis, pulmonary regurgitation, tricuspid stenosis, or tricuspid regurgitation).

In certain embodiments, therapeutic efficacy is achieved by alleviating at least one symptom of the heart disease (e.g., heart failure), or by inhibiting or retarding the worsening of the symptom. In certain embodiments, therapeutic efficacy is measured by a decrease in a symptom of heart failure (e.g., as measured by New York Heart Association class, Minnesota Living With Heart Failure Questionnaire), an augment in functional status (e.g., as measured by 6-minute walk test, peak maximum oxygen consumption), a decrease in natriuretic peptide level (e.g., N-terminal prohormone brain natriuretic peptide), and/or beneficial reverse left ventricular (LV) remodeling (left ventricular ejection fraction, left ventricular end-systolic volume).

In certain embodiments, the method further comprises administering to the subject a second cardiac therapy. For example, the second therapy may be selected from the group consisting of a β blocker, an ionotrope, a diuretic, ACE-I, AII antagonist, BNP, a $Ca^{2+}$-blocker, an endothelin receptor antagonist, and an HDAC inhibitor.

In certain embodiments, the heart disease is myocardial infarction, and wherein fibrosis and/or apoptosis in the infarct zone is reduced.

In certain embodiments, the subject is a human.

Another aspect of the invention provides an expression construct capable of directing in vivo expression of a CITED4 polypeptide or a functional fragment or fusion protein thereof.

Another aspect of the invention provides an expression construct capable of directing expression of miR-222 or a precursor or a mimic thereof.

Another aspect of the invention provides a method of identifying miR-222 mimics, the method comprising: (1) contacting a first cardiomyocyte with miR-222, or an expression vector that expresses miR-222 in the first cardiomyocyte, and determining a first extent of cardiomyocyte growth or proliferation; (2) contacting a second cardiomyocyte with a candidate compound under substantially the same condition as in (1), and determining a second extent of cardiomyocyte growth or proliferation; (3) comparing the first extent of cardiomyocyte growth or proliferation with the second extent of cardiomyocyte growth or proliferation; wherein the candidate compound is identified as a miR-222 mimic when the first extent of cardiomyocyte growth or proliferation is substantially the same as the second extent of cardiomyocyte growth or proliferation.

It is contemplated that any embodiment described herein, including those described only in the examples or one section or aspects of the invention, can be generally combined with respect to any method or composition of the invention. Furthermore, compositions and kits of the invention can be used to achieve methods of the invention.

Throughout this application, the term "about" is used to indicate that a value includes the standard deviation of error for the device or method being employed to determine the value. Alternatively, "about" is within 5% of the value being modified.

BRIEF DESCRIPTION OF THE DRAWINGS

In FIG. 4A, sedentary or swum mice were intravenously injected with LNA-antimiR-222 or control LNA-antimiR for 3 weeks prior to quantification of cardiac miR-222 to demonstrate effective reduction after injection of LNA-antimiR-222. In FIGS. 4B and 4C, heart weight/body weight (HW/BW) and heart weight/tibia length (HW/TL) ratios are shown for sedentary control (control, n=15) and swum (swim, n=16) mice without injection, as well as swum mice injected with control LNA-antimiR (swim ctl-anti, n=7) or LNAantimiR-222 (swim anti-222, n=6). These studies demonstrate that LNA-antimiR-222 completely blocks cardiac growth in response to swimming. In FIG. 4D, quantification of cardiomyocyte area from heart sections stained with wheat germ agglutinin (WGA) (n=5-6, ~500 cells per animal) demonstrate that LNA-antimiR-222 also blocks exercise-induced cardiomyocyte hypertrophy. Immunohistochemical staining for phospho-histoneH3 (pHH3) E and Ki67 (F) from heart sections and quantification (n=5-6 hearts in each group) demonstrate that LNA-antimiR-222 reduces markers of cardiomyocyte proliferation. Scale bar: 100 μm. Error bars stand for standard errors. *$p<0.05$, versus sedentary; # $p<0.05$ versus swum ctl-anti using One-way ANOVA.

FIGS. 9A-9E show differentially expressed microRNAs in hearts from exercised mice. FIGS. 9A and 9B show heart weight/body weight (HW/BW) and heart weight/tibial length (HW/TL) ratios of sedentary control (control) and swum (swim) mice. n=9 mice per group. FIGS. 9C and 9D show heart weight/body weight (HW/BW) and heart weight/tibia length (HW/TL) ratios of sedentary (control) and voluntary-wheel run (run) mice. n=4 mice per group. Heat map of 40 differentially regulated miRNAs concordantly altered in hearts from mice after swimming and running protocols compared to sedentary controls is not shown. The TaqMan rodent miR array (A+B set v3.0) was used to examine 641 specific mouse miRs in hearts from mice exercised for three weeks by wheel running or an intensive swim protocol. n=3, 3 mouse hearts per pool. FIG. 9E shows qRT-PCR analysis of the identified 40 differentially regulated miRNAs in hearts from separate cohorts. n=5 hearts per group. Error bars stand for standard errors. *$p<0.05$, **$p<0.01$ versus respective control using Student's test.

FIG. 10A shows immunohistochemistry against sarcomeric α-actinin followed by quantification of cell area in neonatal cardiomyocytes transfected with the indicated microRNAs or treated with phenylephrine (PE). FIG. 10B shows flow cytometry analysis of EdU incorporation in neonatal cardiomyocytes transfected with control precursor, precursors of the indicated miRNAs, or precursor for has-miR-590-3p as a positive control. Cumulative data from three independent experiments are shown. FIG. 10C shows qRT-PCR analysis of the relative ratio of α/β-MHC in neonate cardiomyocytes transfected with indicated miR precursors. Cumulative data from three independent experiments are shown. All data are represented as mean±SEM. *$p<0.05$ versus respective control using Student's t-test.

FIGS. 11A-11E show that miR-222 is necessary and sufficient for cardiomyocyte hypertrophy and proliferation. FIGS. 11A and 11B show immunohistochemical staining for sarcomeric α-actinin (image not shown) followed by quantification of cardiomyocyte area as described in methods. Cells were transfected with control or miR-222 precursor in FIG. 11A and with control antimiR (ctl-anti) or antimiR-222 (anti-222) in FIG. 11B. At least 200 cells were quantified in each group. These data demonstrate that miR-222 is necessary and sufficient to induce cardiomyocyte hypertrophy in vitro. FIG. 11C shows quantification of EdU incorporation staining (left panel), Ki67 staining (middle panel), and cell number (right panel) from primary NRVMs transfected with control precursor (ctl-pre) or miR-222 precursor (pre-222). FIG. 11D shows quantification of EdU incorporation staining, Ki67 staining, and cell number from NRVMs transfected with control antimiR (ctl-anti) or antimiR-222 (anti-222). These data demonstrate miR-222 is necessary and sufficient to induce neonatal cardiomyocyte proliferation in vitro. FIG. 11E shows qRT-PCR analysis of cardiomyocyte gene expression in NRVMs treated with control (ctl-pre) or miR-222 precursor (pre-222). These data demonstrate that miR-222 induces a physiological pattern of gene expression in vitro is consistent with the exercise-induced patterns seen in vivo. Data shown as mean fold induction ±SEM of gene expression normalized to U6 from at least three independent experiments. Scale bar: 100 μm. *$p<0.05$, **$p<0.01$ versus respective control using Student's test.

FIG. 12A shows qRT-PCR analysis of microRNA expression in hearts of tTA single (miR-222$^-$/tTA$^+$) and double (miR-222$^+$/tTA$^+$) 3 month old transgenic mice 4 weeks after doxycycline removal from chow to induce miR-222 expression in double-transgenic mice. Data are shown as fold induction of microRNA expression normalized to U6. Cumulative data from 4 to 6 mice for each genotype are shown. FIG. 12B shows heart weight/tibial length (HW/TL) ratios of tTA single (miR-222$^-$/tTA$^+$) and double (miR-222$^+$/tTA$^+$) 3 month old transgenic mice (male and female) 4 weeks after doxycycline removal from chow to induce miR-222 expression in double-transgenic mice. Cumulative data from 4 to 6 mice for each genotype are shown. p=ns. Error bars represent standard errors. *$p<0.05$, **$p<0.01$ compared with respective controls using Student's t-test.

FIGS. 13A-13D show that cardiac-specific expression of miR-222 protects against adverse remodeling and dysfunction after ischemic injury. FIG. 13A demonstrates that there is no difference in initial infarct size or the area-at-risk (AAR), in miR-222 expressing hearts. Tiphenyltetrazolium chloride (TTC) staining was used to delineate infarct area, and fluorescent microsphere distribution was used to define the AAR in hearts from tTA single (miR-222$^-$/tTA$^+$) and double transgenic (miR-222$^+$/tTA$^+$) mice, 24 hours after reperfusion after 30 minutes of ischemia. Representative photographs of TTC staining and fluorescent microsphere distribution of medial sections of cardiac tissues are not shown (cumulative quantification (n=6-7) in each group).

FIG. 13B shows cardiac fractional shortening and left ventricular internal dimension in systole (LVIDs) as measured by transthoracic echocardiography in tTA single (miR-222$^-$/tTA$^+$) and double transgenic (miR-222$^+$/tTA$^+$) mice at baseline, 24 hours or 6 weeks after ischemic injury (n=8-9 mice in each group). These data demonstrate similar cardiac dysfunction at 24 hours but better function and less dilation in miR-222 expressing hearts at 6 weeks. In FIG. 13C, masson trichrome staining (n=6-7 hearts in each group) demonstrates less fibrosis in miR-222-expressing double transgenic hearts at 6 weeks after ischemic injury. In FIG. 13D, immunofluorescence demonstrates increased EdU incorporation in cardiomyocytes in miR-222-expressing hearts after ischemic injury but reduced EdU incorporation in non-cardiomyocytes (n=5 animals in each group, ~2500 cells counted per animal). Scale bar: 100 µm. Data shown as mean±SEM. *p<0.05, **p<0.01 versus respective control using Student's test.

FIG. 14A-14F show miR-222 targets in cardiomyocytes. In FIGS. 14A and 14B, qRT-PCR and immunoblotting were used to analyze RNA and protein levels of the four putative miR-222 targets in neonatal cardiomyocytes treated with control precursor (ctl-pre), miR-222 precursor (pre-222), control antimiR (ctl-anti), or antimiR-222 (anti-222), as indicated. Data are shown as fold induction of gene expression normalized to U6 in (FIG. 14A). These data demonstrate that miR-222 decreases RNA and protein levels for all four targets in primary cardiomyocytes. Not shown here are results of luciferase assays of COST cells cotransfected with control precursor (ctl-pre) or miR-222 precursor (pre-222) and reporter plasmids containing 3'UTR wild-type or mutated miR-222 binding sites for each of the three putative novel targets. These data demonstrate all three candidates are direct targets of miR-222. In FIG. 14C, immunoblotting of the four target genes in neonatal cardiomyocytes transfected with control siRNA (ctl-si) or siRNAs for p27 (sip27), Hmbox1 (siHmbox1), Hipk1 (siHipk1) or Hipk2 (siHipk2) demonstrate effective knockdown for all. HSP90 was used as a loading control. In FIG. 14D, flow cytometry for EdU incorporation in neonatal cardiomyocytes transfected with the indicated siRNAs demonstrates that knockdown of p27 or HIPK1 increases EdU incorporation in cardiomyocytes. In FIGS. 14E and 14F, neonatal cardiomyocytes were stained for sarcomeric α-actinin before quantification of cardiomyocyte number and area. Knockdown of p27 or HIPK1 increases cardiomyocyte proliferation (FIG. 14E) while Hmbox1 knockdown increases cardiomyocyte size (FIG. 14F). At least 200 cells in 30 images were quantified in each group. Data represent the mean±SEM from at least three independent experiments. Scale bar: 100 µm. *p<0.05, **p<0.01 versus respective control using Student's test.

FIG. 15 shows that plasma miR-222 levels in heart failure patients are increased after acute exercise. The figure shows qRT-PCR analysis of miR-222 levels in plasma from heart failure patients before (pre-exercise) and after (post-exercise) acute cardiopulmonary exercise using a bicycle ergometer. miR-222 expression are shown as mean±standard error from 28 patients, normalized to exogenously added cel-miR-39. *p<0.01 using Student's test.

DETAILED DESCRIPTION OF THE INVENTION

1. Overview

Figure 1:
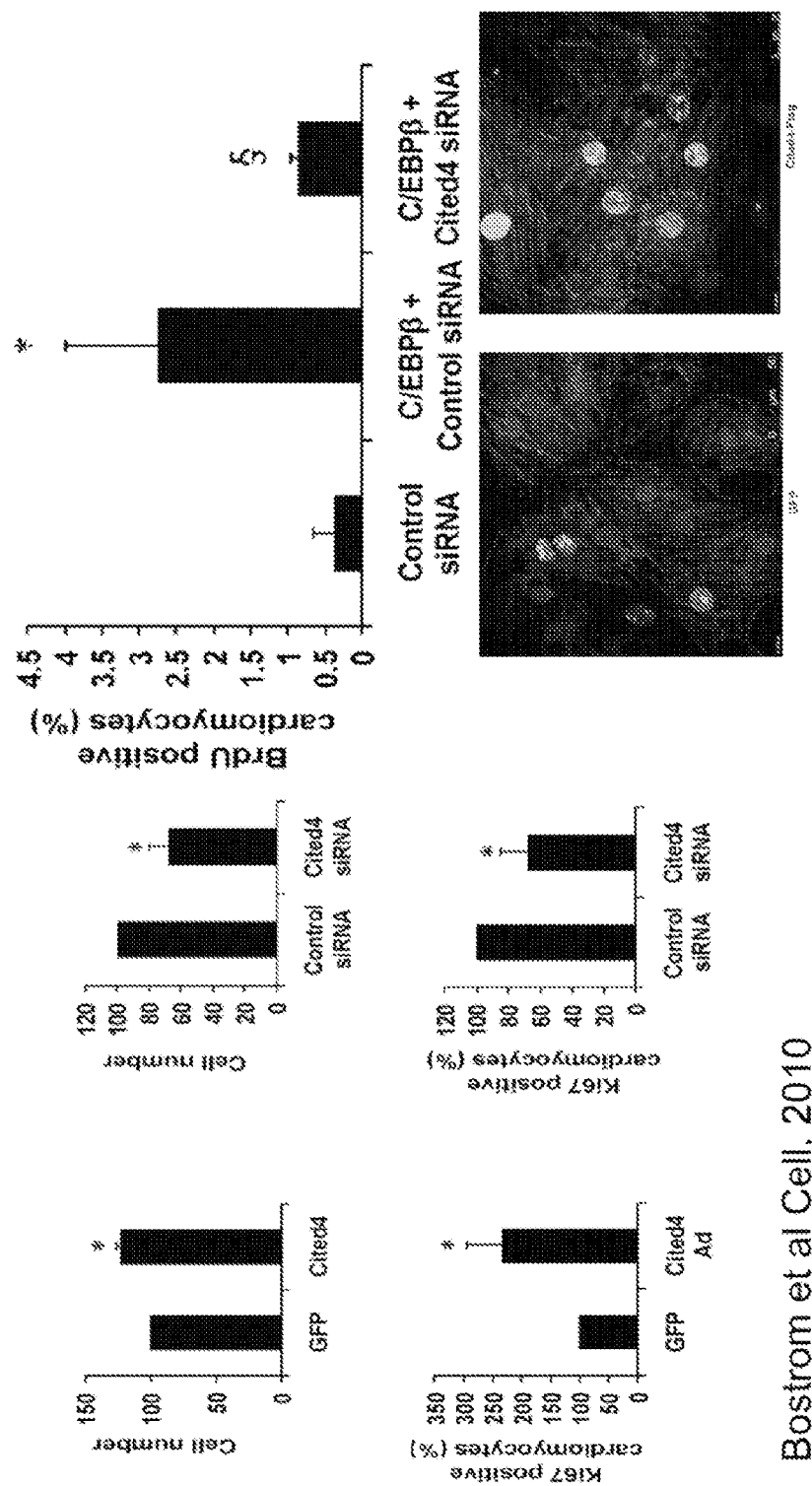
FIG. 1 shows that CITED4 induces proliferation of neonatal cardiomyocytes in vitro. Specifically, in the last four panels and the bottom right panels, rat neonatal cardiomyocytes were treated with either an adenovirus overexpressing CITED4 or an siRNA directed against CITED4. Cells were then stained against α-actinin and ki67, and positive cells were counted in 20× view fields from 15 random images per group. In the top right panel, rat neonatal cardiomyocytes were treated with control siRNA, C/EBPb siRNA+control siRNA, or C/EBPb siRNA+Cited4 siRNA, followed by assay of BrdU incorporation. Data is pooled from three experiments and presented as percent of control. Error bars represent standard error of mean. *p<0.05 versus respective control, and x versus C/EBPb siRNA using one-way ANOVA statistics. T test was used. See Bostrom et al. (Cell 143: 1072-1083, 2010).

The present invention is based, at least in part, on the surprising discovery that, although forced expression of a CITED4 polypeptide fails to stimulate adult cardiomyocyte (CM) proliferation in vitro, it is nevertheless sufficient to stimulate CM growth and proliferation in vivo.

The present invention is also based, at least in part, on the discovery that microRNA-222 (miR-222) also promotes cardiomyocyte (CM) proliferation, and that the full beneficial effect of miR-222 may not be fully recapitulated by targeting individual members of a multitude of miR-222 downstream target genes.

Thus the discoveries provide new and useful methods and reagents for treating or preventing a host of cardiovascular diseases and pathological conditions of the heart, including myocardial infarction, heart failure, and scar formation (fibrosis) resulting therefrom, in animals such as in humans, by increasing the expression, activity, or level of a CITED4 polypeptide (or functional fragments or fusions thereof), and/or miR-222 (or precursors or mimics thereof).

Accordingly, the invention provides a method of promoting physiological cardiomyocyte growth (increase in cell size but not cell proliferation) or proliferation (increase in cell number) in vivo, the method comprising promoting, in an adult subject in need thereof, expression or activity of a CITED4 (CBP/p300-Interacting Transactivator with ED-rich carboxy-terminal Domain 4) polypeptide or a functional fragment or fusion protein thereof.

In a related aspect, the invention provides a method of treating a heart disease treatable by cardiomyocyte regeneration and/or proliferation, the method comprising promoting, in an adult subject in need thereof, expression or activity of a CITED4 polypeptide or a functional fragment or fusion protein thereof.

As used herein, the term "heart failure" is broadly used to mean any condition in which the function of the heart is inadequate to meet the systemic needs of the metabolic, whether the impaired function is due to reduced contraction (systolic dysfunction) or due to reduce relaxation (diastolic dysfunction). In both conditions, diastolic pressures in the heart increase, resulting in congestion and edema in the tissues. Most frequently, heart failure is caused by decreased contractility of the myocardium, resulting from MI or reduced coronary blood flow; however, many other factors may result in heart failure, including damage to the heart valves, vitamin deficiency, and primary cardiac muscle disease. In addition, many cases of heart failure are now recognized to result from impaired relaxation of the heart, whether due to scarring (fibrosis), abnormal calcium handling and/or thickening of the heart muscle (hypertrophy). Though the precise physiological mechanisms of heart failure are not entirely understood, heart failure is generally believed to involve disorders in several cardiac autonomic properties, including sympathetic, parasympathetic, and baroreceptor responses.

The phrase "manifestations of heart failure" is used broadly to encompass all of the sequelae associated with heart failure, such as shortness of breath, pitting edema, an enlarged tender liver, engorged neck veins, pulmonary rales, decreased energy and fatigue, and the like including laboratory findings associated with heart failure.

The term "treatment," "treating," or other grammatical equivalents encompasses the amelioration, cure, maintenance (i.e., the prevention of relapse), improvement, and/or reversal of the symptoms of a cardiovascular disease or pathological condition being treated. Treatment after a disease or disorder has started or manifested aims to reduce, ameliorate, or altogether eliminate the disorder, and/or its associated symptoms, to prevent it from becoming worse, or to prevent the disorder from re-occurring once it has been initially eliminated (i.e., to prevent a relapse). In certain embodiments, treatment does not include prevention.

In the case of treating heart failure, treatment may include the improvement and/or reversal of the diminished ability of the heart to pump blood or its impaired relaxation. Improvement in the physiologic function of the heart may be assessed using any of the measurements described herein (e.g., measurement of ejection fraction, fractional shortening, left ventricular internal dimension, heart rate, etc.), as well as any effect upon the animal's survival.

In certain embodiments, the method is not subjecting the subject to physical exercise. In certain embodiments, the method comprises promoting expression or activity of the CITED4 polypeptide or a functional fragment or fusion protein thereof from an expression construct, preferably in heart cells or cardiomyocytes of the subject.

In another related aspect, the invention provides a method of promoting physiological cardiomyocyte growth or proliferation, the method comprising increasing the level of microRNA-222 (miR-222) or a precursor (e.g., pre-miR-222) or a mimic thereof in a cardiomyocyte or precursor thereof.

In another related aspect, the invention provides a method of treating a heart disease treatable by cardiomyocyte regeneration and/or proliferation, the method comprising increasing, in an adult subject in need thereof, the level of miR-222 or a precursor (e.g., pre-miR-222) or a mimic thereof.

In certain embodiments, the method is not subjecting the subject to physical exercise. In certain embodiments, the method comprises increasing the level of miR-222 or a precursor (e.g., pre-miR-222) or a mimic thereof, preferably in heart cells or cardiomyocytes of the subject.

As used herein, the term "subject" (or "patient" hereinafter) include any vertebrate species, particularly mammals, including, without limitation, humans and other non-human primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In some embodiments, the subject is a human. In certain embodiments, the CITED4 polypeptide and/or miR-222 used in the methods of the invention are from the same species of the subject. For example, in such embodiments in which the subject to be treated is human, the CITED4 polypeptide or miR-222 to be used in the methods of the invention are of human origin. In certain embodiments, however, the CITED4 polypeptide and/or miR-222 used in the methods of the invention may be from a different species, such as a closely related species, or a heterologous sequence sharing at least about 80, 85, 90, 95% sequence identity.

In certain embodiments, the expression or activity of the CITED4 polypeptide, or the level of miR-222, is increased by administering to the subject an expression construct encoding the CITED4 polypeptide, or miR-222. Numerous suitable expression constructs and administrative routes and methods are known in the art, and illustrative examples of which are described in further details below.

For example, the expression construct may be administered by intravenous administration; by direct injection into cardiac tissue; or by oral, transdermal, sustained release, controlled release, delayed release, suppository, subcutaneous, intramuscular, catheter or sublingual administration.

In certain embodiments, the expression construct may be a viral vector, such as an adenoviral vector or an adeno-associated viral (AAV) vector. Certain particularly suitable AAV vectors include AAV1, AAV2, and AAV9.

The AAV1 vector, for example, may be delivered to the subject via intracoronary infusion. In a recently conducted randomized, double-blind, placebo-controlled, phase 2 clinical trial in patients with advanced heart failure, Jessup et al. (*Circulation* 124: 304-313, 2011) reported that an Adeno-Associated Virus type 1 (AAV1) viral vector was used to exogenously express sarcoplasmic reticulum $Ca^{2+}$-ATPase (SERCA2a) in patients with advanced heart failure, demonstrating safety and feasibility of the gene transfer therapy, as well as therapeutic efficacy.

In certain embodiments, the expression of CITED4 or level of miR-222 is increased in the cardiomyocyte or precursor thereof by contacting the cardiomyocyte or precursor thereof with a synthetic, modified RNA.

In certain embodiments, the heart disease is myocardial infarction or ischemic injury; adverse remodeling after ischemic injury or infarction; myocarditis; heart failure (congestive), cardiomyopathy (e.g., ischemic cardiomyopathy, dilated cardiomyopathy, hypertrophic cardiomyopathy, restrictive cardiomyopathy, alcoholic cardiomyopathy, viral cardiomyopathy, tachycardia-mediated cardiomyopathy, stress-induced (takotsubo) cardiomyopathy, amyloid cardiomyopathy, arrhythmogenic right ventricular dysplasia, or unclassified cardiomyopathy, left ventricular noncompaction or endocardial fibroelastosis); valvular heart disease (e.g., aortic stenosis, aortic regurgitation, mitral stenosis, mitral regurgitation, mitral prolapse, pulmonary stenosis, pulmonary regurgitation, tricuspid stenosis, or tricuspid regurgitation).

In certain embodiments, therapeutic efficacy is achieved based on the methods of the invention, by alleviating at least one symptom of the heart disease (e.g., heart failure), or by inhibiting or retarding the worsening of the symptom.

For example, in the case of heart failure, therapeutic efficacy may be measured by a decrease in a symptom of heart failure (e.g., as measured by New York Heart Association class, Minnesota Living With Heart Failure Questionnaire), an augment in functional status (e.g., as measured by 6-minute walk test, peak maximum oxygen consumption), a decrease in natriuretic peptide level (e.g., N-terminal prohormone brain natriuretic peptide), and/or beneficial reverse left ventricular (LV) remodeling (left ventricular ejection fraction, left ventricular end-systolic volume).

In certain embodiments, the methods of the invention further comprise administering to the subject a second cardiac therapy, such as one selected from the group consisting of: a β blocker, an ionotrope, a diuretic, ACE-I, AII antagonist, BNP, a $Ca^{2+}$-blocker, an endothelin receptor antagonist, and an HDAC inhibitor.

In certain embodiments, the heart disease is myocardial infarction, and wherein fibrosis and/or apoptosis in the infarct zone is reduced.

Another aspect of the invention provides an expression construct capable of directing in vivo expression of a CITED4 polypeptide or a functional fragment or fusion protein thereof.

Still another aspect of the invention provides an expression construct capable of directing expression of miR-222 or a precursor (e.g., pre-miR-222) or a mimic thereof.

Suitable vectors or expression constructs are described in further details below.

Another aspect of the invention provides a pharmaceutical composition comprising a subject CITED4 polypeptide or a functional fragment or fusion protein thereof, or miR-222 or a precursor (e.g., pre-miR-222) or mimic thereof, or an expression construct encoding the same, and a pharmaceutically acceptable carrier, excipient, or buffer.

The pharmaceutically acceptable carrier or excipient may be suitable for rendering the compound or mixture administrable orally as a tablet, capsule or pill, or parenterally, intravenously, intradermally, intramuscularly or subcutaneously, or transdermally. The active ingredients may be admixed or compounded with any conventional, pharmaceutically acceptable carrier or excipient.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Except insofar as any conventional media or agent is incompatible with the compositions of this invention, its use in the therapeutic formulation is contemplated. Supplementary active ingredients can also be incorporated into the pharmaceutical formulations. A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, *Remington's Pharmaceutical Sciences*, 18th Ed. (1990).

Another aspect of the invention further provides a pharmaceutical pack or kit comprising one or more containers filled with one or more of the ingredients of the pharmaceutical compositions of the invention. Associated with such container(s) can be various written materials (written information) such as instructions (indicia) for use, or a notice in the form prescribed by a governmental agency regulating the manufacture, use or sale of pharmaceuticals or biological products, which notice reflects approval by the agency of manufacture, use or sale for human administration.

Yet another aspect of the invention provides a method to screen for/identify miR-222 mimics among a plurality of candidates, comprising (1) contacting a first cardiomyocyte with miR-222, or an expression vector that expresses miR-222 in the first cardiomyocyte, and determining a first extent of cardiomyocyte growth or proliferation; (2) contacting a second cardiomyocyte with a candidate compound under substantially the same condition as in (1), and determining a second extent of cardiomyocyte growth or proliferation; (3) comparing the first extent of cardiomyocyte growth or proliferation with the second extent of cardiomyocyte growth or proliferation; wherein the candidate compound is identified as a miR-222 mimic when the first extent of cardiomyocyte growth or proliferation is substantially the same as the second extent of cardiomyocyte growth or proliferation.

In certain embodiments, the first or second extent of cardiomyocyte growth or proliferation is measured by the presence/absence or level of expression of a marker gene, such as a marker gene for cardiomyocyte growth or proliferation. Exemplary marker genes include Ki67, EdU, phospho-histone H3 (PPH3), TnT, and/or Aurora B kinase in cardiomyocytes identified by virtue of Troponin T expression.

In certain embodiments, the candidate compound is a chemically modified nucleic acid. For example, the chemically modified nucleic acid may have substantially identical sequence as the wildtype miR-222 sequence or the CITED4 mRNA sequence, but contains one or more modified nucleic acid that enhances serum stability, cellular in-take, and/or nuclease resistance, and/or reduces the host immune or inflammatory response.

Specifically, chemically synthesized nucleic acid molecules with modifications (base, sugar and/or phosphate) may resist degradation by serum ribonucleases, and may have increased potency. See, e.g., Eckstein et al., International Publication No. WO 92/07065; Perrault et al, 1990 *Nature* 344:565; Pieken et al., 1991, *Science* 253:314; Usman and Cedergren, 1992, *Trends in Biochem. Sci.* 17:334; Usman et al., International Publication No. WO 93/15187; and Rossi et al., International Publication No. WO 91/03162; Sproat, U.S. Pat. No. 5,334,711; and Burgin et al., supra. All of these publications (all incorporated by reference herein) describe various chemical modifications that can be made to the base, phosphate and/or sugar moieties of the nucleic acid molecules herein. Modifications which enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS.* 17:34; Usman et al., 1994, *Nucleic Acids Symp. Ser.* 31:163; Burgin et al., 1996, *Biochemistry,* 35:14090). Sugar modification of nucleic acid molecules have been extensively described in the art (see Eckstein et al., International Publication PCT No. WO 92/07065; Perrault et al., *Nature,* 1990, 344:565-568; Pieken et al. *Science,* 1991, 253:314-317; Usman and Cedergren, *Trends in Biochem. Sci.,* 1992, 17:334-339; Usman et al., International Publication PCT No. WO 93/15187; Sproat, U.S. Pat. No. 5,334,711; Beigelman et al., 1995, *J. Biol. Chem.,* 270:25702; Beigelman et al., International PCT publication No. WO 97/26270; Beigelman et al., U.S. Pat. No. 5,716,824; and Usman et al., molecule comprises one or more chemical modifications.

In certain embodiments, miR-222 or precursor or mimic thereof contains DNA, RNA, modification thereof (e.g., LNA or PNA etc.), and/or combinations thereof.

Locked Nucleic Acids (LNAs) or LNAs comprise sugar-modified nucleotides that resist nuclease activities (thus highly stable), and possess single nucleotide discrimination for mRNA (Elmen et al., *Nucleic Acids Res.,* 33(1): 439-447, 2005; Braasch et al., *Biochemistry,* 42:7967-7975, 2003; Petersen et al., *Trends Biotechnol.,* 21:74-81, 2003). These molecules have 2'-0,4'-C-ethylene-bridged nucleic acids, with possible modifications such as 2'-deoxy-2"-fluorouridme. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

Peptide Nucleic Acids (PNAs) or PNAs comprise modified nucleotides in which the sugar-phosphate portion of the nucleotide is replaced with a neutral 2-amino ethylglycine moiety capable of forming a polyamide backbone, which is highly resistant to nuclease digestion, and imparts improved binding specificity to the molecule (Nielsen et al., Science, 254:1497-1500, 2001).

In certain embodiments, the oligonucleotide of the invention comprises Morpholino nucleic acid analog, or "PMO" (phosphorodiamidate morpholino oligo). Morpholinos are synthetic nucleic acid analogs that bind to complementary sequences of RNA by standard nucleic acid base-pairing. Structurally, Morpholinos are similar to DNA in that Morpholinos have standard nucleic acid bases. However, those bases are bound to morpholine rings instead of deoxyribose rings and linked through phosphorodiamidate groups instead of phosphates. Replacement of anionic phosphates with the uncharged phosphorodiamidate groups eliminates ionization in the usual physiological pH range, so Morpholinos in organisms or cells are uncharged molecules. The entire backbone of a Morpholino is made from these modified subunits.

In certain embodiments, miR-222 or precursor or mimic thereof contains Glycol Nucleic A (GNA), which is a synthesized polymer similar to DNA or RNA but differing in the composition of its backbone. Specifically, DNA and RNA have a deoxyribose and ribose sugar backbone, respectively, whereas GNA's backbone is composed of repeating glycol units linked by phosphodiester bonds. The glycol unit has just three carbon atoms, yet still shows Watson-Crick base pairing, and the Watson-Crick base pairing is much more stable in GNA than its natural counterparts DNA and RNA as it requires a high temperature to melt a duplex of GNA. The 2,3-dihydroxypropylnucleoside analogues were first prepared by Ueda et al. (1971).

In certain embodiments, miR-222 or precursor or mimic thereof contains Threose Nucleic Acid (TNA), which is a synthetic nucleic acid analog similar to DNA or RNA but differing in the composition of its backbone. Specifically, TNA's backbone is composed of repeating threose units linked by phosphodiester bonds. TNA can hybridize with RNA and DNA in a sequence-specific manner. TNA is also capable of Watson-Crick pair bonding, and forming a double helix structure.

The following sections provide additional detailed descriptions for the various aspects of the invention.

2. MicroRNA-222 (miR-222)

In certain embodiments, the invention provides methods of using a subject miR-222 microRNA or precursor or mimic thereof for treating the various cardiovascular diseases or pathological conditions described here.

As used herein, "precursor" of a miR-222 sequence include the various sequences corresponding to the pre-miR-222 or the pri-miR-222 sequences of the mature miR-222. The pre-miRNA is the process product of pri-miRNA by Drosha/Pasha, and can be exported from nucleus of the infected cell to the cytoplasm by the RAN-GTPase Exportin 5. Once inside the cytosol, the pre-miRNA may be further bound and processed by another RNase III Dicer to produce a double-stranded complex of miR and its complementary sequence, which miR is subsequently loaded into the miRISC complex, and forms a complex with an Argonaute protein (e.g., AGO2).

In certain embodiments, the precursor may also include sequences (natural or synthetic) not identical to the pre-miR-222 or pri-miR-222, but can nevertheless be similarly processed by the same RNase III.

The sequence of a human miR-222 precursor is:

GCUGCUGGAAGGUGUAGGUACCCUCAAUGGCUCAGUAGCCAGUGUAGAUC

CUGUCUUUCGUAAUCAGCAGCUACAUCUGGCUACUGGGUCUCUGAUGGCA

UCUUCUAGCU (HGNC: 31602; SEQ ID NO: 1).

Its stem loop diagram is shown below:

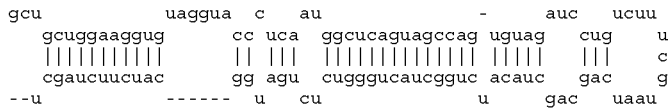

The sequence of the mature human miR-222 is CUCA-GUAGCCAGUGUAGAUCCU (SEQ ID NO: 2; Accession: MIMAT0000279).

The miR-222 sequences are highly conserved throughout evolution. BLAST search using the human miR-222 sequence above as a query retrieved numerous related human and non-human miR-222 sequences. For example, the Macaca mulatta mir-222 sequence NR_032459 is 99% (109/110) identical to the human sequence SEQ ID NO: 1 above; the Equus caballus (horse) microRNA mir-222 NR_033080 is 98% (108/110) identical to the human sequence SEQ ID NO: 1 above; the Bos taurus (cattle) microRNA mir-222 NR_030882 is 97% (107/110) identical to the human sequence SEQ ID NO: 1 above; the Rattus norvegicus (rat) microRNA 222 NR_031935 is 96% (90/94) identical to nucleotides 17-110 of the human sequence SEQ ID NO: 1 above; and the Mus musculus (mouse) microRNA-222 NR_029807 is 96% (76/79) identical to nucleotides 21-99 of the human sequence SEQ ID NO: 1 above.

In certain embodiments, the miR-222 or precursor is a human sequence.

In certain embodiments, the miR-222 or precursor is a mammalian sequence, such as a non-human primate sequence.

In certain embodiments, the subject agent is a miR-222 precursor, such as a pri- or pre-miR-222, or a sequence comprising SEQ ID NO: 1.

In certain embodiments, the subject agent is a miR-222 mimic or pri-miR-222 or pre-miR-222 mimic, such as a modified pri-miR-222 or pre-miR-222 containing one or more modified nucleic acid that enhances serum stability, cellular in-take, and/or nuclease resistance, and/or reduces the host immune or inflammatory response.

3. The Subject Polypeptide

In certain embodiments, the invention provides methods of using a subject CITED4 related polypeptide for treating the various cardiovascular diseases or pathological conditions described here.

"CITED4," "CBP/p300-Interacting Transactivator, with Glu/Asp-rich carboxyl terminal Domain, 4," and "CBP/p300-Interacting Transactivator with ED-rich carboxy-terminal Domain 4," are used interchangeably herein to refer to a family of mammalian polypeptides that act as transcriptional coactivator for Transcription Factor AP-2 (TFAP2)/ AP-2; that enhance estrogen-dependent transactivation mediated by estrogen receptors; that may function as an inhibitor of transactivation by HIF1A by disrupting HIF1A interaction with CREB Binding Protein (CREBBP); and that may be involved in regulation of gene expression during development and differentiation of blood cells, endothelial cells and mammary epithelial cells. CITED4 interacts via its conserved C-terminal region with the CH1 domain of CREBBP and EP300, and interacts with all TFAP2/AP-2 isoforms. It is also synonymous with "transcriptional coactivator 4," "MSG-1 related protein 2," or "MRG2."

In certain embodiments, CITED4 represents a 184-a.a. human polypeptide having the following polypeptide sequence:

MADHLMLAEGYRLVQRPPSAAAAHGPHALRTLPPYAGPGLDSGLRPRGAP

LGPPPPRQPGALAYGAFGPPSSFQPFPAVPPPAAGIAHLQPVATPYPGRA

AAPPNAPGGPPGPQPAPSAAAPPPPAHALGGMDAELIDEEALTSLELELG

LHRVRELPELFLGQSEFDCFSDLGSAPPAGSVSC (SEQ ID NO: 3;

Access No. Q96RK1)

Also see the NCBI protein RefSeq NP_597724.1 and nucleotide RefSeq. NM_133467.2.

The CITED4 polypeptide is about 98% identical to its counterpart in Pan troglodytes (Chimpanzee; Access No. H2PYS8 or K7BVD1), including 100% identical in the 61 C-terminal residues; 96% identical to its counterpart in *Macaca mulatta* (Rhesus macaque; Access No. I2CVG1), including 100% identical in 60 of the 61 C-terminal residues; 87% identical to its counterpart in *Bos taurus* (Bovine; Access No. Q2HJ78), including 100% identical in 60 of the 61 C-terminal residues except for a conserved E to D change; 84% identical to its counterpart in *Cavia porcellus* (Guinea pig; Access No. H0W249), including 100% identical in 59 of the 60 C-terminal residues; 77% identical to its counterpart in *Mus musculus* (Mouse; Access No. A2A7E7), including 100% identical in 49 of the 50 C-terminal residues; and 73% identical to its counterpart in *Rattus norvegicus* (Rat; Access No. Q99MA0), including 100% identical in 51 of the 53 C-terminal residues.

Thus in certain embodiments, CITED4 represents a mammalian polypeptide at least about 75%, 80%, 85%, 90%, 95%, 98% identical to SEQ ID NO: 3, such as the above-referenced mammalian CITED4 polypeptides.

In certain embodiments, CITED4 represents a mammalian polypeptide that is a functional fragment of any of the above-referenced mammalian sequences, such as a functional fragment of SEQ ID NO: 3.

In certain embodiments, the functional fragment comprises or consists essentially of or consists of the C-terminal 48, 49, 50, 51, 52, 53, 54, 55, 60, 61, 62, or 63 residues of SEQ ID NO: 3 or its counterpart fragments in any of the mammalian sequences, such as those referenced above.

In certain embodiments, the invention also provides fusion proteins of any of the above functional fragments with a heterologous polypeptide, such as a epitope tag, or any heterologous protein that does not substantially negatively impact the function of the functional fragment.

In certain embodiments, the functional fragment or fusion thereof stimulates cardiomyocyte growth, proliferation, and/or regeneration, to substantially the same extent (e.g., at least about 50%, 60%, 70%, 80%, 90%, 95% or nearly 100% or more efficient/effective) as the wildtype CITED4 polypeptide.

In certain embodiments, the functional fragment or fusion thereof acts as transcriptional coactivator for Transcription Factor AP-2 (TFAP2)/AP-2; enhances estrogen-dependent transactivation mediated by estrogen receptors; functions as an inhibitor of transactivation by HIF1A by disrupting HIF1A interaction with CREB Binding Protein (CREBBP); and/or is involved in regulation of gene expression during development and differentiation of blood cells, endothelial cells and mammary epithelial cells, to substantially the same extent (e.g., at least about 50%, 60%, 70%, 80%, 90%, 95% or nearly 100% or more efficient/effective) as the wildtype CITED4 polypeptide.

In certain embodiments, CITED4 is encoded by a polynucleotide encoding any of the above-referenced mammalian CITED4 polypeptides or functional fragments or fusions thereof. For example, the human CITED4 polypeptide may be encoded by a polynucleotide represented by NCBI nucleotide RefSeq. NM_133467.2.

In certain embodiments, the polynucleotide may be an mRNA (including a synthetic, modified mRNA, such as one described herein), or a DNA. The encoding polynucleotide may be within a suitable vector (such as an AAV vector) that is capable of directing the expression of CITED4 in a suitable mammalian host cell, such as a cardiomyocyte or precursor thereof.

4. Expression Constructs and Uses Thereof

The CITED4 polypeptide or functional fragments or fusions thereof, and the miR-222, a precursor (e.g., pre-miR-222), and mimics of the invention (or "the subject agents") can be expressed in vitro and in vivo from a vector or expression construct.

A "vector" or "expression construct" is used to deliver a nucleic acid of interest (such as a nucleic acid encoding the subject agents) to the target expression site, such as the interior of a cell/cardiomyocytes. Numerous vectors are known in the art, including (but not limited to) linear polynucleotides, polynucleotides associated with ionic or amphiphillic compounds, plasmids, and virus-based vectors. Thus, the term "vector" includes an autonomously replicating plasmid or a virus-based vector. Examples of viral vectors include, but are not limited to, adenoviral vectors, adeno-associated virus (AAV) vectors, retroviral vectors, and the like. A vector or expression construct can be replicated in a living cell, or it can be made synthetically.

In certain embodiments, an expression vector for expressing a subject agent comprises a promoter operably linked to a polynucleotide encoding a sequence of the subject agent (e.g., CITED4 polypeptide or miR-222). "Operably linked" or "under transcriptional control" as used herein means that the promoter is in the correct location and orientation in relation to a polynucleotide to control the initiation of transcription by RNA polymerase (such as RNA Pol II or Pol III), and/or expression of the encoded CITED4.

The polynucleotide encoding miR-222 may encode the primary microRNA sequence, the precursor-microRNA sequence, the mature miRNA sequence, or the star (e.g. minor) sequence of miR-222. The polynucleotide encoding miR-222 can be about 18 to about 2000 nucleotides in length, about 70 to about 200 nucleotides in length, about 20 to about 50 nucleotides in length, or about 18 to about 25 nucleotides in length.

In certain embodiments, the nucleic acid encoding a CITED4 polypeptide or a miR-222 is under transcriptional control of a promoter. A "promoter" refers to a DNA sequence recognized by the transcription machinery of the cell, or introduced transcription machinery, required to initiate the specific transcription of a gene.

In some embodiments, the human cytomegalovirus (CMV) immediate early gene promoter, the SV40 early promoter, the Rous sarcoma virus long terminal repeat, rat insulin promoter, and glyceraldehyde-3-phosphate dehydrogenase promoter can be used to obtain high-level expression of the polynucleotide sequence of interest. The use of other viral or mammalian cellular or bacterial phage promoters, which are well-known in the art to achieve expression of a subject agent of interest, is contemplated as well, provided that the levels of expression are sufficient for a given purpose.

By employing a promoter with well-known properties, the level and pattern of expression of a subject agent of interest following transfection or transformation can be optimized. Further, selection of a promoter that is regulated in response to specific physiologic signals can permit inducible expression of the subject agent. Several exemplary regulatory elements that may be employed, in the context of the present invention, to regulate the expression of the subject agent of interest, may include (but are not limited to): viral promoters, cellular promoters/enhancers and inducible promoters/enhancers that could be used in combination with the subject agent of interest in an expression construct. Additionally, any promoter/enhancer combination (as per the Eukaryotic Promoter Data Base EPDB) could also be used to drive expression of the polynucleotide. Eukaryotic cells can support cytoplasmic transcription from certain bacterial promoters if the appropriate bacterial polymerase is provided, either as part of the delivery complex or as an additional genetic expression construct.

Illustrative promoter and/or enhancer include: Ig heavy chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990); Ig light chain (Queen et al., 1983; Picard et al., 1984); T-Cell Receptor (Luria et al., 1987; Winoto et al., 1989; Redondo et al., 1990); HLA DQ α and/or DQ β (Sullivan et al., 1987); β-Interferon (Goodbourn et al., 1986; Fujita et al., 1987; Goodbourn et al., 1988; Interleukin-2 (Greene et al., 1989); Interleukin-2 Receptor (Greene et al., 1989; Lin et al., 1990); MHC Class II 5 (Koch et al., 1989); MHC Class II (Sherman et al., 1989); HLA-DRa; β-Actin (Kawamoto et al., 1988; Ng et al.; 1989); Muscle Creatine Kinase (MCK) (Jaynes et al., 1988; Horlick et al., 1989; Johnson et al., 1989); Prealbumin (Transthyretin) (Costa et al., 1988); Elastase I (Ornitz et al., 1987); Metallothionein (MTII) (Karin et al., 1987; Culotta et al., 1989); Collagenase (Pinkert et al., 1987; Angel et al., 1987a); Albumin (Pinkert et al., 1987; Tronche et al., 1989, 1990); α-Fetoprotein (Godbout et al., 1988; Campere et al., 1989); t-Globin (Bodine et al., 1987; Perez-Stable et al., 1990); β-Globin (Trudel et al., 1987); c-fos (Cohen et al., 1987); c-HA-ras (Triesman, 1986; Deschamps et al., 1985); Insulin (Edlund et al., 1985); Neural Cell Adhesion Molecule (NCAM) (Hirsh et al., 1990); α$_1$-Antitrypain (Latimer et al., 1990); H2B (TH2B) Histone (Hwang et al., 1990); Mouse and/or Type I Collagen (Ripe et al., 1989); Glucose-Regulated Proteins (GRP94 and GRP78) (Chang et al., 1989); Rat Growth Hormone (Larsen et al., 1986); Human Serum Amyloid A (SAA) (Edbrooke et al., 1989); Troponin I (TN I) (Yutzey et al., 1989); Platelet-Derived Growth Factor (PDGF) (Pech et al., 1989); Duchenne Muscular Dystrophy (Klamut et al., 1990); SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988); Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988); Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989); Papilloma Virus (Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987) Hepatitis B Virus (Bulla et al., 1986; Jameel et al., 1986; Shaul et al., 1987; Spandau et al., 1988; Vannice et al., 1988); Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989); Cytomegalovirus (CMV) (Weber et al., 1984; Boshart et al., 1985; Foecking et al., 1986); Gibbon Ape Leukemia Virus (Holbrook et al., 1987; Quinn et al., 1989).

Inducible Elements include: MT II promoter inducible by Phorbol Ester (TFA) or Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus) promoter inducible by Glucocorticoids (Huang et al., 1981; Lee et al., 1981; Majors et al., 1983; Chandler et al., 1983; Ponta et al., 1985; Sakai et al., 1988); β-Interferon promoter inducible by poly(rI)x or poly(rc) (Tavernier et al., 1983); Adenovirus 5 E2 promoter inducible by E1A (Imperiale et al., 1984); Collagenase promoter inducible by Phorbol Ester (TPA) (Angel et al., 1987a); Stromelysin promoter inducible by Phorbol Ester (TPA) (Angel et al., 1987b); SV40 promoter inducible by Phorbol Ester (TPA) (Angel et al., 1987b); Murine MX Gene promoter inducible by Interferon or Newcastle Disease Virus (Hug et al., 1988); GRP78 Gene promoter inducible by A23187 (Resendez et al., 1988); α-2-Macroglobulin promoter inducible by IL-6 (Kunz et al., 1989), Vimentin promoter inducible by Serum (Rittling et al., 1989); MHC Class I Gene H-2κb promoter inducible by Interferon (Blanar et al., 1989); HSP70 promoter inducible by EIA or SV40 Large T Antigen (Taylor et al., 1989, 1990a, 1990b); Proliferin promoter inducible by Phorbol Ester-TPA (Mordacq et al., 1989); Tumor Necrosis Factor PMA (Hensel et al., 1989); Thyroid Stimulating Hormone α Gene promoter inducible by Thyroid Hormone (Chatterjee et al., 1989).

In certain embodiments, the inducible promoter is a tetracyclin-inducible promoter, in a tetracycline-controlled transcriptional activation system/construct, which is a method of inducible gene expression where transcription is reversibly turned on or off in the presence of the antibiotic tetracycline or one of its derivatives (e.g. doxycycline or Dox, a more stable tetracycline analogue).

The two most commonly used inducible expression systems for research of eukaryote cell biology are Tet-Off and Tet-On. The Tet-Off system activates expression in the absence of Dox (Bujard et al., *Proc. Natl. Acad. Sci. U.S.A.* 89 (12):5547-5551, 1992), whereas the Tet-On system activates expression in the presence of Dox.

The Tet-Off system employs the tetracycline transactivator (tTA) protein, which is a fusion protein of the *E. coli* TetR (tetracycline repressor) and the activation domain of HSV transcription factor VP16. The resulting tTA protein is able to bind to DNA at specific TetO operator sequences. In most Tet-Off systems, several repeats of such TetO sequences are placed upstream of a minimal promoter such as the CMV promoter. The entirety of several TetO sequences with a minimal promoter is known as tetracycline response element (TRE), because it responds to binding of the tetracycline transactivator protein tTA by increased expression of the gene or genes downstream of its promoter.

In a Tet-Off system, expression of TRE-controlled genes can be repressed by tetracycline and its derivatives such as Dox. They bind tTA and render it incapable of binding to TRE sequences, thereby preventing transactivation of TRE-controlled genes.

A Tet-On system works similar, but in the opposite fashion. While in a Tet-Off system, tTA is capable of binding the operator only if not bound to tetracycline or one of its derivatives, such as doxycycline, in a Tet-On system, the tTA protein is capable of binding the operator only if bound by a tetracycline. Thus the introduction of doxycycline to the system initiates the transcription of the genetic product. The Tet-On system is sometimes preferred over Tet-Off for its faster responsiveness.

The Tet-On Advanced transactivator (also known as rtTA2$^S$-M2) is an alternative version of Tet-On that shows reduced basal expression, and functions at a 10-fold lower Dox concentration than Tet-On. In addition, its expression is considered to be more stable in eukaryotic cells due to being human codon optimized and utilizing 3 minimal transcriptional activation domains. It was discovered as one of two improved mutants after random mutagenesis of the Tet Repressor part of the transactivator gene (Urlinger et al., *Proc. Natl. Acad. Sci. U.S.A.* 97 (14):7963-7968, 2000).

Tet-On 3G (also known as rtTA-V10) is similar to Tet-On Advanced because they were derived from the same predecessor. It is also human codon optimized and composed of 3 minimal VP16 activation domains. However, the Tet-On 3G protein has 5 amino acid differences compared to Tet-On Advanced which appear to increase its sensitivity to Dox even further. Tet-On 3G is sensitive to 100-fold less Dox than the original Tet-On (Zhou et al., *Gene Ther.* 13 (19): 1382-1390, 2006).

The Tet-Off and Tet-On expression systems can both be used in generating transgenic mice, which conditionally express gene of interest. In certain embodiments, the Tet-On system (including Tet-On Advanced transactivator and Tet-On 3G) is used with the methods and constructs of the invention. In certain embodiments, the Tet-Off system is used with the methods and constructs of the invention.

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin I promoter (Bhaysar et al., 1996); the Na$^+$/Ca$^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

Complete citations for the references cited herein can be found in US 2012-0165392 A1, which is incorporated herein by reference.

A polyadenylation signal may be included to effect proper polyadenylation of the gene transcript where desired. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with or as an indicator of the nucleic acid encoding a gene product. Further examples of selectable markers are well known to one of skill in the art.

There are a number of ways in which expression vectors may be introduced into cells.

According to Ginn et al. (*J. Gene Med.,* 15:65-77, 2013), since the first report of successful treatment of a genetic disease by gene therapy in 2000, over 1800 gene therapy clinical trials have been completed, are ongoing or have been approved worldwide in 31 countries as of mid-2012. Long term follow up of the initial trial has established gene therapy as a realistic therapeutic alternative for patients without a suitably matched sibling donor, which is associated with less favorable survival rates. Among the diseases in clinical trial using gene therapy, the vast majority (81.5%) to date have addressed cancer, cardiovascular disease, and inherited monogenic diseases. Cardiovascular gene therapy is currently the third most popular application for gene therapy behind cancer and the collection of inherited monogenic diseases, and provides a new avenue for host of therapeutic uses including therapeutic angiogenesis, myocardial protection, regeneration and repair, prevention of restenosis following angioplasty, prevention of bypass graft failure and risk-factor management.

A variety of difference vectors and delivery techniques have been applied in these gene therapy trials. Although nonviral approaches are becoming increasingly common, viral vectors remain by far the most popular approach, having been used in approximately two-thirds of the trials performed to date. The most popular viral vector used in clinical trials is adenoviral vector (23.3% of all trials), followed closely by retroviral vector (about 20% of all trials). Although adenoviral vector can carry a larger DNA load than retroviruses, the main advantages of adenoviral vectors are their abilities to achieve a high efficiency of transduction, high levels of gene expression (though transient), and to infect nondividing cells. Other viruses have been less widely used and include vaccinia virus (7.9% of trials), poxvirus (5.0%), adeno-associated virus (4.9%), and herpes simplex virus (3.1%). The use of these vectors has increased significantly in recent years as alternatives to retroviruses. Many trials also combined two vectors, such as poxvirus and vaccinia virus, adenovirus and retrovirus, adenovirus and vaccinia virus, naked DNA and adenovirus, adenovirus and modified vaccinia Ankara virus, and naked DNA and vaccinia virus. These combinations are within the scope of the invention.

Thus in certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. In certain embodiments, adenovirus type 5 of subgroup C may be used as starting material in order to obtain the conditional replication-defective adenovirus vector for use in the present invention. Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Other viral vectors may be employed as expression constructs in the present invention. Vectors derived from viruses such as retrovirus, vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of the subject agents encoded by the expression constructs, the expression constructs must be delivered into a target cell, such as a cardiomyocyte. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Synthetic vectors not based on viral systems can also be used in the methods of the invention. The simplest nonviral gene delivery system uses "naked" DNA, which, when injected directly into certain tissues, particularly muscle, produces significant levels of gene expression, although lower than those achieved with viral vectors. Naked DNA has been used in about 18.3% of the clinical trial by 2012, and it is the most popular nonviral system used in clinical trials. Lipofection, the second most used non-viral delivery in clinical trials (used in 5.9% of all trials), involves cationic lipid/DNA complexes. A small number of trials have also used a range of modified bacteria (20 trials) or brewer's yeast strains (seven trials). These methods can also be used in the methods of the invention to deliver a subject agent or a coding nucleic acid.

Thus several non-viral methods for the transfer of expression constructs into cultured mammalian cells also are contemplated by the present invention. These include naked DNA encoding a subject agent, calcium phosphate precipitation (Graham and Van Der Eb, 1973; Chen and Okayama, 1987; Rippe et al., 1990), DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), and lipofection or lipofectamine-DNA complexes, cell sonication (Fechheimer et al., 1987), gene bombardment using high velocity microprojectiles (Yang et al., 1990), receptor-mediated transfection (Wu and Wu, 1987; Wu and Wu, 1988), and bacteria or yeast mediated delivery. Some of these techniques may be successfully adapted for in vivo or ex vivo use.

Once the expression construct has been delivered into the cell the nucleic acid encoding the subject agents may be positioned and expressed at different sites. In certain embodiments, the nucleic acid encoding the subject agents may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes"

encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a polynucleotide of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular polynucleotide of interest may be delivered via this method and still be incorporated by the present invention.

In a further embodiment, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EP 0273085).

In a particular example, the polynucleotide may be administered in combination with a cationic lipid or neutral lipid, or a combination of cationic and anionic lipids that together result in a neutral charge (see e.g. WO 05/007196 and WO 05/026372, which are herein incorporated by reference in their entireties). Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publications 2003/0203865, 2002/0150626, 2003/0032615, and 2004/0048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Preferably, administration of a subject agent (e.g., a CITED4 polypeptide or functional fragment or fusion thereof, or miR-222 or a mimic thereof) results in the improvement of one or more symptoms of the cardiovascular disease or pathological condition (e.g., myocardial infarction, heart failure, or cardiac remodeling).

The one or more improved symptoms can be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, increased quality of life, and decreased disease related morbidity or mortality.

In one embodiment, expression of a subject agent in the heart cells of a subject, such as a subject suffering from myocardial infarction, can reduce infarct size by decreasing the loss of heart cells (e.g., decreasing apoptosis in the infarct zone).

In another embodiment, expression of a subject agent in the heart cells of a subject, such as a subject suffering from myocardial infarction, can reduce fibrosis in the infarct zone.

In another embodiment, expression of a subject agent in the heart cells of a subject, such as a subject suffering from myocardial infarction, can stabilize cardiac function.

5. Sustained Polypeptide Expression from Synthetic, Modified RNAs

In certain embodiments, the subject polypeptide (e.g., CITED4 or functional fragments or fusions thereof) may be expressed using synthetic, modified RNA as described in US 2012-0046346 A1 and US 2014-0186432 A1 (incorporated herein by reference), which described in detail compositions, methods, and kits comprising synthetic, modified RNAs for changing the phenotype of a cell or cells, by expressing a desired polypeptide (e.g., CITED4 or functional fragments or fusions thereof) in a target cell or tissue or in vivo.

The disclosed methods, compositions, and kits do not utilize exogenous DNA or viral vector-based methods for the expression of protein(s), and thus, do not cause permanent modification of the genome or have the potential for unintended mutagenic effects. However, such synthetic, modified RNAs are included within the scope of the term "expression construct" as it is used in the instant application.

Specifically, the compositions, methods, and kits described herein are based upon the direct introduction of the synthetic, modified RNAs into a cell, which translated the RNA into a desired polypeptide. In the methods described herein, the effect of the cellular innate immune response is mitigated by using synthetic RNAs that are modified in a manner that avoids or reduces the response. Avoidance or reduction of the innate immune response permit sustained expression from exogenously introduced RNA. In certain embodiments, sustained expression of the subject polypeptide (e.g., CITED4 or functional fragments or fusions thereof) is achieved by repeated introduction of synthetic, modified RNAs into a target cell or its progeny, preferably in vivo.

The modified, synthetic RNAs can be introduced to a cell in order to induce exogenous expression of the subject polypeptide. The ability to direct exogenous expression of the subject polypeptide using the modified, synthetic RNAs described herein is useful, for example, in the treatment of disease or disorders caused by an endogenous defect in a cell or organism that impairs or prevents the ability of that cell or organism to produce the subject polypeptide (e.g., a subject unable to produce, or unable to produce sufficient quantities of, the subject polypeptide, either as a result of genetic defect, or as a result of injury). Accordingly, in some embodiments, compositions and methods comprising the modified, synthetic RNAs described herein can be used for the purposes of gene therapy.

In some embodiments, the synthetic, modified RNA molecule comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In some embodiments, the at least two modified nucleosides are 5-methylcytidine (5mC) and pseudouridine.

In certain embodiments, the synthetic, modified RNA molecule further comprises a 5' cap. In one such embodiment, the 5' cap is a 5' cap analog. In one embodiment, the 5' cap analog is a 5' diguanosine cap.

In certain embodiments, the synthetic, modified RNA molecule does not comprise a 5' triphosphate.

In certain embodiments, the synthetic, modified RNA molecule further comprises a poly(A) tail, a Kozak sequence, a 3' untranslated region, a 5' untranslated region, or any combination thereof. In one embodiment, the poly(A) tail, the Kozak sequence, the 3' untranslated region, the 5' untranslated region, or the any combination thereof comprises one or more modified nucleosides.

In certain embodiments, the synthetic, modified RNA molecule is further treated with an alkaline phosphatase.

In certain embodiments, the innate immune response comprises expression of a Type I or Type II interferon. In certain embodiments, the innate immune response comprises expression of one or more IFN signature genes selected from the group consisting of IFNα, IFNB1, IFIT, OAS1, PKR, RIGI, CCL5, RAP1A, CXCL10, IFIT1, CXCL11, MX1, RP11-167P23.2, HERC5, GALR3, IFIT3, IFIT2, RSAD2, and CDC20.

In one aspect, provided herein is a cell (such as a cardiomyocyte or precursor or progeny thereof) contacted with a synthetic, modified RNA molecule encoding a subject polypeptide, where the synthetic, modified RNA molecule comprises one or more modifications, such that introducing the synthetic, modified RNA molecule to the cell results in a reduced innate immune response relative to the cell contacted with a synthetic RNA molecule encoding the polypeptide not comprising the one or more modifications.

In certain embodiments, the synthetic, modified RNA molecule contacted with the cell comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In certain embodiments, the at least two modified nucleosides are 5-methylcytidine (5mC) and pseudouridine.

In certain embodiments, the synthetic, modified RNA molecule contacted with the cell further comprises a 5' cap. In one such embodiment, the 5' cap is a 5' cap analog. In one embodiment, the 5' cap analog is a 5' diguanosine cap. In certain embodiments, the synthetic, modified RNA molecule contacted with the cell does not comprise a 5' triphosphate. In certain embodiments, the synthetic, modified RNA molecule contacted with the cell further comprises a poly(A) tail, a Kozak sequence, a 3' untranslated region, a 5' untranslated region, or any combination thereof. In one embodiment, the poly(A) tail, the Kozak sequence, the 3' untranslated region, the 5' untranslated region, or the any combination thereof comprises one or more modified nucleosides. In certain embodiments, the synthetic, modified RNA molecule contacted with the cell is further treated with an alkaline phosphatase.

In certain embodiments, the synthetic, modified RNA molecule comprises a coding region (e.g., a coding region for CITED4), said coding region having an altered G/C content as compared to the G/C content of the coding region comprising nucleotides 220-774 of SEQ ID NO: 275 of US 2014-0186432 A1. For example, the coding region which has an altered G/C content may be selected from the group of nucleic acid sequences consisting of SEQ ID NO: 1421, 1794, 2414, 3034, 3654, 4274, and 8408-8494 of US 2014-0186432 A1.

In certain embodiments, the G/C content in the coding region is decreased as compared to the G/C content in the coding region of SEQ ID NO: 275 of US 2014-0186432 A1. For example, the coding region with a decreased G/C content may be selected from the group consisting of SEQ ID NO: 2414, 3034, 3654, 4274, and 8408-8494 of of US 2014-0186432 A1.

In certain embodiments, the G/C content in the coding region is the same as compared to the G/C content in the coding region of SEQ ID NO: 275 of of US 2014-0186432 A1. For example, the coding region with the same G/C content may be SEQ ID NO: 1794 of of US 2014-0186432 A1.

In certain embodiments, the nucleic acid comprises at least one untranslated region 5' relative to the coding region and at least one untranslated region 3' relative to the coding region. For example, the 5' untranslated region may be heterologous to the coding region of the nucleic acid, and/or the 3' untranslated region may be heterologous to the coding region of the nucleic acid. In certain embodiments, the 5' untranslated region and the 3' untranslated region are heterologous to the coding region of the nucleic acid. In certain embodiments, the nucleic acid comprises at least two stop codons.

In certain embodiments, the nucleic acid encods SEQ ID NO: 890 of of US 2014-0186432 A1, wherein said nucleic acid comprises a coding region, said coding region having an altered G/C content as compared to the G/C content of the coding region comprising nucleotides 220-774 of SEQ ID NO: 275 of US 2014-0186432 A1.

In certain embodiments, the innate immune response comprises expression of a Type I or Type II interferon, and the expression of the Type I or Type II interferon is not increased more than three-fold compared to a reference from a cell which has not been contacted with the synthetic modified RNA molecule. In certain embodiments, the innate immune response comprises expression of one or more IFN signature genes selected from the group consisting of IFNα, IFNB1, IFIT, OAS1, PKR, RIGI, CCL5, RAP1A, CXCL10, IFIT1, CXCL11, MX1, RP11-167P23.2, HERC5, GALR3, IFIT3, IFIT2, RSAD2, and CDC20, and where the expression of the one of more IFN signature genes is not increased more than six-fold compared to a reference from a cell which has not been contacted with the synthetic modified RNA molecule.

In certain embodiments, the polypeptide encoded by the synthetic, modified RNA molecule introduced to the cell alters a function or a developmental phenotype of the cell. In some such embodiments, the developmental phenotype is a developmental potential. In some embodiments, the developmental potential is decreased. In some embodiments, the developmental potential is increased. In certain embodiments, the polypeptide encoded by the synthetic, modified RNA molecule introduced to the cell promotes the growth, proliferation, and/or regeneration of cardiomyocytes, or a precursor or progeny thereof. In certain embodiments, the polypeptide encoded by the synthetic, modified RNA molecule is a transcription factor, or function as a transcription factor.

In certain embodiments, the cell is a human cell. In other embodiments, the cell is not a human cell. In certain embodiments, the cell is an adult cell. In certain embodiments, the cell is not aneonatal cell (e.g., neonatal carbiomyocyte).

In certain embodiments, the cell or its immediate precursor cell(s) has been subjected to at least 3 separate rounds of contacting with the exogenously introduced modified synthetic RNA encoding the subject polypeptide.

In certain embodiments, the cell has a reduced expression of a Type I or Type II IFN relative to a cell subjected to at least 3 separate rounds of contacting with an exogenously introduced non-modified, synthetic RNA encoding the subject polypeptide. In certain embodiments, the cell has a reduced expression of at least one IFN-signature gene relative to a cell subjected to at least 3 separate rounds of contacting with an exogenously introduced non-modified synthetic RNA encoding the subject polypeptide. In certain embodiments, the IFN-signature gene is selected from the group consisting of IFNα, IFNB1, IFIT, OAS1, PKR, RIGI, CCL5, RAP1A, CXCL10, IFIT1, CXCL11, MX1, RP11-167P23.2, HERC5, GALR3, IFIT3, IFIT2, RSAD2, and CDC20.

In another aspect, provided herein is a composition comprising at least one modified, synthetic RNA encoding a subject polypeptide, and cell growth media.

In certain embodiments, contacting of the cell population or progeny cells thereof is performed in vitro, ex vivo, or in vivo.

Other aspects described herein provide methods of treating subjects in need of cellular therapies. In such aspects, an effective amount of a population of any of the progenitor, multipotent, oligopotent, lineage-restricted, fully or partially differentiated cells, generated using any of the compositions or methods comprising synthetic, modified RNAs described herein, is administered to a subject in need of a cellular therapy.

Accordingly, in one aspect, provided herein is a method of treating a subject in need of a cellular therapy, comprising: administering to a subject in need of a cellular therapy an effective amount of a population of cells (e.g., cardiomyocytes) produced by contacting a cell population or progeny cells thereof with at least one synthetic, modified RNA encoding a subject polypeptide (preferably for at least three consecutive times).

In some embodiments, the method further comprises a step of obtaining an autologous cell from the subject and generating a population of cardiomyocytes from the autologous cell by contacting the cell population or progeny cells thereof with at least one synthetic, modified RNA encoding a subject polypeptide (preferably for at least three consecutive times).

Also provided herein are kits comprising: a) a container with at least one synthetic, modified RNA molecule comprising at least two modified nucleosides and encoding a subject polypeptide, and b) packaging and instructions therefor. In certain embodiments, the kit further comprises a container with cell culture medium. In certain embodiments, the kit further comprises an IFN inhibitor. In some embodiments, the kit further comprises valproic acid.

In some embodiments, the kit further comprises a non-implantable delivery device or an implantable delivery device to deliver the at least one synthetic, modified RNA. In some such embodiments, the non-implantable delivery device is a pen device. In some such embodiments, the implantable delivery device is a pump, semi-permanent stent, or reservoir.

6. Treatable Diseases

In certain embodiments, the invention provides methods of using a subject miR-222 microRNA or a precursor (e.g., pre-miR-222) or mimic thereof, or a CITED4 polypeptide or functional fragments or fusions thereof, for treating various cardiovascular diseases or pathological conditions described herein.

In some embodiments, the cardiovascular disease or pathological condition is myocardial infarction or ischemic injury; adverse remodeling after ischemic injury or infarction; myocarditis; heart failure (congestive); cardiomyopathies, such as ischemic cardiomyopathy, dilated cardiomyopathy, restrictive cardiomyopathy, alcoholic cardiomyopathy, viral cardiomyopathy, tachycardia-mediated cardiomyopathy, stress-induced (takotsubo) cardiomyopathy, amyloid cardiomyopathy, arrhythmogenic right ventricular dysplasia, or unclassified cardiomyopathies, for example left ventricular noncompaction or endocardial fibroelastosis; or valvular heart disease, such as aortic stenosis, aortic regurgitation, mitral stenosis, mitral regurgitation, mitral prolapse, pulmonary stenosis, pulmonary regurgitation, tricuspid stenosis, or tricuspid regurgitation.

In certain embodiments, the cardiovascular disease or pathological condition is ischemic injury, such as one due to myocardial infarction, and/or fibrosis resulting therefrom.

In certain embodiments, the cardiovascular disease or pathological condition is in an individual currently having, have had in the past, or is at risk of having such cardiovascular disease or pathological condition. The individual, also referred to as a subject, may be a mammalian species, including but not limited to a dog, cat, horse, cow, pig, sheep, goat, chicken, rodent (including an experimental animal such as a mouse or rat), or primate, such as a human or a non-human primate. Subjects can be house pets (e.g., dogs, cats), agricultural stock animals (e.g., cows, horses, pigs, chickens, etc.), laboratory animals (e.g., mice, rats, rabbits, etc.), zoo animals (e.g., lions, giraffes, etc.), but are not so limited. Preferred subjects are human subjects (individuals).

The human subject may be a pediatric, adult or a geriatric subject. In certain embodiments, an "adult" patient include any individual that is not considered a newborn or neonatal individual (e.g., a human at least 1 year-old, 2-year old, 3-year old, 5-year old, 10-year old, 15-year old, 20-year old or older). In certain embodiments, however, an "adult" patient refers to a human at least about 15-year old, or at least about 18-year old.

7. Combination Therapy

The present invention contemplates the treatment and prevention of, among other things, post-MI remodeling of cardiac tissues that surround an infarct as well as the subsequent development of heart failure in a subject. Treatment regimens would vary depending on the clinical situation, with earliest intervention being sought. However, long-term maintenance for at least some period of time post-MI would appear to be appropriate in most circumstances. It also may be desirable to treat with the subject agent intermittently, or to vary which of the subject agent is given, in order to maximize the protective effects.

In certain embodiment, it is envisioned that one or more of the subject agent can be used in combination with other therapeutic modalities, such as those more "standard" pharmaceutical cardiac therapies. Examples of other therapies include, without limitation, so-called "β-blockers," mineralocorticoid antagonists, anti-hypertensives, cardiotonics, antithrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and/or HDAC inhibitors.

Combinations may be achieved by contacting cardiac cells with a single composition or a pharmacological formulation that includes one or more of the subject agents and a second cardiac therapy, or by contacting the cell with two distinct compositions or formulations, at the same time, wherein one composition includes one or more of the subject agents and the other includes the second cardiac therapy.

Alternatively, administration of one or more of the subject agents may precede or follow administration of the other cardiac agent(s) by intervals ranging from minutes to weeks. In embodiments where the other cardiac agent and the subject agents are applied separately to the subject, one would generally ensure that a significant period of time did not expire between the time of each delivery, such that the cardiac agent and the subject agents would still be able to exert an advantageously combined effect on the cell. In such instances, it is contemplated that one would typically administer the two compositions within about 12-24 hours of each other and, more preferably, within about 6-12 hours of each other, with a delay time of, for example, about 12 hours etc. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a subject agent, or the other cardiac agent will be desired. In this regard, various combinations may be employed.

Pharmacological therapeutic agents and methods of administration, dosages, etc., are well known to those of skill in the art (see for example, the *Physicians Desk Reference*, Klaassen's *The Pharmacological Basis of Therapeutics, Remington's Pharmaceutical Sciences*, and *The Merck Index*, Eleventh Edition, incorporated herein by reference in relevant parts), and may be combined with the invention in light of the disclosures herein. Some variation in dosage will necessarily occur depending on the condition of the subject being treated. The person responsible for administration to any individual patient will, in any event, determine the appropriate dose for that individual subject, and such individual determinations are within the skill of those of ordinary skill in the art.

Non-limiting examples of a pharmacological therapeutic agent that may be used in combination with the miRNA modulators of the present invention include an antihyperlipoproteinemic agent, an antiarteriosclerotic agent, an anti-thrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues.

In certain embodiments, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof. Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate. Non-limiting examples of resins/bile acid sequesterants include cholestyramine (cholybar, questran), colestipol (colestid) and polidexide. Non-limiting examples of HMG CoA reductase inhibitors include lovastatin (mevacor), pravastatin (pravochol) or simvastatin (zocor). Non-limiting examples of nicotinic acid derivatives include nicotinate, acepimox, niceritrol, nicoclonate, nicomol and oxiniacic acid. Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin. A non-limiting example of an antiarteriosclerotic includes pyridinol carbamate.

In certain embodiments, administration of an agent that aids in the removal or prevention of blood clots may be combined with administration of a miRNA modulator, particularly in treatment of atherosclerosis and vasculature (e.g., arterial) blockages. Non-limiting examples of anti-thrombotic and/or fibrinolytic agents include anticoagulants, anticoagulant antagonists, antiplatelet agents, thrombolytic agents, thrombolytic agent antagonists or combinations thereof. In certain embodiments, antithrombotic agents that can be administered orally, such as, for example, aspirin and warfarin (Coumadin).

In some embodiments, the subject agent can be combined with one or more anticoagulants. Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

The subject agent can also be combined with an antiplatelet agent and/or a thromobolytic agent. Non-limiting examples of antiplatelet agents include aspirin, a dextran, dipyridamole (persantin), heparin, sulfinpyranone (anturane) and ticlopidine (ticlid). Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemorrhage or an increased likelihood of hemorrhaging, an agent that may enhance blood coagulation may be used in combination with a miRNA modulator. Non-limiting examples of blood coagulation promoting agents include thrombolytic agent antagonists and anticoagulant antagonists. Non-limiting examples of anticoagulant antagonists include protamine and vitamin K1.

Non-limiting examples of thrombolytic agent antagonists that can be combined with a miRNA modulator include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

In certain embodiments, a subject agent can be combined with an antiarrhythmic agent for the treatment of cardiovascular conditions. Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Sodium channel blockers include, but are not limited to, Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Exemplary beta blockers, otherwise known as a β-adrenergic blockers, β-adrenergic antagonists or Class II antiarrhythmic agents, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Examples of Class III antiarrhythmic agents include agents that prolong repolarization, such as amiodarone (cordarone) and sotalol (β-pace). Non-limiting examples of Class IV antiarrythmic agents, also known as calcium channel blockers, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Suitable examples of miscellaneous antiarrhythmic agents that can also be combined with a subject agent include, but are not limited to, adenosine (adenocard), digoxin (lanoxin), acecamide, ajmaline, amoproxan, aprindine, bretylium tosylate, bunaftine, butobendine, capobenic acid, cifenline, disopyramide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

In yet another embodiment of the invention, the subject agent can be administered in combination with an antihypertensive agent. Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an alpha and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotensin II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherally acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (naimodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator) that can be co-administered with a miRNA modulator of the invention. In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrate, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethizide, methyclothiazide, meticrane, metolazone, paraflutizide, polythizide, tetrachlomethiazide and trichlormethiazide. Non-limiting examples of N-carboxyalkyl (peptide/lactam) derivatives include alacepril, captopril, cilazapril, delapril, enalapril, enalaprilat, fosinopril, lisinopril, moveltipril, perindopril, quinapril and ramipril. Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

In another embodiment, a subject agent can be co-administered with a vasopressor. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

In certain embodiments, a subject agent can be administered in combination with a treatment for congestive heart failure. Exemplary agents for the treatment of congestive heart failure include, but are not limited to, anti-angiotensin II agents, afterload-preload reduction treatment, diuretics and inotropic agents. Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

In certain embodiments, an animal patient that can not tolerate an angiotensin antagonist may be treated with a combination therapy, such as administration of hydralazine (apresoline) and isosorbide dinitrate (isordil, sorbitrate) with a subject agent.

A subject agent can also be combined with an inotropic agent. In some embodiments, the inotropic agent is a positive inotropic agent. Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an inotropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

In certain embodiments, a subject agent is co-administered with endothelin for treatment of a cardiovascular disease. Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

In certain embodiments, the secondary therapeutic agent that can be combined with the subject agent may comprise a surgery of some type, which includes, for example, preventative, diagnostic or staging, curative and palliative surgery. Surgery, and in particular a curative surgery, may be used in conjunction with other therapies, such as the subject agent of the invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

8. Pharmaceutical Compositions and Formulations

Where clinical applications are contemplated, pharmaceutical compositions comprising a subject agent will be prepared in a form appropriate for the intended application. Generally, this will entail preparing compositions that are essentially free of pyrogens, as well as other impurities that could be harmful to humans or animals. Colloidal dispersion systems, such as macromolecule complexes, nanocapsules, microspheres, beads, and lipid-based systems including oil-in-water emulsions, micelles, mixed micelles, and liposomes, may be used as delivery vehicles for the subject agents. Commercially available fat emulsions that are suitable for delivering the nucleic acids of the invention to tissues, such as cardiac muscle tissue, include INTRALIPID®, LIPOSYN®, LIPOSYN® II, LIPOSYN® III, Nutrilipid, and other similar lipid emulsions. An exemplary colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render nucleic acids, agonists, inhibitors, and delivery vectors stable and allow for uptake by target cells. Buffers also will be employed when recombinant cells are introduced into a patient. Aqueous compositions of the present invention comprise an effective amount of the agent, dissolved or dispersed in a pharmaceutically acceptable carrier or aqueous medium. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or nucleic acids of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising the subject agents may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, *Remington's Pharmaceutical Sciences* 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

An effective amount, also referred to as a therapeutically effective amount, of a subject agent or pharmaceutical composition thereof, is an amount sufficient to ameliorate at least one symptom associated with the cardiovascular disease or pathological condition. The therapeutically effective amount to be included in pharmaceutical compositions may depend, in each case, upon several factors, e.g., the type, size and condition of the patient to be treated, the intended mode of administration, the capacity of the patient to incorporate the intended dosage form, etc. One of ordinary skill in the art would be able to determine empirically an appropriate therapeutically effective amount.

While it is possible for the agents to be administered as the raw substances, it is preferable, in view of their potency, to present them as a pharmaceutical formulation. The formulations of the present invention for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof or deleterious to the inhibitory function of the active agent. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier, which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents, which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multidose containers.

Buffers may also be included to provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

The administration of the pharmaceutical composition or formulation to a patient can be intravenous, intraarterial, intraperitoneal, intramuscular, subcutaneous, intrapleural, intrathecal, by perfusion through a regional catheter, or by direct intralesional injection. When administering by injection, for example, the administration may be by continuous infusion, or by single or multiple boluses. The dosage may vary depending upon such factors as the patient's age, weight, gender, general medical condition, and previous medical history.

In some embodiments, it may be desirable to target delivery to the heart, while limiting delivery of the therapeutic to other organs. This may be accomplished by any one of a number of methods known in the art. In one embodiment delivery to the heart of a pharmaceutical formulation described herein comprises coronary artery infusion. In certain embodiments coronary artery infusion involves inserting a catheter through the femoral artery and passing the catheter through the aorta to the beginning of the coronary artery. In yet another embodiment, targeted delivery of a therapeutic to the heart involves using antibody-protamine fusion proteins, such as those previously describe (Song E. et al., *Nature Biotechnology*, 23(6):709-717, 2005).

EXAMPLES

The invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

Example 1 Forced Expression of CITED4 In Vitro in Adult Cardiomyocytes Fails to Stimulate Cardiomyocyte Proliferation Applicant has previously reported that CITED4 is increased in exercised hearts, and demonstrated that CITED4 drives proliferation of neonatal cardiomyocytes in vitro (Bostrom et al., *Cell*, 143:1072-1083, 2010, see FIG. 1).

However, it is well-known in the art that neonatal cardiomyocytes have a well-recognized capacity for cell division in contrast to the inability of adult cardiomyocytes to proliferate. Thus it is unclear if increasing the expression of CITED4 in adult cardiomyocytes can similarly induce proliferation.

To this end, Applicant has assessed the ability of CITED4 expression to induce proliferation in adult cardiomyocytes. When using an adenoviral gene transfer expression system similar to that used in FIG. 1, forced expression of CITED4 in adult cardiomyocytes resulted in comparable levels of CITED4 expression to that seen in neonatal cardiomyocytes. Surprisingly, however, Applicant was unable to demonstrate markers of cell proliferation in >500 adult cardiomyocytes examined in vitro.

Example 2 Forced Expression of CITED4 In Vivo in Adult Cardiomyocytes Stimulates Cardiomyocyte Proliferation Despite the discouraging results in Example 1, Applicant tested the ability of CITED4 to induce cardiomyocyte proliferation in vivo, by using regulated, controllable expression of CITED4 in a bigenic transgenic system.

Specifically, cDNA encoding the full length mouse CITED4 polypeptide was inserted into a cardiomyocyte-specific expression vector which utilizes an attenuated myosin heavy chain promoter (as previously described in Sanbe et al., "Reengineering inducible cardiac-specific transgenesis with an attenuated myosin heavy chain promoter," Circ. Res. 92 (6):609-616, 2003, incorporated herein by reference), from which the expression of the mature full length CITED4 polypeptide is controlled through expression of a tetracyclin-regulated transcription factor (cf above reference). Transgenic mouse harboring the expression construct was created according to oocyte injection using standard protocols. Expression of the CITED4 polypeptide can be induced by withdrawing tetracycline or doxycycline from the drinking water or food of the transgenic animal, or can be turned off by restoring the tetracycline or doxycycline-containing water or chow. There is virtually no exogenous CITED4 expression in the presence of tetracycline or doxycycline in the chow or drinking water. After inducing expression of the exogenous CITED4, adult cardiomyocyte proliferation can be measured by checking the expression level of biomarkers (such as EdU, phospho-histone H3, ki67, and/or Aurora B kinase in cardiomyocytes identified by virtue of Troponin T expression).

Figure 2:
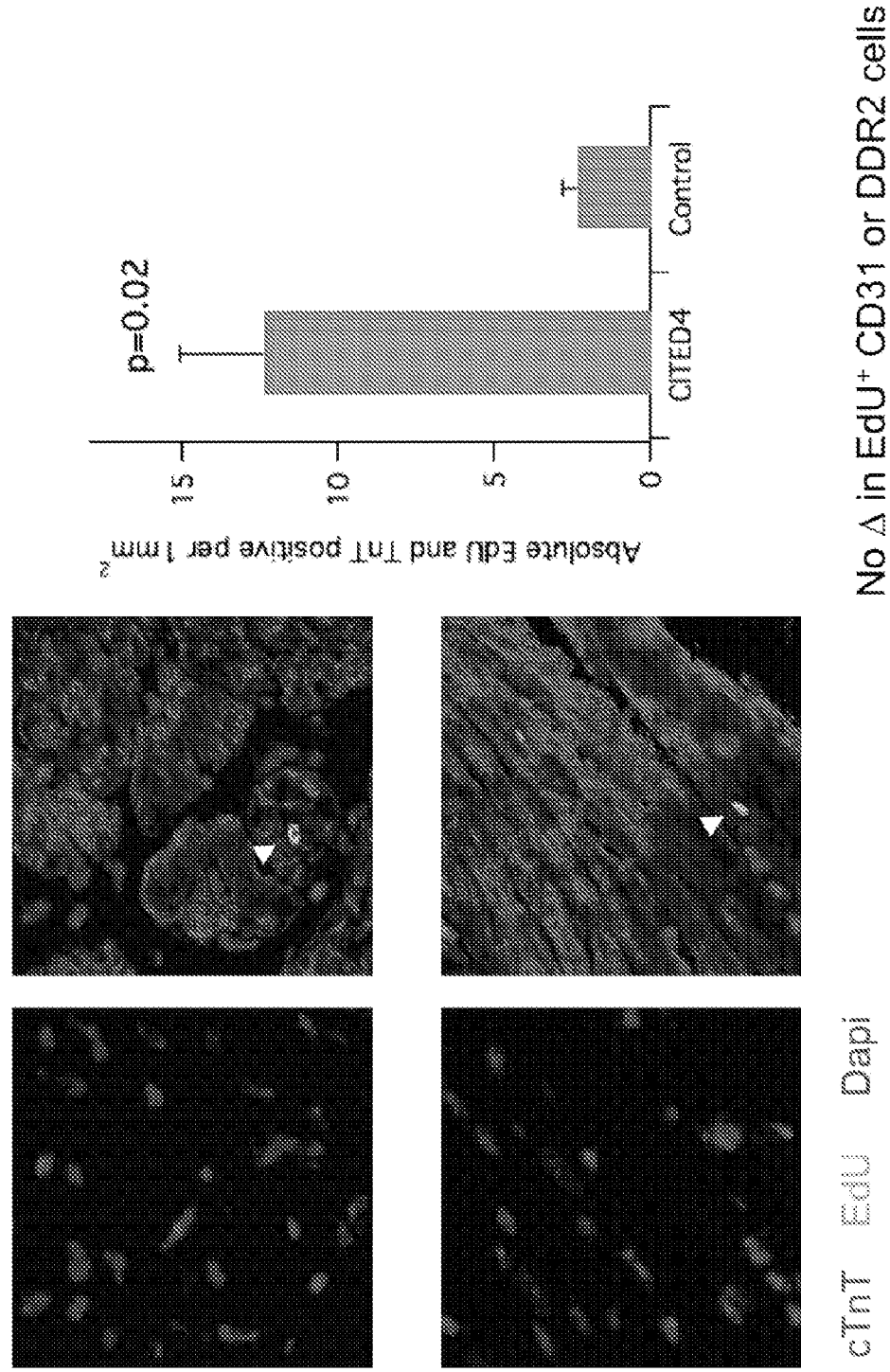
FIG. 2 shows that CITED4 expression induces markers of (adult) cardiomyocyte proliferation in vivo, including the cardiac marker Troponin T (cTnT) and EdU (a thymidine analogue that is incorporated into newly formed DNA). No increase in EdU incorporation was seen in non-cardiomyocyte lineages, including endothelial and fibroblast cells.

Interestingly, and in contrast to our in vitro results with adult cardiomyocytes, induction of CITED4 expression for 3 weeks was sufficient to induce markers of cardiomyocyte proliferation in adult hearts (FIG. 2).

Example 3 Forced EXPRESSION of CITED4 In Vivo in Adult Cardiomyocytes Promotes Recovery of Cardiac Function and Reduction in Cardiac Scar Having demonstrated that forced expression of CITED4 in adult cardiomyocytes in vivo does induce proliferation, Applicant next tested the biological significance of this surprising finding by determining the ability of CITED4 expression to rescue cardiac function, and to reduce scar formation after ischemic injury.

Figure 3:
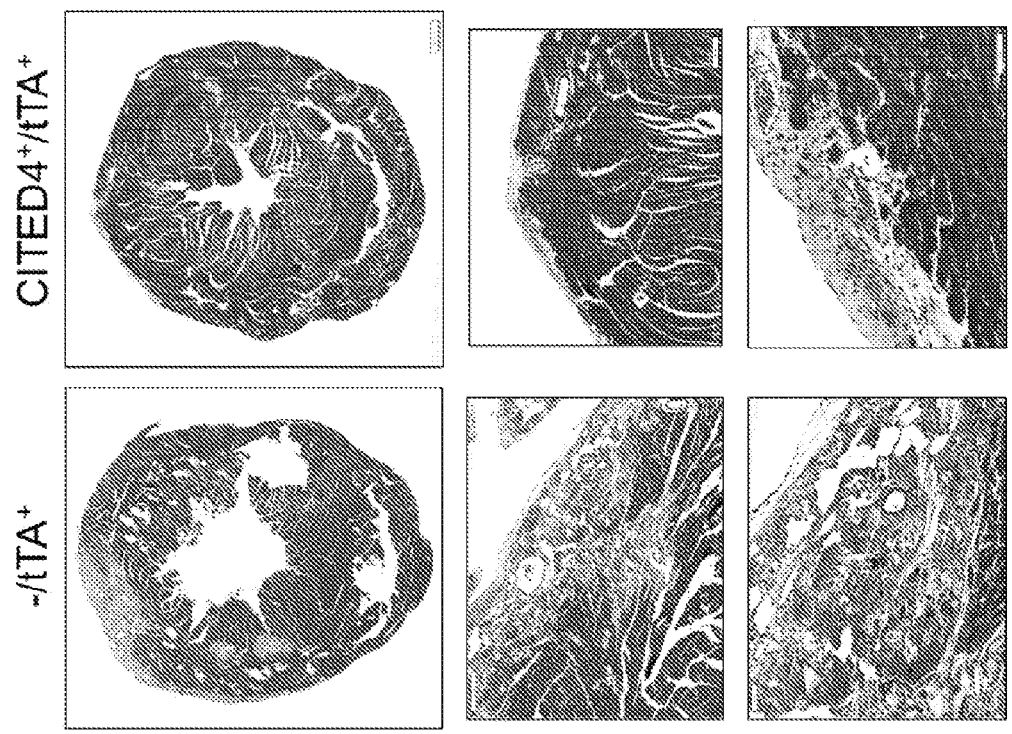
FIG. 3 shows that CITED4 expression promotes recovery and repair after ischemic injury in an animal model.
Figure 3:
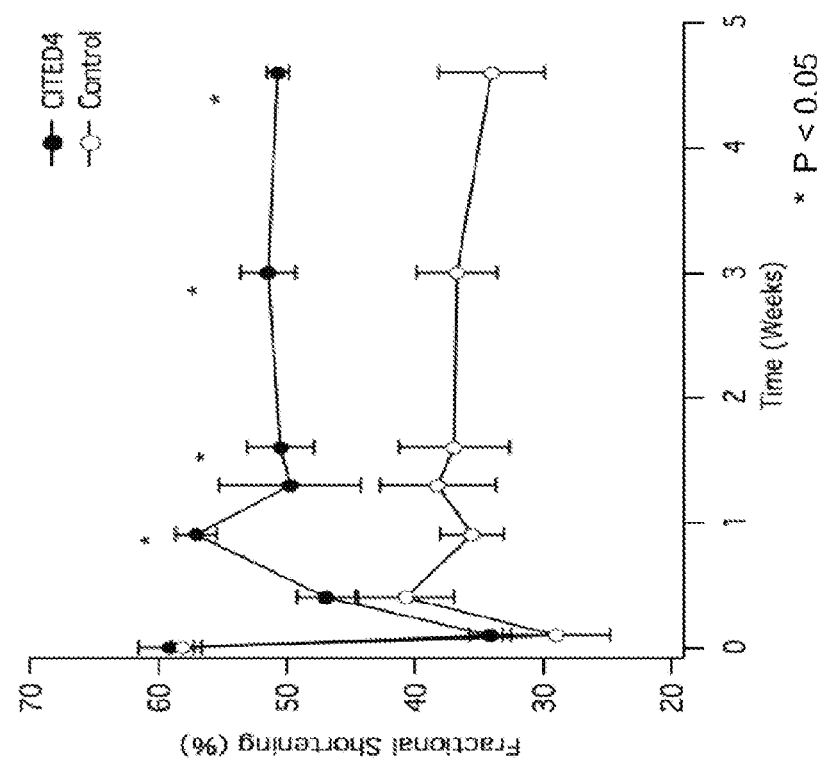

Specifically, CITED4 expression was induced in hearts subjected to ischemia-reperfusion injury, similar to that seen in patients who suffer a myocardial infarction and then receive first line reperfusion therapy. As shown in FIG. 3, the initial reduction (24 hr) in cardiac function, as measured by percentage of fractional shortening, was similar in both CITED4 expressing and control hearts. However, compared to control, the CITED4-expressing hearts showed substantial recovery of cardiac function and reduction in fibrosis (scar) at 5 weeks after injury.

Here, conditional expression of CITED4 is achieved using a transgenic construct expressing CITED4 under the control of a Tet-inducible promoter (see Example 2 above and Sanbe et al., supra). Stained histological sections comparing heart tissues from CITED4-expresing animal to those from negative control show substantial recovery of damaged cardiac tissues and reduced scar/fibrosis.

Taken together, these data demonstrate that CITED4 expression promotes recovery of cardiac function and reduction in cardiac scar, likely through promoting cardiomyocyte survival and cardiomyogenesis.

Example 4 Expression of miR-222 is Induced During Physiological Hypertrophy

To identify microRNA that could be central regulators of physiological cardiac growth, Applicant subjected mice to either voluntary wheel running or a ramp swimming exercise model (Taniike et al., Circulation 117: 545-552, 2008) for three weeks in comparison to sedentary controls. As shown in FIGS. 9A-9E, both models induced mild cardiac hypertrophy, and microRNAs were profiled in hearts samples from each exercise model in comparison to sedentary controls. The TaqMan rodent miRNAarray (A+B set v3.0), which includes 641 unique assays specific to mouse, was used to investigate microRNAs involved in the cardiac exercise response. Five cardiac samples were used from mice exercised in each of the models for three weeks in comparison to matched sedentary controls.

Figure 9E:
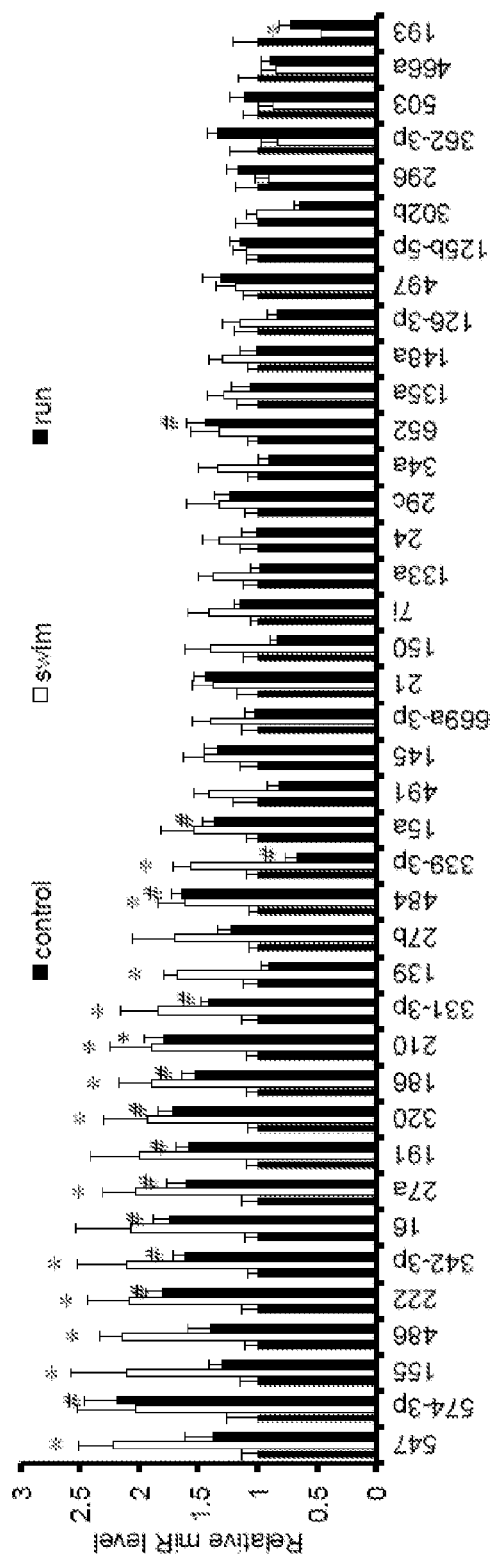

Fifty-five microRNAs were differentially expressed in hearts from animals who had swum, while 124 were differentially expressed in hearts from wheel-run mice, including 16 microRNAs that were concordantly regulated and robustly validated in both models (FIG. 9E and Tables S1a-S1c below).

Figure 10A:
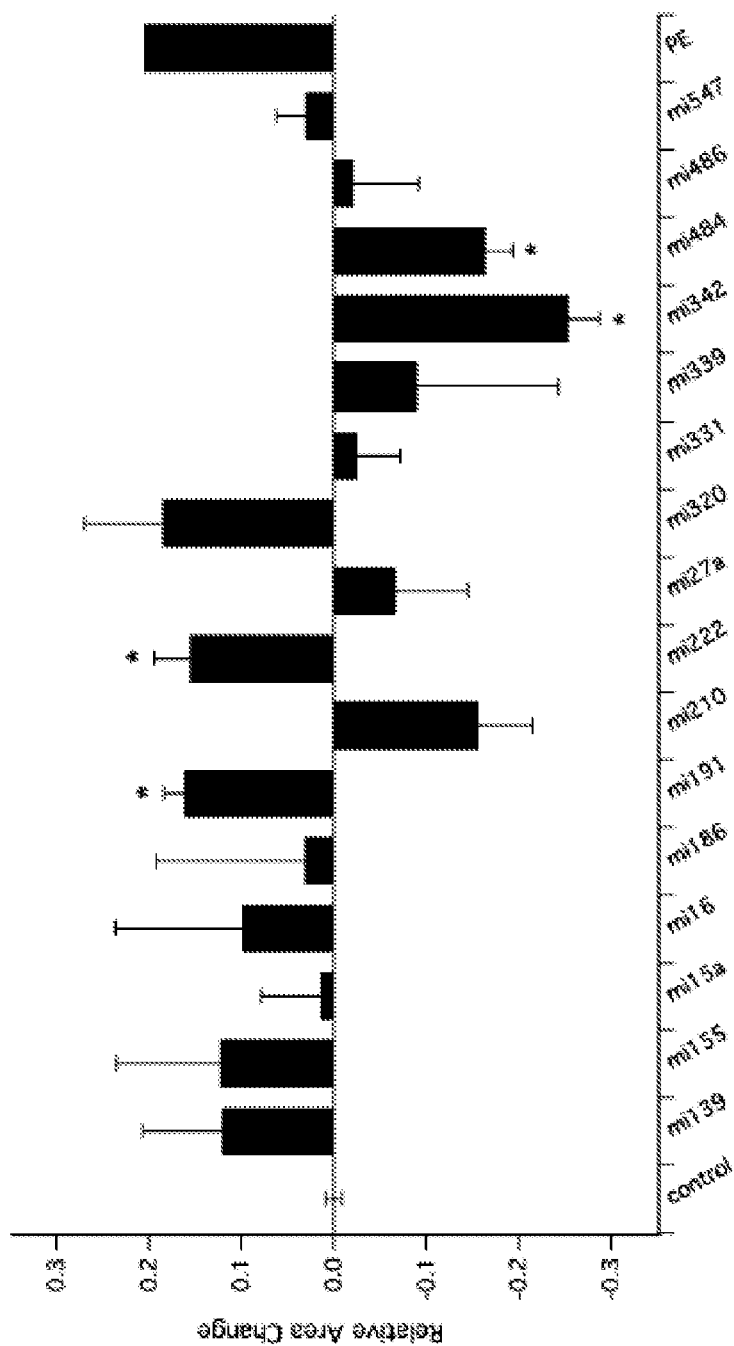
FIGS. 10A-10C show functional effects of validated microRNAs in neonate cardiomyocytes.
Figure 10B:
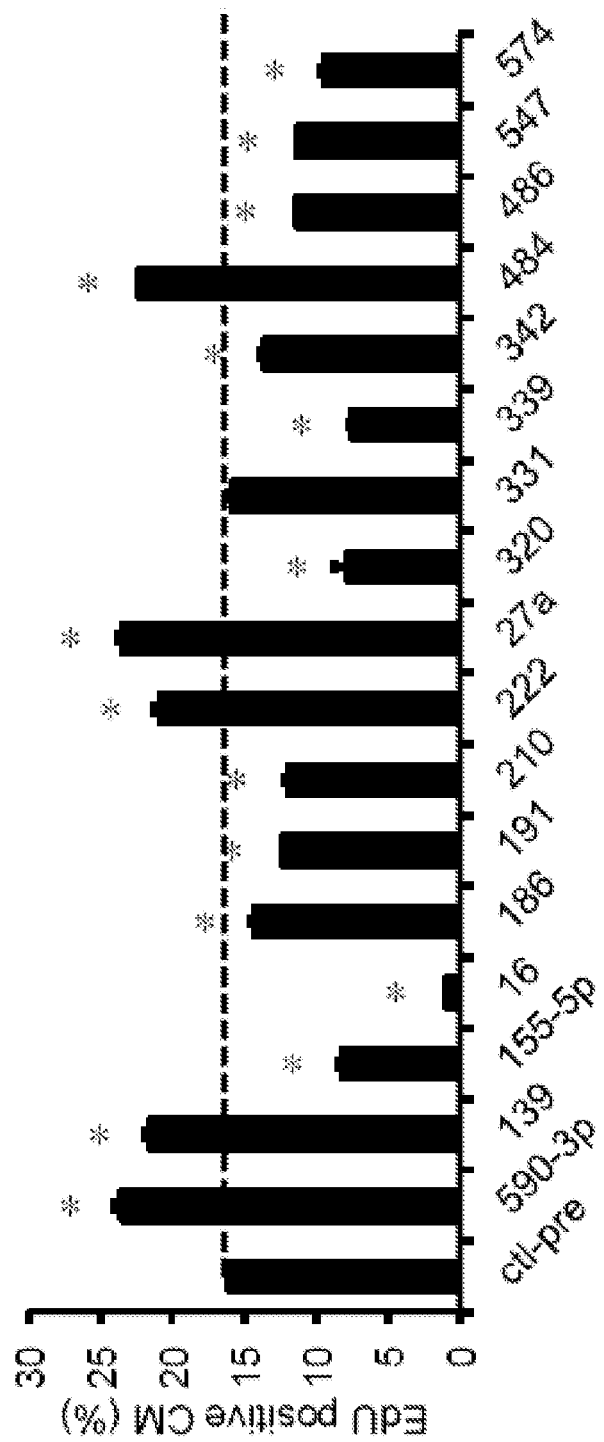

The functional effects of all sixteen candidate microRNAs were examined in cardiomyocytes in vitro using commercially available microRNA precursors. Since cardiomyocyte hypertrophy is central to the acute growth of the heart in response to exercise, a change in cell size was used as an end-point for functional effects (FIG. 10A). In addition, Applicant's prior work had suggested exercise could also induce a proliferative response that might contribute to cardiomyogenesis, and thus incorporation of the thymidine analogue, EdU, in response to microRNA mimic treatment, was also examined (FIG. 10B).

TABLE S1a

Differentially regulated microRNAs in swimming-induced physiological cardiac hypertrophy

| MicroRNAs | Regulation | Fold Change | P-Value |
| --- | --- | --- | --- |
| mmu-miR-215 | Up | 5.4553 | 1.00E−04 |
| mmu-miR-188 | Up | 3.1419 | 0.0054 |
| mmu-miR-574-3p | Up | 3.1029 | 0.0373 |
| mmu-miR-191 | Up | 2.9009 | 0.0067 |
| mmu-miR-331-3p | Up | 2.8028 | 0.0011 |
| mmu-miR-320 | Up | 2.7361 | 0.0217 |
| mmu-miR-342-3p | Up | 2.7006 | 0.0052 |
| mmu-miR-210 | Up | 2.6852 | 0.0025 |
| mmu-miR-339-3p | Up | 2.5788 | 0.0015 |
| mmu-miR-193 | Up | 2.4662 | 0.0314 |
| mmu-miR-150 | Up | 2.4127 | 1.00E−04 |
| mmu-miR-16 | Up | 2.4003 | 0.0077 |
| mmu-miR-139-5p | Up | 2.3778 | 0.0036 |
| mmu-miR-486 | Up | 2.3278 | 9.00E−04 |
| mmu-miR-155 | Up | 2.2862 | 0.0058 |
| mmu-miR-126-3p | Up | 2.27 | 0.0039 |
| mmu-miR-547 | Up | 2.2505 | 0.0057 |
| mmu-miR-222 | Up | 2.1216 | 0.0145 |
| mmu-miR-194 | Up | 1.9672 | 0.017 |
| mmu-miR-484 | Up | 1.9653 | 0.0191 |
| mmu-miR-29o | Up | 1.9432 | 3.00E−04 |
| mmu-miR-491 | Up | 1.9266 | 0.0133 |
| mmu-miR-132 | Up | 1.8972 | 0.0038 |
| mmu-miR-133a | Up | 1.8963 | 0.0037 |
| mmu-miR-24 | Up | 1.8391 | 0.0017 |
| mmu-miR-133b | Up | 1.7433 | 0.011 |
| mmu-miR-106a | Up | 1.7175 | 0.0355 |
| mmu-miR-805 | Up | 1.6103 | 0.0444 |
| mmu-miR-30o | Up | 1.4717 | 0.0334 |
| mmu-miR-302b | Down | 6.4392 | 0.0488 |
| mmu-miR-652 | Down | 3.9526 | 0.0279 |
| mmu-miR-682 | Down | 3.7793 | 0.0213 |
| mmu-miR-541 | Down | 3.7538 | 0.0327 |
| mmu-miR-671-3p | Down | 3.6324 | 0.065 |
| mmu-miR-669a | Down | 3.1786 | 0.0145 |
| mmu-miR-148a | Down | 2.9967 | 0.0196 |
| mmu-miR-497 | Down | 2.7071 | 0.005 |
| mmu-miR-34a | Down | 2.6567 | 0.0019 |
| mmu-miR-101a# | Down | 2.5304 | 0.0296 |
| mmu-miR-296-5p | Down | 2.5221 | 0.0301 |
| mmu-miR-21 | Down | 2.4888 | 0.0219 |
| mmu-miR-27b | Down | 2.4716 | 0.0332 |

TABLE S1a-continued

Differentially regulated microRNAs in swimming-induced physiological cardiac hypertrophy

| MicroRNAs | Regulation | Fold Change | P-Value |
|---|---|---|---|
| mmu-miR-466a-3p | Down | 2.2401 | 0.029 |
| mmu-miR-27a | Down | 2.2381 | 0.0479 |
| mmu-miR-362-3p | Down | 2.1057 | 0.0258 |
| mmu-miR-15a | Down | 1.9474 | 0.0395 |
| mmu-miR-467H | Down | 1.9242 | 0.0208 |
| mmu-miR-145 | Down | 1.9073 | 0.037 |
| mmu-miR-135a | Down | 1.9015 | 0.0237 |
| mmu-let-7i | Down | 1.8252 | 0.0132 |
| mmu-miR-203 | Down | 1.8012 | 0.0319 |
| mmu-miR-125b-5p | Down | 1.7479 | 0.0247 |
| mmu-miR-299 | Down | 1.6858 | 0.0226 |
| mmu-miR-503 | Down | 1.6636 | 0.0281 |
| mmu-miR-706 | Down | 1.5763 | 0.0443 |

TABLE S1b

Differentially regulated microRNAs in running-induced physiological cardiac hypertrophy

| MicroRNAs | Regulation | Fold Change | P-Value |
|---|---|---|---|
| mmu-miR-672 | Up | 8.9382 | 0.0189 |
| mmu-miR-134 | Up | 7.4921 | 0.0206 |
| mmu-miR-138 | Up | 7.3724 | 0.0224 |
| mmu-miR-574-3p | Up | 7.3454 | 0.0142 |
| mmu-miR-320 | Up | 5.9645 | 5.00E−04 |
| mmu-miR-184 | Up | 5.5578 | 0.0412 |
| mmu-miR-187 | Up | 5.1919 | 0.0114 |
| mmu-miR-539 | Up | 4.9923 | 0.0297 |
| mmu-miR-125a-5p | Up | 4.6621 | 0.0036 |
| mmu-miR-342-3p | Up | 4.6727 | 0.0182 |
| mmu-miR-210 | Up | 4.5854 | 6.00E−04 |
| mmu-miR-409-3p | Up | 4.5072 | 0.0105 |
| mmu-miR-339-3p | Up | 4.4926 | 0.0095 |
| mmu-miR-139-3p | Up | 4.4704 | 0.0023 |
| mmu-miR-186 | Up | 4.4307 | 1.00E−04 |
| mmu-miR-191 | Up | 4.3444 | 0.0074 |
| mmu-miR-331-3p | Up | 4.0695 | 0.0038 |
| mmu-miR-15 | Up | 4.0587 | 2.00E−04 |
| mmu-miR-877# | Up | 3.7674 | 0.0465 |
| mmu-miR-322# | Up | 3.7041 | 0.0257 |
| mmu-miR-484 | Up | 3.6962 | 0.0104 |
| mmu-miR-150 | Up | 3.5427 | 0.0018 |
| mmu-miR-486 | Up | 3.3884 | 7.00E−04 |
| mmu-miR-1839-3p | Up | 3.3702 | 0.0377 |
| mmu-miR-128-3p | Up | 3.2472 | 0.0066 |
| hsa-miR-338-5p | Up | 3.1266 | 0.0243 |
| mmu-miR-487b | Up | 3.0833 | 0.0013 |
| mmu-miR-410 | Up | 3.0749 | 0.025 |
| mmu-miR-676 | Up | 2.9752 | 0.0013 |
| mmu-miR-193 | Up | 2.8062 | 0.047 |
| hsa-miR-140-3p | Up | 2.7851 | 0.0037 |
| mmu-miR-222 | Up | 2.7629 | 0.0021 |
| mmu-miR-411 | Up | 2.6984 | 0.0059 |
| mmu-miR-582-3p | Up | 2.6843 | 0.0422 |
| mmu-miR-141 | Up | 2.661 | 0.0209 |
| hsa-miR-33a# | Up | 2.5435 | 0.037 |
| mmu-miR-146a | Up | 2.53 | 0.0017 |
| mmu-miR-297b-5p | Up | 2.5056 | 0.0223 |
| mmu-miR-29c | Up | 2.4589 | 0.0079 |
| mmu-miR-425 | Up | 2.4568 | 0.0016 |
| mmu-miR-125b-3p | Up | 2.4535 | 0.0269 |
| mmu-miR-138 | Up | 2.4099 | 0.0241 |
| mmu-miR-1198 | Up | 2.3939 | 0.0372 |
| mmu-miR-370 | Up | 2.3304 | 0.0304 |
| mmu-miR-139-5p | Up | 2.324 | 0.0286 |
| mmu-miR-489 | Up | 2.2685 | 0.0297 |
| mmu-miR-133a | Up | 2.2619 | 0.0163 |
| mmu-miR-547 | Up | 2.2096 | 0.0067 |
| hsa-miR-299-5p | Up | 2.183 | 0.0343 |
| mmu-miR-351 | Up | 2.1803 | 0.0158 |
| mmu-miR-24 | Up | 2.152 | 0.0025 |
| mmu-miR-374-5p | Up | 2.1408 | 0.0066 |
| mmu-miR-378o | Up | 2.0367 | 0.0283 |
| mmu-miR-744 | Up | 2.0341 | 0.0416 |
| mmu-miR-155 | Up | 1.9282 | 0.0493 |
| mmu-miR-20a# | Up | 1.8015 | 0.0424 |
| hsa-miR-421 | Up | 1.7703 | 0.0497 |
| mmu-miR-491 | Up | 1.7234 | 0.0315 |
| hsa-miR-26b# | Up | 1.6757 | 0.0428 |
| mo-miR-664 | Up | 1.4689 | 0.0094 |
| mmu-miR-24-2# | Up | 1.3874 | 0.0357 |
| mmu-miR-302b | Down | 14.3472 | 0.0214 |
| mmu-miR-652 | Down | 9.6805 | 0.0157 |
| mmu-miR-2135 | Down | 8.1967 | 0.0015 |
| mmu-miR-2134 | Down | 6.7935 | 0.0098 |
| mmu-miR-27b | Down | 6.3012 | 0.0106 |
| mmu-miR-497 | Down | 6.2735 | 0.0018 |
| mmu-miR-328 | Down | 5.8582 | 0.0422 |
| mmu-miR-499 | Down | 5.7937 | 0.019 |
| mmu-miR-128a | Down | 5.3619 | 0.0486 |
| mmu-miR-451 | Down | 5.4318 | 0.0286 |
| mmu-miR-135a | Down | 5.1282 | 0.0018 |
| mmu-miR-221 | Down | 4.9875 | 0.0053 |
| mmu-miR-148a | Down | 4.9068 | 0.0094 |
| mmu-miR-696 | Down | 4.7326 | 0.0326 |
| mmu-miR-322 | Down | 4.3497 | 0.0291 |
| mmu-let-7i | Down | 4.2194 | 0.0016 |
| mmu-miR-21 | Down | 4.1237 | 0.0077 |
| hsa-miR-378 | Down | 4.0717 | 0.0123 |
| mmu-miR-361 | Down | 4.0486 | 0.0382 |
| mmu-miR-345-5p | Down | 3.7879 | 0.0083 |
| mmu-miR-10b | Down | 3.7369 | 0.0492 |
| hsa-miR-875-5p | Down | 3.7244 | 0.0151 |
| mmu-miR-27a | Down | 3.6643 | 0.0207 |
| mmu-miR-29b | Down | 3.6298 | 0.0091 |
| mmu-miR-423-5p | Down | 3.5791 | 0.0444 |
| mmu-miR-2182 | Down | 3.4802 | 0.0214 |
| mmu-miR-345-3p | Down | 3.3659 | 0.0438 |
| mmu-miR-145 | Down | 3.3258 | 0.0095 |
| mmu-miR-34a | Down | 3.2971 | 0.0042 |
| mmu-miR-685 | Down | 3.2808 | 0.0401 |
| mmu-miR-490 | Down | 3.2415 | 0.0012 |
| mmu-miR-34c | Down | 3.1192 | 0.0276 |
| mmu-miR-190 | Down | 3.0836 | 0.0374 |
| mmu-miR-494 | Down | 3.0741 | 0.0484 |
| hsa-miR-22 | Down | 2.9931 | 2.00E−04 |
| mmu-miR-23b | Down | 2.9913 | 0.0218 |
| mmu-miR-1905 | Down | 2.9762 | 0.008 |
| hsa-miR-22#1 | Down | 2.8361 | 0.0118 |
| mmu-miR-18a | Down | 2.7863 | 0.0427 |
| mmu-miR-142-3p | Down | 2.751 | 0.0468 |
| mmu-miR-181a | Down | 2.6889 | 0.0107 |
| mmu-miR-15a | Down | 2.6717 | 0.0192 |
| mmu-miR-669a | Down | 2.6575 | 0.0256 |
| mmu-miR-7d# | Down | 2.6151 | 0.0418 |
| mmu-miR-25 | Down | 2.5753 | 0.0479 |
| mmu-miR-125b-5p | Down | 2.5259 | 0.0085 |
| mmu-miR-130a | Down | 2.5189 | 0.0386 |
| mmu-miR-20a | Down | 2.4331 | 0.0113 |
| mmu-miR-296-5p | Down | 2.4195 | 0.0333 |
| mmu-miR-19b | Down | 2.2604 | 0.0029 |
| mmu-miR-466a-3p | Down | 2.2065 | 0.0493 |
| mmu-miR-362-3p | Down | 2.1839 | 0.0242 |
| mmu-miR-1896 | Down | 2.158 | 0.0058 |
| mmu-miR-503 | Down | 2.1245 | 0.0097 |
| mmu-miR-143 | Down | 2.0743 | 0.017 |
| mmu-miR-181c | Down | 1.9666 | 0.0385 |
| mmu-miR-10a | Down | 1.9823 | 0.0249 |
| mmu-miR-19a | Down | 1.9448 | 0.0487 |
| mmu-miR-208 | Down | 1.8615 | 0.0066 |
| mmu-miR-339-5p | Down | 1.8399 | 0.0298 |
| mmu-miR-2146 | Down | 1.8155 | 0.001 |
| mmu-miR-1944 | Down | 1.7082 | 0.0289 |
| mmu-let-7g | Down | 1.3514 | 0.023 |

TABLE S1c

Concordantly regulated microRNAs
in swimming and running induced physiological cardiac hypertrophy

| MicroRNAs | Regulation | Swimming (Fold Change) | Swimming (P-Value) | Running (Fold Change) | Running (P-Value) |
|---|---|---|---|---|---|
| mmu-miR-186 | up | 3.1419 | 0.0054 | 4.4307 | 1.00E−04 |
| mmu-miR-574-3p | up | 3.1029 | 0.0373 | 7.3454 | 0.0142 |
| mmu-miR-191 | up | 2.9009 | 0.0087 | 4.3444 | 0.0074 |
| mmu-miR-331-3p | up | 2.8028 | 0.0011 | 4.0695 | 0.0038 |
| mmu-miR-320 | up | 2.7361 | 0.0217 | 5.9645 | 5.00E−04 |
| mmu-miR-342-3p | up | 2.7006 | 0.0052 | 4.6727 | 0.0182 |
| mmu-miR-210 | up | 2.6852 | 0.0025 | 4.5854 | 6.00E−04 |
| mmu-miR-339-3p | up | 2.5788 | 0.0015 | 4.4926 | 0.0095 |
| mmu-miR-193 | up | 2.4862 | 0.0314 | 2.8052 | 0.047 |
| mmu-miR-150 | up | 2.4127 | 1.00E−04 | 3.5427 | 0.018 |
| mmu-miR-16 | up | 2.4003 | 0.0077 | 4.0587 | 2.00E−04 |
| mmu-miR-139-5p | up | 2.3778 | 0.0036 | 2.324 | 0.0286 |
| mmu-miR-486 | up | 2.3278 | 9.00E−04 | 3.3884 | 7.00E−04 |
| mmu-miR-155 | up | 2.2862 | 0.0058 | 1.9282 | 0.0493 |
| mmu-miR-126-3p | up | 2.27 | 0.0039 | 3.2472 | 0.0068 |
| mmu-miR-547 | up | 2.2505 | 0.0057 | 2.2096 | 0.0067 |
| mmu-miR-222 | up | 2.1216 | 0.0145 | 2.7629 | 0.0021 |
| mmu-miR-484 | up | 1.9653 | 0.0191 | 3.6962 | 0.0104 |
| mmu-miR-29o | up | 1.9432 | 3.00E−04 | 2.4589 | 0.0079 |
| mmu-miR-491 | up | 1.9266 | 0.0133 | 1.7234 | 0.0315 |
| mmu-miR-133a | up | 1.8963 | 0.0037 | 2.2619 | 0.0163 |
| mmu-miR-24 | up | 1.8391 | 0.0017 | 2.152 | 0.0025 |
| mmu-miR-302b | down | 6.4392 | 0.0488 | 14.3472 | 0.0214 |
| mmu-miR-852 | down | 3.9528 | 0.0279 | 9.6805 | 0.0157 |
| mmu-miR-669a | down | 3.1786 | 0.0145 | 2.6575 | 0.0268 |
| mmu-miR-148a | down | 2.9967 | 0.0196 | 4.9068 | 0.0094 |
| mmu-miR-497 | down | 2.7071 | 0.005 | 6.2735 | 0.0018 |
| mmu-miR-34a | down | 2.6567 | 0.0019 | 3.2971 | 0.0042 |
| mmu-miR-296-5p | down | 2.5221 | 0.0301 | 2.4195 | 0.0333 |
| mmu-miR-21 | down | 2.4888 | 0.0219 | 4.1237 | 0.0077 |
| mmu-miR-27b | down | 2.4718 | 0.0332 | 6.3012 | 0.0108 |
| mmu-miR-466a-3p | down | 2.2401 | 0.029 | 2.2065 | 0.0493 |
| mmu-miR-27a | down | 2.2361 | 0.0479 | 3.6643 | 0.0207 |
| mmu-miR-382-3p | down | 2.1057 | 0.0258 | 2.1839 | 0.0242 |
| mmu-miR-15a | down | 1.9474 | 0.0395 | 2.6717 | 0.0192 |
| mmu-miR-145 | down | 1.9073 | 0.037 | 3.3256 | 0.0095 |
| mmu-miR-135a | down | 1.9015 | 0.0237 | 5.1282 | 0.0018 |
| mmu-let-7i | down | 1.8252 | 0.0132 | 4.2194 | 0.0016 |
| mmu-miR-125b-5p | down | 1.7479 | 0.0247 | 2.5259 | 0.0085 |
| mmu-miR-503 | down | 1.6638 | 0.0281 | 2.1245 | 0.0097 |

Figure 10C:
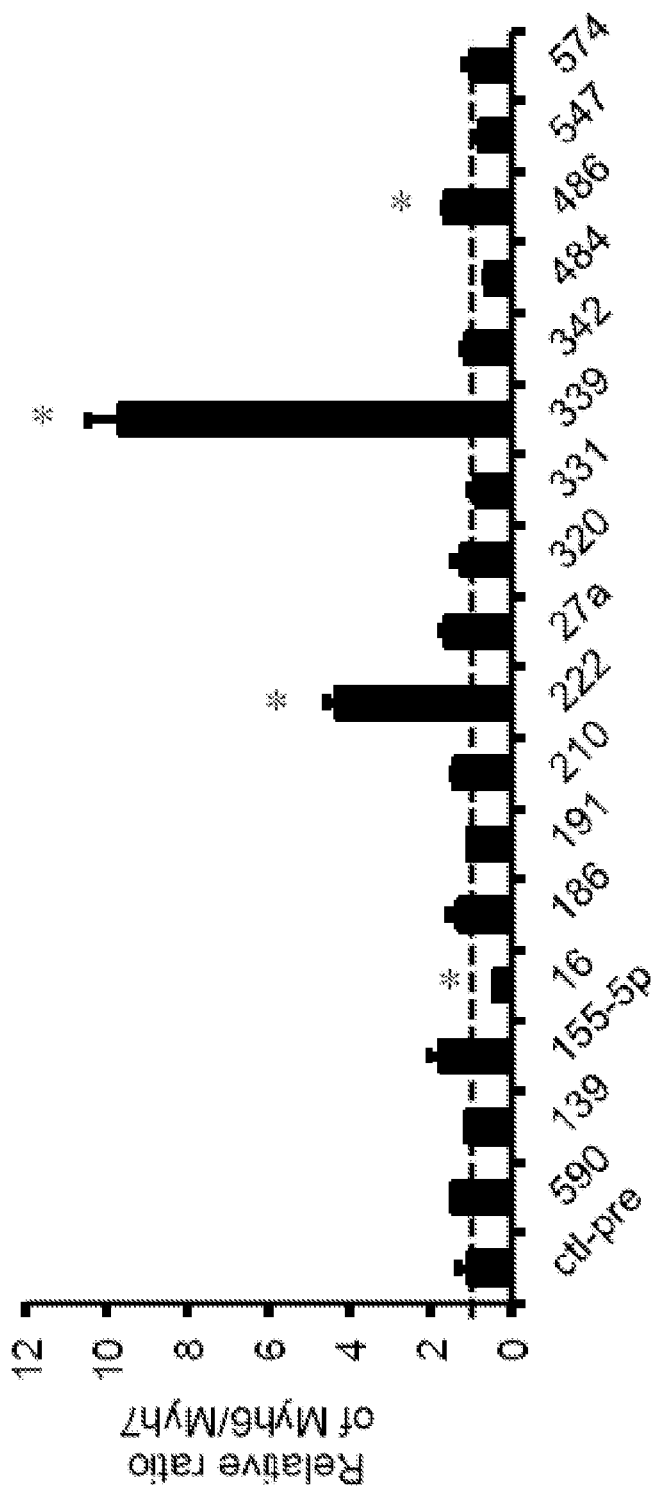

As shown in Tables S1a-S1c, miR-222 emerged as a particularly interesting candidate that was increased 2.1- and 2.8-fold in the swimming and running exercise models, respectively (p<0.003 and 0.02). miR-222 was one of two microRNAs (along with miR-191) that increased cardiomyocyte size in vitro, and one of four (along with miR-139, -27a and -484) that increased EdU incorporation, a measure of proliferation (FIGS. 10A and 10B). Subsequent studies showed that only miR-222, miR-339, and miR-486 induced a physiological pattern of myosin heavy chain isoform expression (FIG. 10C). Based on the unique convergence of these characteristics, miR-222 was further studied below.

Example 5 miR-222 is Required for Cardiac Exercise Response

Applicant has identified that the level of microRNA miR-222 is increased in exercised hearts. miR-222 is a highly conserved micro-RNA that has been reported by others to increase in serum of exercised athletes. The role of miR-222 in the heart, however, is unknown.

Figure 4C:
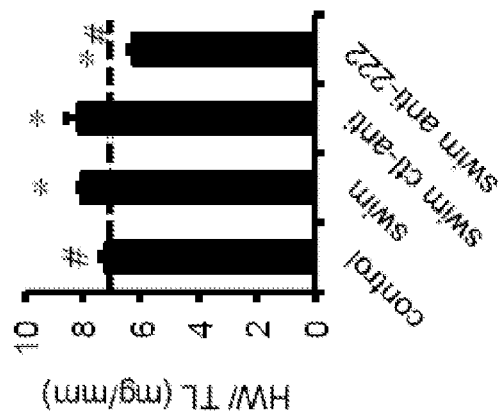
FIGS. 4A-4F show that miR-222 is necessary for exercise-induced cardiac growth in vivo.
Figure 4B:
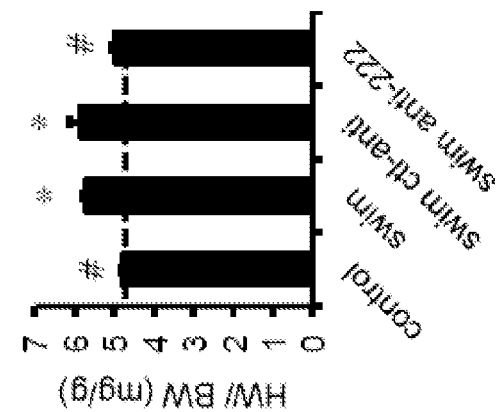
Figure 4A:
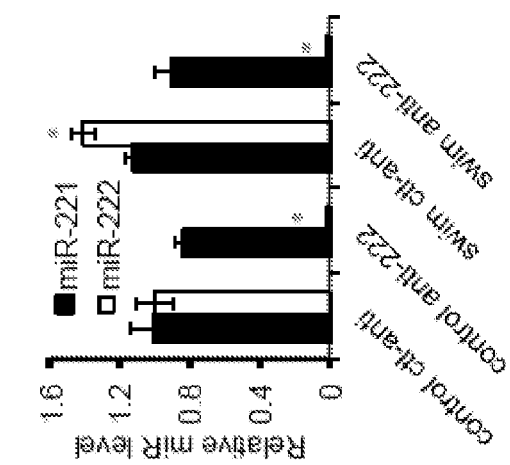

To investigate the role of miR-222 expression in the in vivo cardiac exercise response (Bostrom et al., Cell 143: 1072-1083, 2010), Applicant injected mice with LNA-anti-miR-222 or scrambled control LNA-anti-miR for three days prior to exercise, and then weekly during the three week swim protocol. LNA-antimiR-222 decreased cardiac miR-222 expression in hearts from both sedentary and exercised animals by >98% without affecting the expression of the closely related miR-221 (FIG. 4A). As reported previously, exercised but untreated animals showed an increase in cardiac mass reflected in ratios of heart weight to body weight (HW/BW) or tibial length (HW/TL) which were increased 21% and 15% respectively (p<0.001 for both) in comparison to sedentary controls (FIGS. 4B & 4C). The scrambled LNA-antimiR did not affect this growth while the specific LNA-antimiR-222 completely blocked the increase in heart size and after three weeks of intensive exercise their hearts were no different in size from sedentary animals (FIGS. 4B & 4C).

As noted earlier, short-term changes in heart size are often related to changes in cardiomyocyte size and, indeed, examination of cardiomyocyte size on WGA-stained sections revealed a similar pattern. Cardiomyocyte size increased >20% (p<0.05) in untreated, exercised mice, and this was similar in mice which swam and were treated with the control LNA-antimiR (p=NS) (FIG. 4D). In contrast, cardiomyocytes in swum mice treated with LNA-antimiR-222 were no different in size from cardiomyocytes in sedentary, untreated mice (p=NS).

Figure 4F:
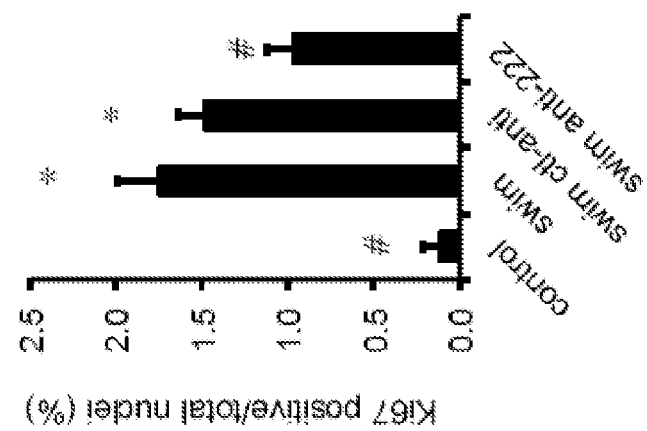
Figure 4E:
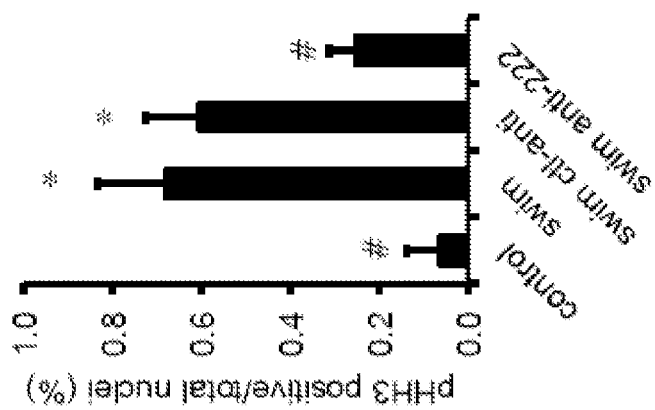
Figure 4D:
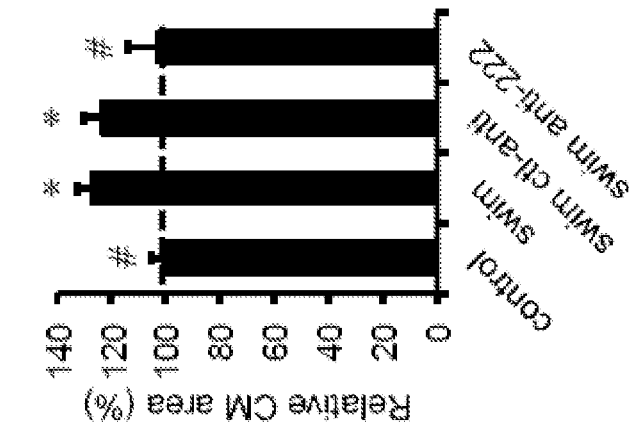
Figure 5:
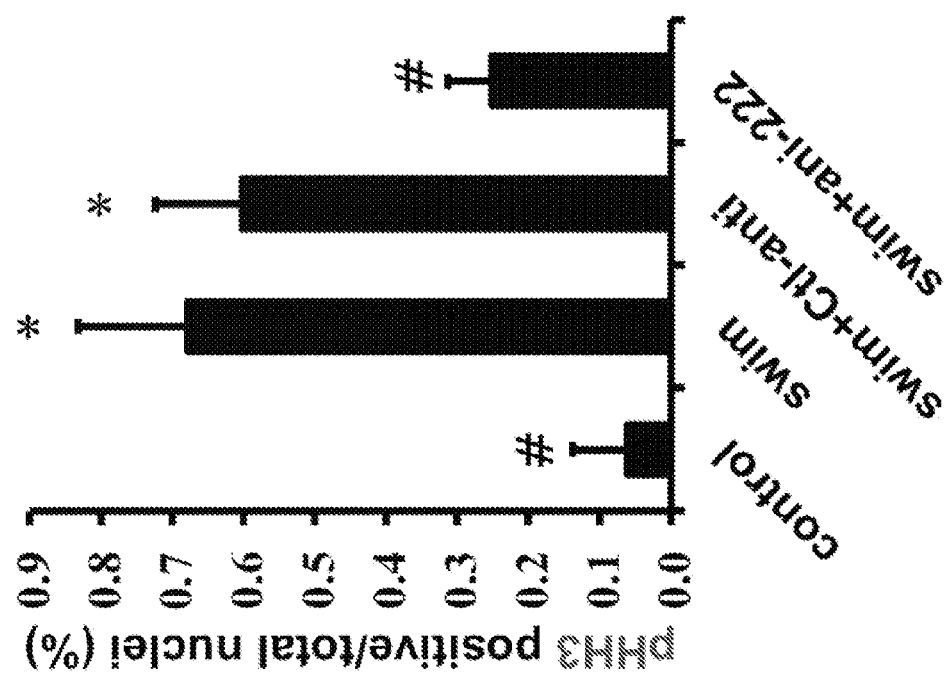
FIG. 5 shows that treatment of exercising animals with LNA-anti-miR-222 blocks the induction of phospho-histone-H3, a marker of cell proliferation, specifically in the cardiomyocyte lineage.
Figure 5:
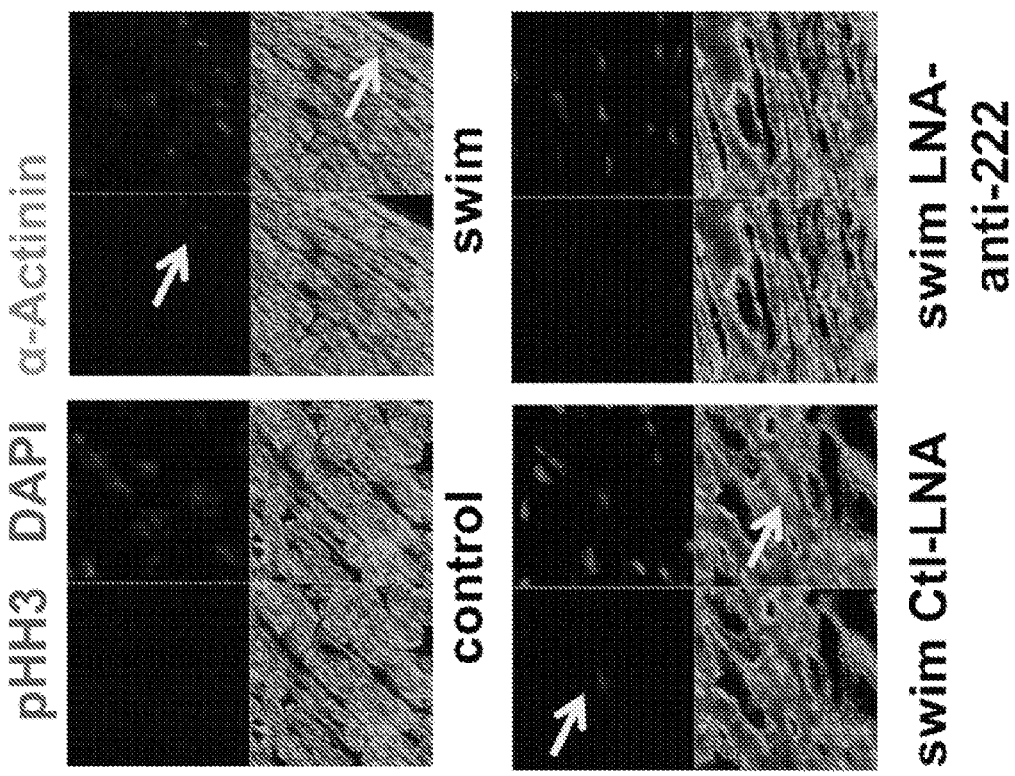

Applicant's prior work had suggested that exercise increases markers of proliferation in the cardiomyocyte lineage, and, indeed, a substantial increase in both phospho-HistoneH3 (pHH3) and ki67 was again seen in cardiomyocytes from exercised, untreated animals (FIGS. 4E & 4F). This increase was not altered by the control antimiR, but was decreased, though not reduced to baseline, by LNA-anti-miR-222. These studies demonstrate that miR-222 is also necessary for the previously reported proliferative response to exercise in the heart (FIG. 5).

Taken together, these data demonstrate that miR-222 is necessary for the short-term growth of the heart and cardiomyocytes in response to exercise. miR-222 also appears to contribute to the increase in markers of proliferation seen in cardiomyocytes after exercise.

Example 6 miR-222 Expression is Sufficient to Mediate Cardiomyogenesis miR-222 is a highly conserved member of a microRNA cluster encoded on the X chromosome, which also includes miR-221 (Felli et al., Proc Natl Acad Sci USA 102: 18081-18086, 2005; Galardi et al., J Biol Chem 282: 23716-23724, 2007). Its function in the heart is unknown.

Figure 11A:
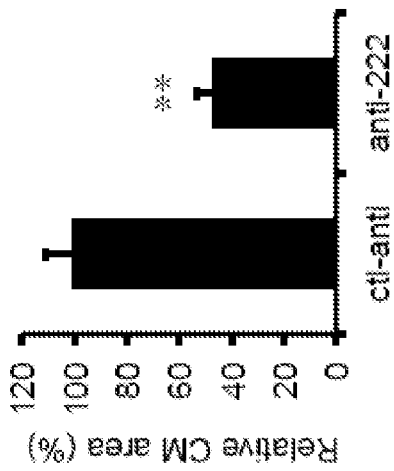
Figure 11B:
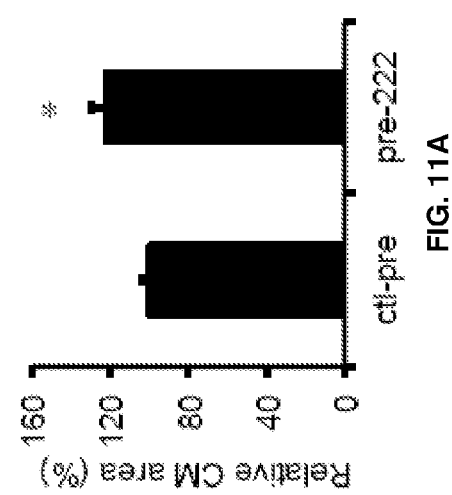
Figure 11C:
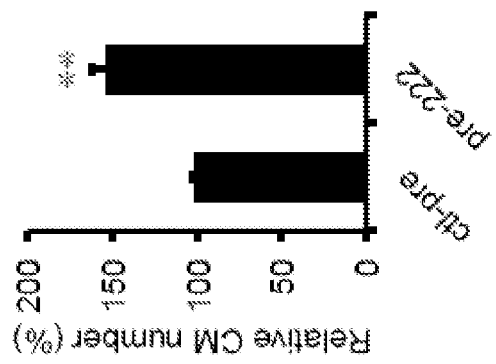
Figure 11C:
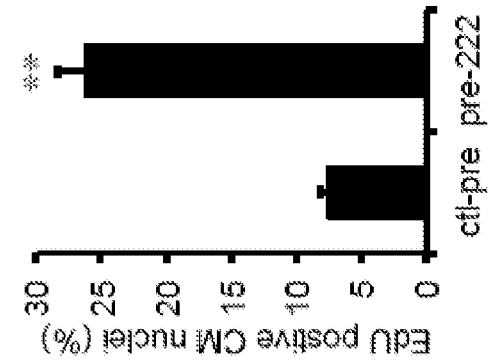

Forced expression of miR-222 induced an increase in cardiomyocyte size (FIG. 11A). miR-222 expression caused an increase in markers of cardiomyocyte proliferation (as seen in the initial characterization) as well as cell number (FIG. 11C). Moreover, miR-222 induced a pattern of gene expression in cardiomyocytes consistent with healthy or physiological growth, including an increase in myosin heavy chain (MHC)-$\alpha/\beta$ ratio, as well as decreases in expression of ANP, BNP, and $\alpha$-skeletal actin mRNAs (FIG. 11E). These data indicate that miR-222 expression is sufficient to induce a complex pattern of cardiomyocyte physiological growth, including cellular hypertrophy and proliferation.

Intriguingly, miR-222 has also been reported to increase in the plasma of athletes in response to both acute and chronic exercise (Baggish et al., Dynamic Regulation of Circulating MicroRNA during Acute Exhaustive Exercise and Sustained Aerobic Exercise Training. J Physiol (Lond), 2011), suggesting the potential human relevance of these observations. Of note, neither miR-221 expression in hearts nor miR-222 expression in skeletal muscle was increased in our exercised mice (data not shown).

Example 7 miR-222 Protects Against Cardiac Dysfunction after Ischemic Injury

To further test whether miR-222 expression is sufficient to mediate cardiomyogenesis and provide functional benefits in vivo, Applicant created an inducible, regulated bigenic transgenic model that permits turning on expression of miR-222 specifically in cardiomyocytes. See Example 3 above. Using this system, Applicant induced miR-222 expression in mice subjected to ischemia-reperfusion injury (30 minutes ischemia followed by reperfusion), similar to patients suffering from a heart attack who then receive first-line reperfusion therapy.

Figure 12B:
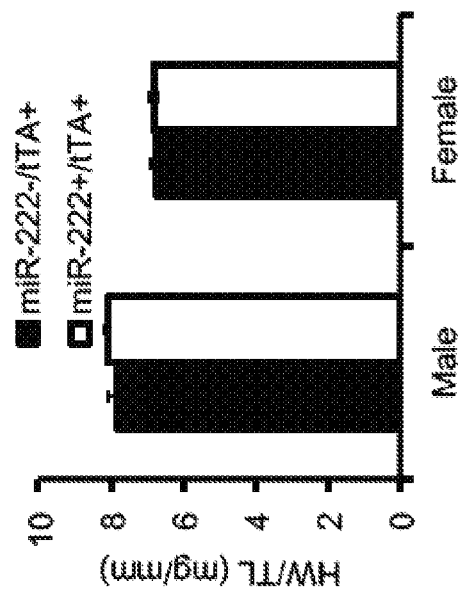
FIG. 12A-12B show baseline characteristics of Tg-miR-222 mice.
Figure 12A:
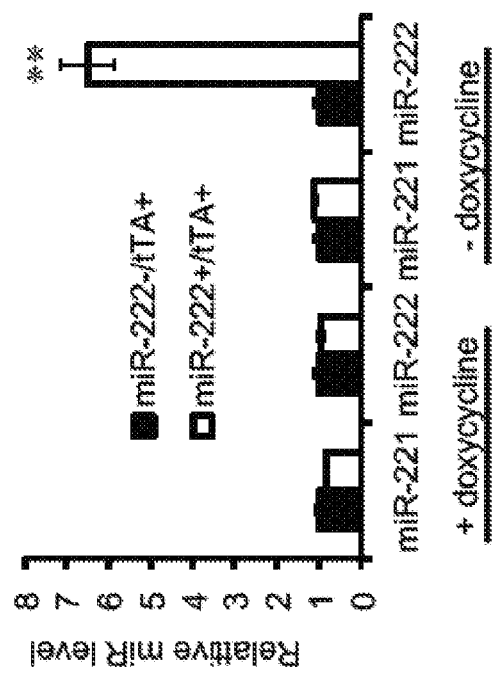

Specifically, since miR-222 increases in exercised hearts, Applicant created inducible (doxycycline-off) cardiac-specific miR-222 transgenics (Tg-miR-222) to investigate the effects of cardiac miR-222 expression. Tg-miR-222 mice manifest regulated, cardiac-specific miR-222 expression that was ~6.5-fold increased 4 weeks after removal of doxycycline from chow (FIG. 12A). Interestingly, Tg-miR-222 mice appeared grossly normal at baseline after induction of cardiac miR-222 expression with normal heart size (FIG. 12B) and cardiac function (as measured by ECG analysis). Thus, although miR-222 is necessary for growth of the heart in response to exercise, miR-222 expression, even at levels higher than those induced by exercise, appears to be insufficient to recapitulate the exercised-heart phenotype.

Exercise reduces adverse ventricular remodeling and cardiac dysfunction when initiated after infarction in animal models and humans, attenuating fibrosis, dilatation, and both systolic and diastolic dysfunction. To critically assess the possible protective role of miR-222 expression in this context, Tg-miR-222 mice were withdrawn from doxycycline and subsequently subjected to ischemia-reperfusion injury (RI) induced by 30 minutes coronary ligation and reperfusion. One day after ischemic injury, Tg-miR-222 mice showed no difference in initial infarct size or degree of cardiac dysfunction in comparison to controls (FIGS. 13A & 13B). However, while control mice showed the progressive ventricular dilation and decline in cardiac function known as adverse remodeling, Tg-miR-222 mice did not, but instead maintained both chamber dimension and cardiac function (FIG. 13B). Six weeks after ischemic injury, miR-222-expressing mice had substantially better cardiac function (FIG. 13B), as well as an almost 70% reduction in cardiac fibrosis (FIG. 13C). Interestingly, in vivo miR-222 expression after ischemic injury was associated with an increase in EdU incorporation in cardiomyocytes but a decrease in EdU incorporation non-cardiomyocytes, which are predominantly fibroblasts (FIG. 13D).

Figure 6:
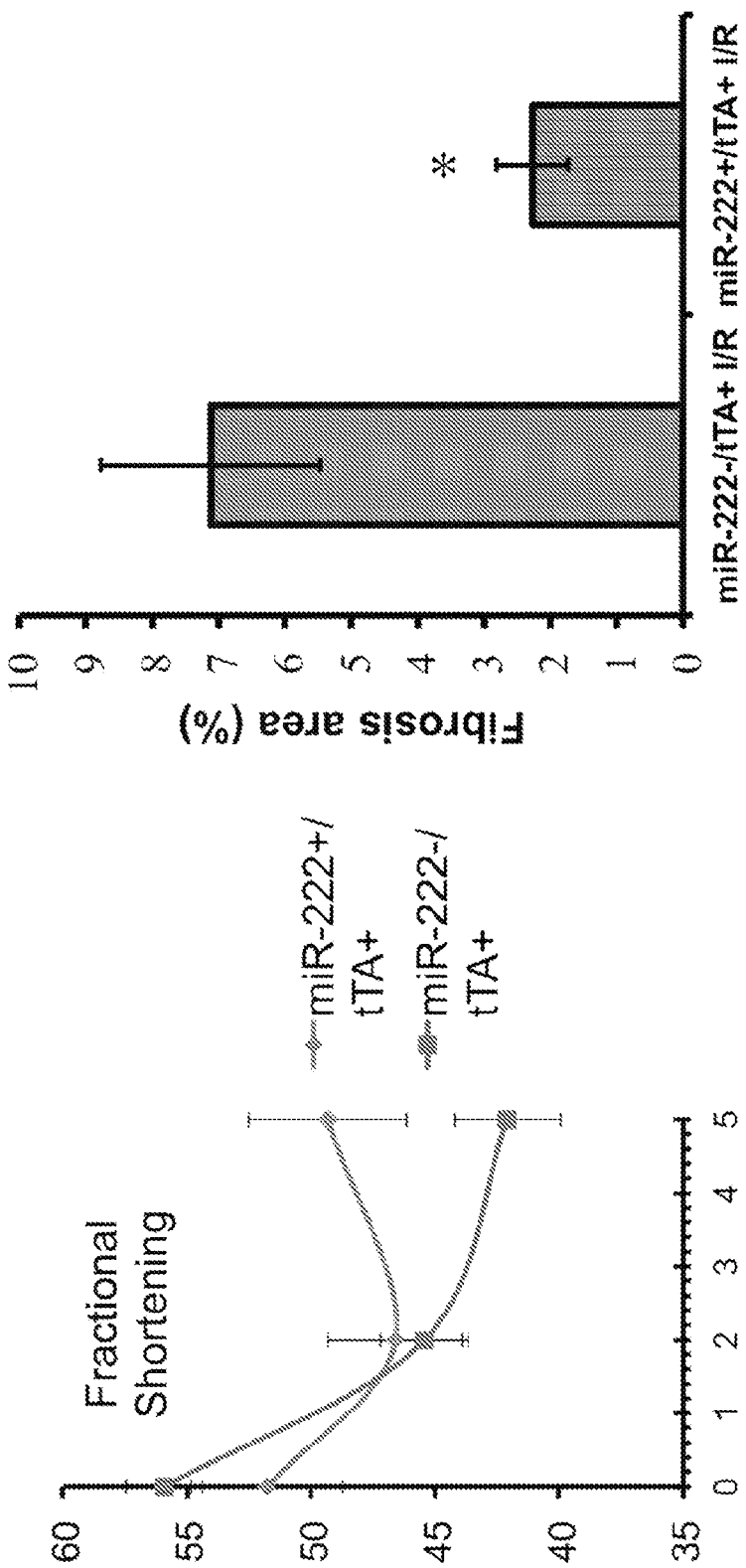
FIG. 6 shows that miR-222 expression promotes functional recovery and reduces scar formation after ischemic injury.

Overall, these data demonstrate that miR-222 expression preserved cardiac structure and function, enhanced functional recovery (as measured by fractional shortening), and is sufficient to mitigate adverse remodeling after ischemic injury. Meanwhile, miR-222 expression reduced scar formation at 6 weeks in comparison to control mice (FIG. 6) (fibrosis measured by Masson Trichrome Staining), after ischemic injury.

Example 8 Multiple miR-222 Target Genes Mediate Distinct Phenotypic Effects

To identify how miR-222 mediates these effects, Applicant used a combination of bioinformatic analyses with expression profiling in miR-222-expressing cardiomyocytes to identify putative target candidates for miR-222, e.g., by transcript profiling on cardiomyocytes expressing miR-222 in comparison to control vector. These data have been deposited in the Gene Expression Omnibus (GEO accession number: GSE59641, incorporated by reference).

Expression profiling revealed that miR-222 induced an increase in CITED4 mRNA levels, indicating cross-talk with the transcriptional pathway linked to exercise. In GO pathway analyses, the most upregulated functional pathway was "Cell Cycle" ($p<10^{-8}$).

Figure 7:
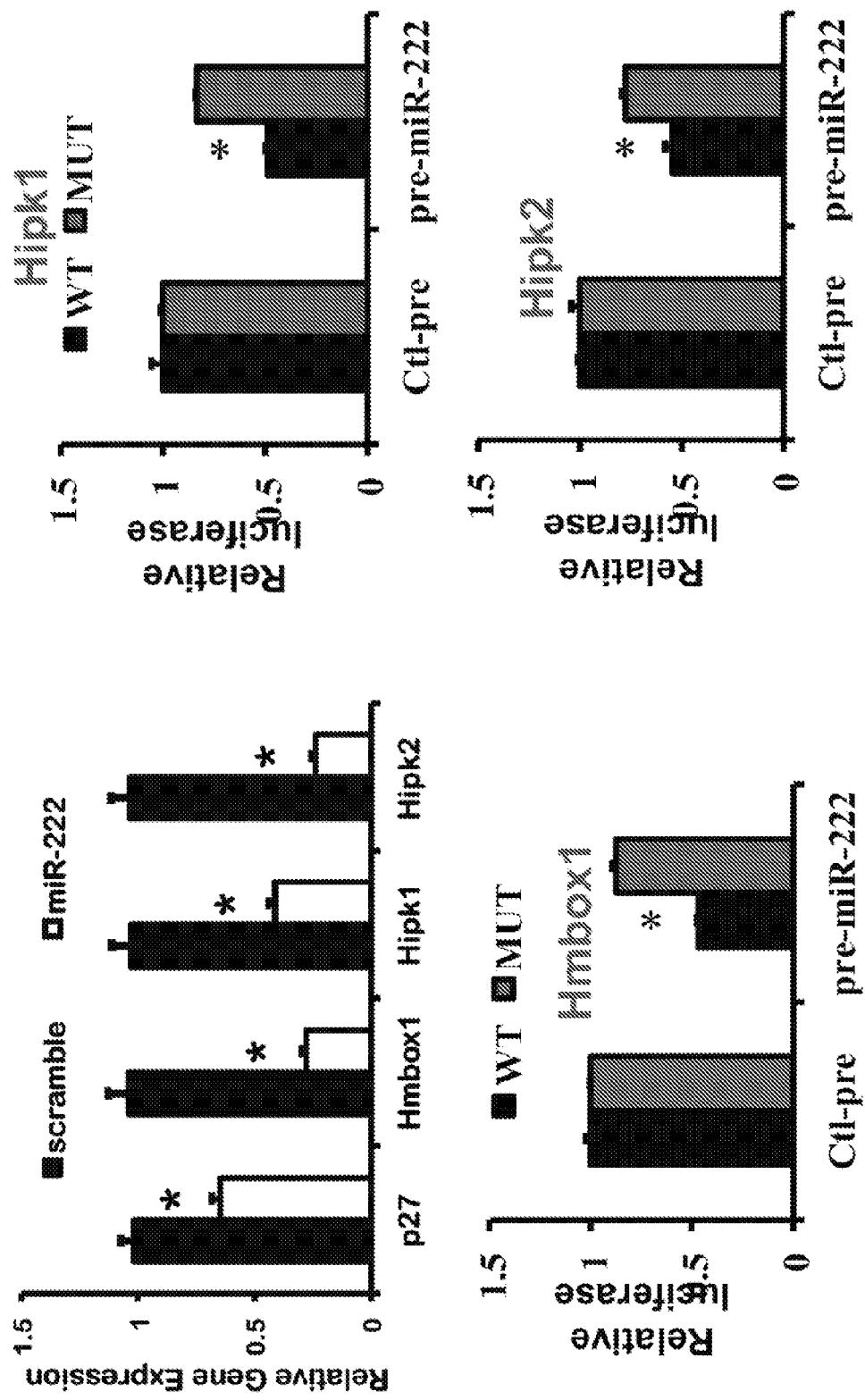
FIG. 7 shows that direct targets of miR-222 in cardiomyocytes include p27, HIPK1 and 2, and Homeobox-1, as shown in expression studies and 3'-UTR luciferase assays with wild-type and mutant 3'-UTRs.

A combination of expression profiling results with miR-222 targets predicted by two bioinformatic programs (Targetscan, Pictar) (FIG. 12A) identified four relevant potential targets whose expression decreased in cardiomyocytes with miR-222 expression. These include the cell cycle inhibitor, p27(kip1), the protein kinases HIPK-1 and -2, and a transcriptional repressor, Hmbox1 (FIG. 7).

Figure 14A:
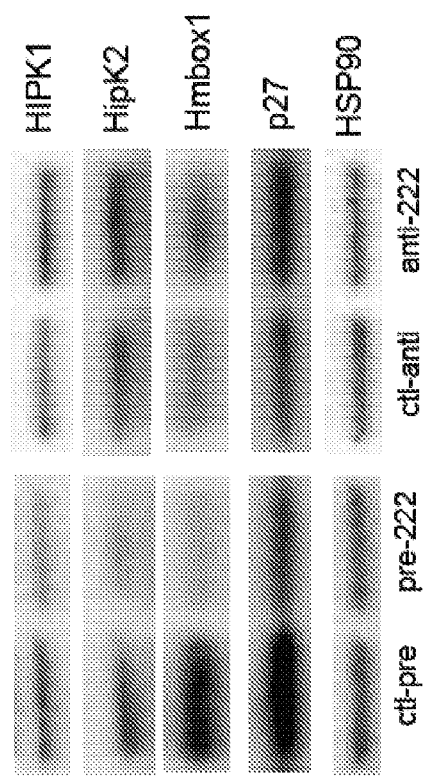
Figure 14B:
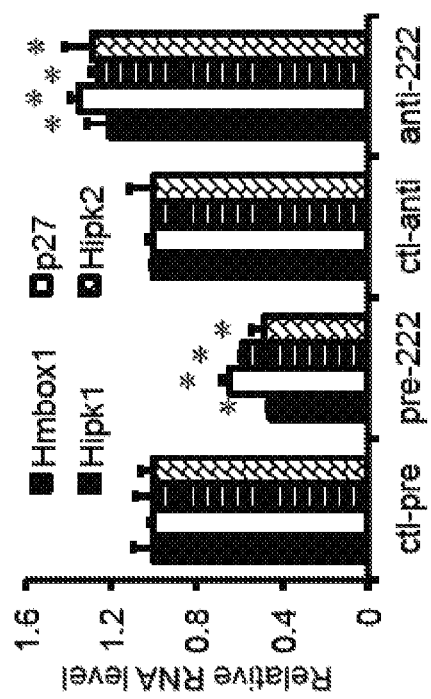

Genetic deletion of p27 induces cardiomyocyte hyperplasia in vivo and physiological cardiac hypertrophy, but accelerates the development of heart failure after biomechanical stress. The other three candidates (HIPK1, HIPK2, and Homeobox1) have not previously been linked to miR-222 and have no known roles in the heart.

miR-222 expression in cardiomyocytes in vitro was sufficient to reduce expression of all four putative targets (p27, HIPK1, HIPK2, Homeobox-1) from 35 to 55 percent, while a specific miR-222 inhibitor increased their expression (FIG. 14A). These changes in RNA levels were paralleled by changes in protein expression for each of the targets (FIG. 14B).

These targets are validated in cardiomyocytes. Specifically, to determine whether HIPK1, HIPK2, and Homeobox-1 were direct targets of miR-222, Applicant cloned either their respective wild-type 3'-UTRs or 3'UTRs in which the putative miR-222 binding sites had been mutated downstream of a luciferase reporter. miR-222 expression had no effect on luciferase activity of the control reporter without a miR-222 binding site (data not shown). In contrast, miR-222 expression induced a reduction in luciferase activity for each of the wild-type 3'UTR constructs but importantly, but had no significant effect when the miR-222 binding sites were mutated (data not shown), demonstrating that the binding interaction is required for this effect. These data strongly suggest that the HIPK1, HIPK2 and Homeobox-1 mRNAs are all direct targets of miR-222, as has been shown for p27.

Figure 8:
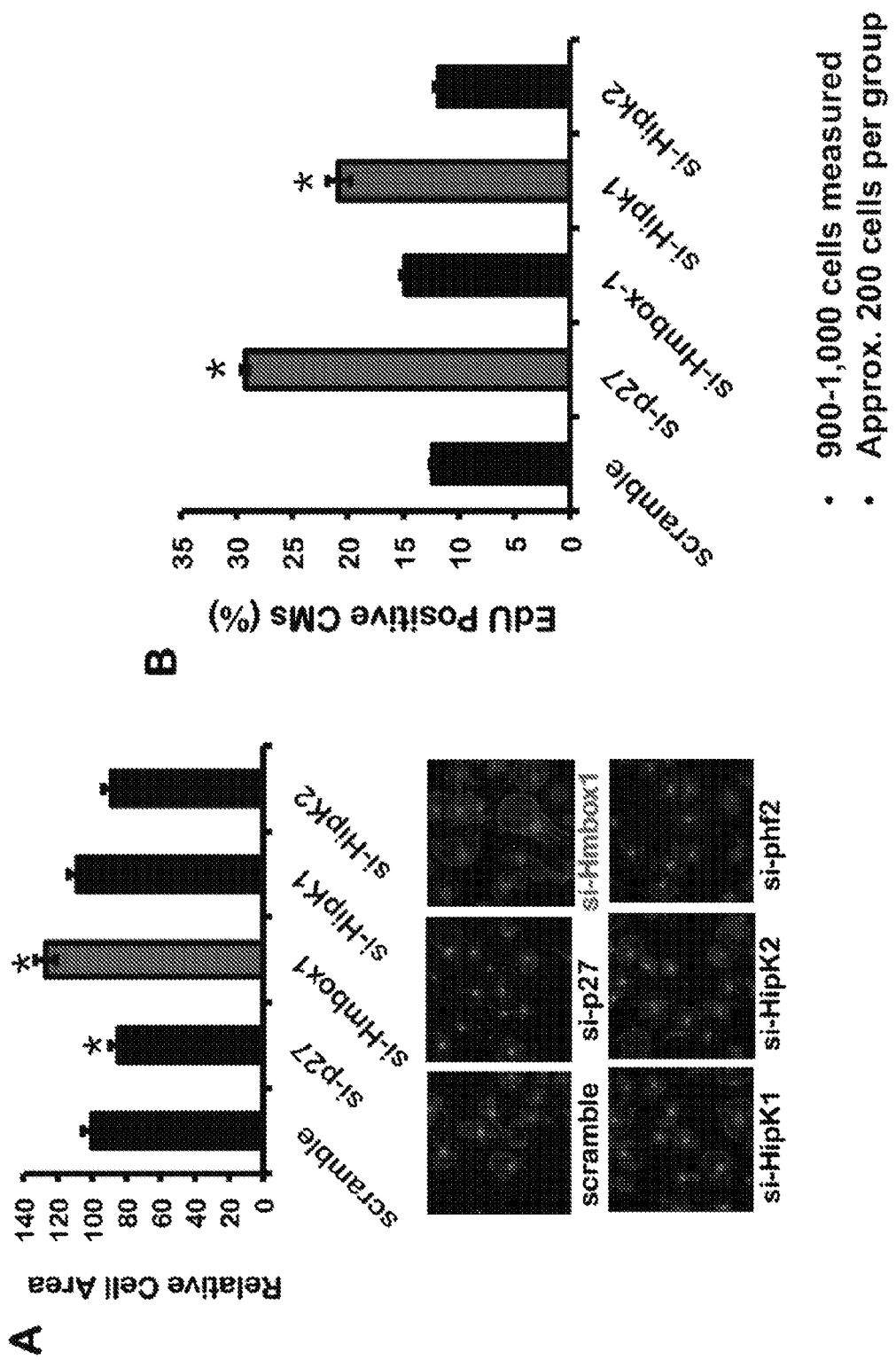
FIG. 8 suggests distinct effects of miR-222 targets in vitro. siRNA knockdown of Homeobox-1 is sufficient to induce cardiomyocytes growth in size (but not proliferation), while knockdown of p27 and HIPK1 are sufficient to drive proliferation of cardiomyocytes in vitro (but not size increase).

Importantly, these targets have distinct contributions to the phenotypic effects of miR-222, as shown in FIGS. 8A-8B.

Figure 14C:
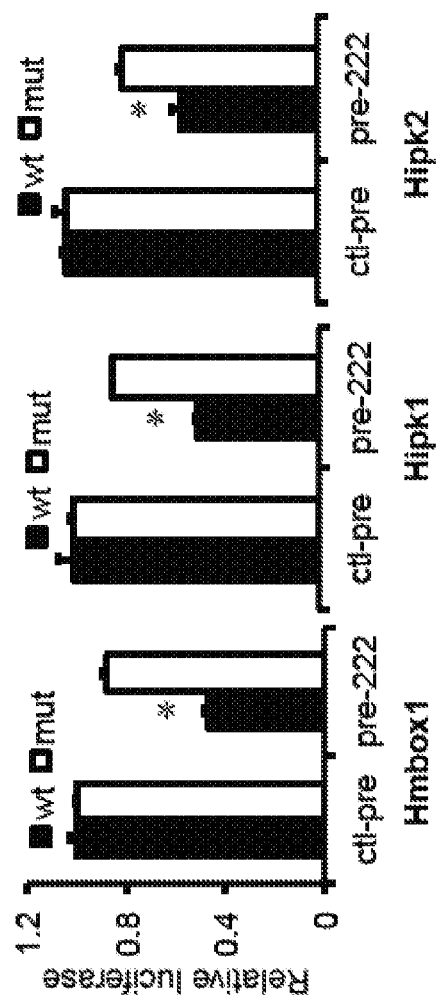

To determine whether and which of these targets contribute to the functional phenotypes seen with miR-222 expression in cardiomyocytes, Applicant used siRNA knockdown for each target (FIG. 14C) and examined their effects on cardiomyocytes. siRNA knockdown of either p27 or HIPK1 was sufficient to induce an increase in EdU incorporation in cardiomyocytes (FIG. 14D) as well as an increase in cardiomyocyte cell number (FIG. 14E). Homeobox-1 knockdown did not affect cell number but caused an increase in cell size (FIG. 14F). Interestingly, p27 knockdown actually caused a decrease in cell size, perhaps reflecting active cell division; HIPK2 had no significant effect in either assay. These data imply that reductions in p27 and HIPK1 are sufficient to induce the proliferative effects of miR-222 in cultured cardiomyocytes, while reduced Homeobox-1 likely contributes to the observed cellular hypertrophy.

These data suggest that forced expression of miR-222 down-regulates at least four target genes, the collective effects of which are associated with the beneficial effects of miR-222 over-expression. On the other hand, approaches relying on individual siRNAs targeting one but not the other miR-222 target genes may not be able to recapitulate the full, beneficial effects of miR-222 expression in vivo.

Example 9 miR-222 Increases after Exercise in Heart Failure Patients

Since miR-222 has been reported to increase in the plasma of healthy young athletes response to exercise, and exercise has beneficial effects in heart failure patients, Applicant sought to determine whether these observations could be related. As an initial step, changes in circulating miR-222 in twenty-eight heart failure patients were examined after acute cardiopulmonary exercise using a bicycle ergometer. Baseline patient characteristics are shown in Table 1, and included patients with stable chronic heart failure (NYHA Class II-IV) with both preserved and reduced systolic function. Exercise duration ranged from 2.5 to 11 minutes on a standardized protocol (Myers, *International journal of sports medicine* 26 Suppl 1: S49-55, 2005). Interestingly, plasma miR-222 increased 1.7-fold (p=0.01) after exercise (FIG. 15); a similar pattern to that seen in young athletes.

TABLE 1

| Patient Information | | |
|---|---|---|
| | Heart failure with reduced EF (HFrEF) (EF < 55%) | Heart failure with preserved EF (HFpEF) (EF ≥ 55%) |
| Number | 19 | 9 |
| Sex | Male | Male |
| Age (year) | 57 ± 10 | 64 ± 16 |
| BMI | 26 ± 2.5 | 24 ± 2.3 |
| EF (%) | 39 ± 6.3 | 65 ± 5.5 |
| NYHA Class | 2.7 ± 0.45 | 2.0 ± 0.0 |

Values are mean ± SD

Example 10 Expression of miRs in Tissues from Mice Injected with AAV9-GFP or AAV9-222

This example demonstrates that miR-222 expression can be increased in vivo in a tissue specific manner using an AAV vector.

Specifically, an AAV-9 based viral expression vector encoding miR-222 (AAV9-miR-222) was injected venously into mice (about $10^{11}$ viral particles in 100 µL). As a negative control, the same vector encoding a GFP reporter was similarly injected to a control mice group. About 5 weeks after the retro-orbital injection, expression of miR-222, and miR-221 as control, were measured in heart and liver of the injected mice.

Figure 16:
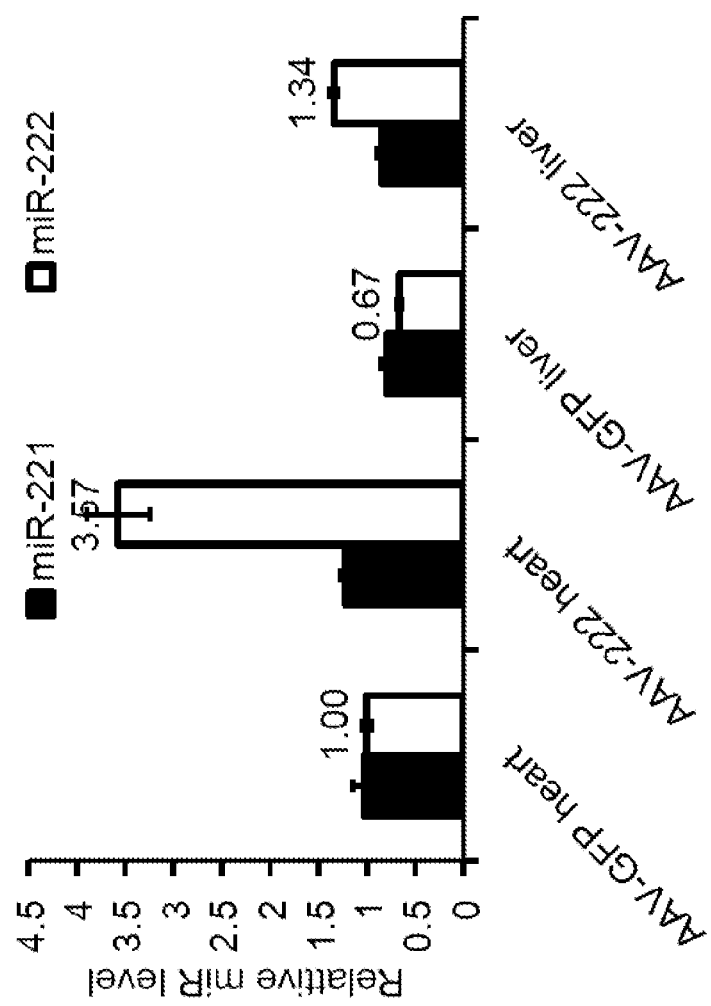
FIG. 16 shows tissue-specific (e.g., heart-specific) expression of miR-222 in vivo using AAV9 vector.

As shown in FIG. 16, mice injected by the AAV9-GFP reporter had no discernible difference in miR-221 and miR-222 expression, either in the heart or in the liver. In contrast, mice injected by the AAV9-miR222 construct had dramatic increase of miR-222 expression in the heart, while the heart expression level of miR-221 was essentially the same as that in the AAV9-GFP mice.

A slight miR-222 expression increase was also observed in the liver of mice injected by the AAV9-miR222 construct, although it is unclear if the increase is statistically significant. Again, the liver expression level of miR-221 was essentially the same as that in the AAV9-GFP mice.

The above data suggests that specific viral vectors (such as AAV9) can be used to deliver and express miR-222 or other nucleic acid of the invention in a specific tissue (e.g., heart).

The following experimental procedures may be used in carrying out one or more of the examples above. The procedures are for illustration purpose only and are not limiting. One of skill in the art can readily envision variations of the same without deviating from the spirit of the invention.

Materials

TAQMAN® Rodent miRNA microarray cards and assays, TAQMAN® MicroRNA Reverse Transcription Kit, TAQMAN® Universal Master Mix II, no UNG, AMBION® PRE-MIR™ miRNA Precursors, SIPORT™ NEOFX™ Transfection Agent, OPTI-MEM® I Reduced Serum Media, High-Capacity cDNA Reverse Transcription Kit, Power SYBR® Green PCR Master Mix, Alexa Fluo (488 and 594) conjugated antibodies, CLICK-IT® EdU ALEXA FLUOR® 488 Imaging Kits, PROLONG® Gold Antifade Reagent with DAPI were purchased from Life technologies. Antibodies against Ki-67, TNNT2, P27, GAPDG, and nonimmune IgG were from Abcam. Antibodies to α-actinin and HMBOX-1 were from Sigma and Bioworld. HRP-conjugated secondary antibodies were from Jackson ImmunoResearch Laboratories. In vivo LNA™ microRNA inhibitors were purchased from Exiqon, and MICRON™ miRNA agomir was obtained from Ribobio.

Primary Rat Neonatal Cardiomyocyte Culture and Transfections

Primary neonatal rat ventricular cardiomyocytes were prepared as described (Matsui et al., 2001). DMEM medium was used for experiments except DMEM/F12 for cultured cell size experiments. siRNAs for p27(kip1), Hmbox1, Hipk1, and Hipk2 and negative controls were purchased from Invitrogen. microRNA precursors (PRE-MIR™ miRNA Precursors) and negative controls were ordered from Invitrogen. Transfection of siRNAs (20 μM), LNA-modified antimiR oligonucleotides (20 μM), or microRNA precursors (0.4 μM) were carried out using Lipofectamine RNAiMAX (Invitrogen) as recommended by the manufacturer. Unless otherwise indicated, a multiplicity of infection (MOI) of 20 was used for adenoviral transfection.

RNA Isolation, Quantitative Real Time PCR (qRT-PCR) and Microarray

Methods used were as described before (Liu et al., 2009). Briefly, RNA from cultured cells and tissues was isolated Tryzol (Invitrogen) following the manufacturers' instructions. qRT-PCR for microRNA was performed on cDNA generated from 100 ng of total RNA using the TaqMan microRNA protocol (Invitrogen). qRT-PCR for mRNA was performed on cDNA generated from 200 ng of total RNA using the high capacity cDNA reverse transcription kit protocol (Invitrogen). Amplification and detection of specific products were performed on a Biorad CFX384 qPCR System. U6 or sno202 was used as an internal control for microRNA template normalization and GADPH or U6 was used for mRNA template normalization. Relative gene expression was calculated by comparing cycle times (Ct) for each target PCR as previously described (Liu et al., 2009). Taqman-based miRNA microarray and individual Taqman-based miRNA assays were carried out following standard procedures.

For human plasma microRNA, total RNA was isolated from 400 μL plasma using the mirVana PARIS isolation kit (Ambion, Austin, Tex.) according to the manufacturer's instructions for plasma samples without enrichment for small RNAs. The *Caenorhabditis elegans* miRNA (cel-miR-39) was added at 50 pmol/L as a control after adding equal volumes of denaturing solution. For quantitative miRNA analysis, the Bulge-Loop™ miRNA qPCR Primer Set (RiboBio) was used to detect miR-222 expression by qRT-PCRs with SYBR Green PCR Master Mix (Bio-Rad, Hercules, Calif., USA) using the 7900HT Fast Real-Time PCR System with 10 μL of PCR master mix containing 1 μL of Forward primer, 1 μL of Reverse primer, 5 μL SYBR Green (2×), 2 μL of RT products, and 1 μL of ddH$_2$O. Cycling parameters were as follows: denaturation at 95° C. for 15 s; annealing at 60° C. for 30 s; and elongation at 72° C. for 30 s (40 cycles) with an initial cycle of 95° C. for 3 min. Cel-miR-39, which lacks sequence homology to human miRNAs was used for normalization. qRT-PCR reactions were run in triplicate, and the signal measured in each cycle.

Flow Cytometry

One million NRVMs were plated in a 6 cm BD Primaria tissue culture dish. Twenty-four hours after plating, cells were transfected with 20 μM LNA, 0.4 μM RNA oligo precursor, or 20 μM siRNA, using lipofectamine RNAiMax overnight. Cells were then synchronized in serum-free media for 24 hours and subsequently cultured in low serum media. Forty-eight hours after transfection, cells were labeled with 20 μM EdU for 24 hours. Before harvesting, cells were incubated with 50 μM Mitotracker orange for 45 minutes. Collected cells were stained by using the protocol of Click-iT EdU Flow Cytometry Assay (Invitrogen). Stained cells were analyzed in a 5-laser LSR II machine in BIDMC flow core facility. At least 10,000 events were recorded by flow cytometry in each treatment. Flowjo7.6.1 was used to analyze flow data.

Western Blot, Immunochemistry, and Immunofluorescence Staining

For Western blotting, protein was isolated from cultured NRVMs and hearts, and equal amounts of protein as determined by BCA protein assay kit (Pierce) were subjected to SDS-PAGE. After membrane transfer, immunoblotting was conducted using primary antibodies to p27 (Kip1) (1:1000, Cell Signaling #3698), HIPK1 (1:500, Abcam ab90103), HIPK2 (1:500, Cell Signaling #5091), and HMBOX1 (1:500, Abcam ab101140). HSP90 (1:1000) was used as a loading control.

For immunochemistry and immunofluorescence staining, hearts were snap frozen in OCT in liquid nitrogen and sectioned on short axis at 5 μm. Frozen sections were stained with wheat germ agglutinin to outline only exactly cross-sectional cardiomyocytes. Click-IT EdU 555 Imaging kit was used to reveal EdU incorporation. To visualize fibrosis, Masson's Trichrome staining was performed by BIDMC histology core facility. For staining, sections were fixed in 4% paraformaldehyde (PFA) followed by washing in PBS. Sections were blocked with 3% (w/v) BSA in PBS and then incubated with primary antibodies applied at 1:100 dilution (unless otherwise indicated) for 1 hour at room temperature. Primary antibodies included: cardiac troponin-I (Abcam ab56357), cardiac troponin-T (Abcam ab10214), α-actinin (Sarcomeric, Sigma A7732), Ki67 (Cell Signaling #9129), and phospho-Histone H3 (Cell Signaling, #3377).

Luciferase Assays

A reporter plasmid was constructed by inserting a fragment of the 3'-UTR of Hipk1, Hipk2 or Hmbox1 mRNA containing the putative miR-222 binding site into a firefly luciferase reporter plasmid psiCHECK-2 (Promega). 3'-UTRs with mutated miR-222 binding sites for Hipk1, Hipk2 or Hmbox1 mRNA were generated using the Quikchange Site-directed Mutagenesis kit (Agilent). COS7 cells were co-transfected with the wild-type or mutated reporter constructs (100 ng) and Ambion pre-miR miR-222 precursor or scrambled control (1 μM) using Lipofectamine 2000 (Invitrogen). 48 hours after transfection, cells were lysed, and relative luciferase expression was measured using a SpectraMax M5 plate reader using a dual luciferase reporter system (Promega).

Mouse Swimming and Running Protocols

All animal protocols were approved by the Animal Care and Use Committee of Beth Israel Deaconess Medical Center. For endurance forced exercise training, male C57BL6/J mice swam in water tanks by using a protocol as described (Taniike et al., 2008). In brief, mice began with two 10-minute swimming sessions separated by at least 4 hrs. Sessions were increased by 10 minutes each day until reaching 90 minute sessions, twice a day. The protocol was stopped after 21 days. During swimming, mice were supervised at all times. Twenty-four hours after the last swimming session, exercised mice were sacrificed and tissues were collected.

For running, male C57BL6/J mice aged 10-12 weeks were subjected to voluntary cage wheel exercise as previously described (Bourajjaj et al., 2008). Briefly, mice were individually housed in a cage equipped with an 11.5-cm-diameter running wheel with a 5.0-cm-wide running surface equipped with a digital magnetic counter activated by wheel rotation. Daily values of exercise time and running distance were recorded for each exercised animal throughout the exercise period. After three weeks of exercise, mice were sacrificed and tissues harvested.

Generation of Tg-miR-222 Mice

A tetracycline-off binary α-MHC transgene system was used as previously described (Sanbe et al., 2003). For the responder mouse line, a 388 bp fragment containing mmu-miR-222 was amplified from mouse genomic DNA and confirmed by sequencing. The fragment was then cloned into a vector, and a large fragment released by digestion with Not I was microinjected into FVB oocytes and transferred to pseudopregnant mice. Cardiac-specific, doxycycline-regulated miR-222 expression was confirmed in line 12, which was used for all the experiments presented. To suppress miR-222 expression, doxycycline was administered in the food using a special diet formulated by Purina (625 mg/kg in pellets). To induce miR-222 expression, mice at 10 to 12 weeks old were fed normal chow (without doxycycline for 4 weeks).

LNA-antimiR Injections

LNA-antimiR injections were performed as described (Grueter et al., 2012). Briefly, 12-week-old C57Bl6 male mice were injected subcutaneously or via tail vein with 10 mg/kg of locked nucleic acid (LNA)-modified antimiR-222 (LNA-antimiR-222) or scrambled control (LNA-SC) reconstituted in saline. Both LNA-antimiR oligonucleotides were purchased from Exiqon. The sequence of LNA-antimiR-222 is +g*t*+a*+g*c*+c*a*+g*+a*t*+g*+t*a*g*+c, in which the "+" and "*" signs indicated an LNA residue and the modified phosphorothioate linkages respectively. The mice were injected for 3 consecutive days and then given a weekly maintenance injection throughout the experiments.

Ischemia Reperfusion, EdU Injection and Determination of the AAR and Myocardial Infarct Size (TTC Staining)

Transgenic FVB or C57BL/6 wild type mice were subjected to ischemia-reperfusion as previously described (Matsui et al., 2002). Briefly, left anterior descending artery (LAD) was ligated with 7-0 silk. Five minutes into ischemia, 50 μl of fluorescent microspheres (10 μm FluoSpheres, Molecular Probes) were injected into the LV cavity. Following 30 min LAD occlusion, the LAD ligature was released, and reperfusion was visually confirmed. After the indicated time interval of reperfusion, mice were sacrificed and tissues collected for analyses. The area-at-risk and myocardial infarct size 24 hours after reperfusion were determined by fluorescent microscopy (for FluoSpheres) and staining with 2,3,5-triphenyltetrazolium chloride (TTC) respectively, as reported previously (Matsui et al., 2002). In some animals EdU (50 mg/kg) was administered subcutaneously every other day for two weeks to identify new DNA synthesis. Sham-operated mice served as controls. All surgeries and analyses were performed by investigators blinded to treatment group and/or genotype.

Microscopy, Confocal Microscopy and Image Quantification

Images of cultured cells were taken in a Leica DM 5000 B microscope. Heart sections were imaged in a Zeiss LSM 501 Meta confocal microscope using standard procedure. All imaging was performed and analyzed by investigators blinded to treatment group. At least 30 random images were obtained from each group. Images were then were quantified using ImageJ and CellProfiler software.

Echocardiography

Echocardiography was performed on conscious mice by using a GE Vivid7 with i13L probe (14 MHZ) as described previously (Das et al., 2012). Briefly, parasternal long-axis views, short-axis views and 2-D guided M-mode images of short axis at the papillary muscle level were recorded. Echocardiography data were analyzed by investigators blinded to treatment group and genotype. The average of at least three measurements was used for every data point from each mouse.

Heart Failure Patients

All human investigation conformed to the principles outlined in the Declaration of Helsinki, and was approved by the relevant institutional review committees. All participants gave written informed consent before enrollment in the study. Twenty-eight patients with chronic stable heart failure underwent a symptom-limited incremental cardiopulmonary exercise test on a bicycle ergometer (GE, USA) using a standardized exercise protocol of revised Ramp10 programs (Myers, 2005). Venous blood was collected in EDTA-K2 tubes before and after the cardiopulmonary exercise test and was processed within 1 hour of collection. After a two-step centrifugation (820×g for 10 min and 16000×g for 10 min, both at 4° C.), the supernatant was transferred to RNase/DNase-free tubes and stored at −80° C. until RNA isolation and PCR were performed as described below.

Statistical Analysis

Data are presented as mean±standard error unless otherwise indicated. Unpaired, two-sided Students t-test was used when indicated with p<0.05 considered statistical significant. When assessing multiple groups, One-Way ANOVA was utilized with turkeys Post Hoc test. The statistical software used was SPSS 17.1.

The invention claimed is:

1. A method of promoting physiological cardiomyocyte growth or proliferation in vivo, the method comprising administering to an adult subject in need thereof a viral vector encoding a CITED4 (CBP/p300-Interacting Transactivator with ED-rich carboxy-terminal Domain 4) polypeptide or fusion protein thereof under the transcriptional control of a promoter,
    wherein the promoter is a cardiac-specific promoter, a muscle-specific promoter, a CMV immediate early gene promoter, an SV40 early promoter, a Rous sarcoma virus long terminal repeat, a rat insulin promoter, or a glyceraldehyde-3-phosphate dehydrogenase promoter;
    wherein the viral vector is an adenoviral vector or an adeno-associated viral (AAV) vector; and,
    wherein the viral vector is administered to the adult subject intravenously or by direct injection into cardiac tissue.

2. A method of treating a heart disease treatable by cardiomyocyte regeneration and/or proliferation, the method comprising administering to an adult subject in need thereof a viral vector encoding a CITED4 (CBP/p300-Interacting Transactivator with ED-rich carboxy-terminal Domain 4) polypeptide or fusion protein thereof under the transcriptional control of a promoter, wherein the promoter is a cardiac-specific promoter, a muscle-specific promoter, a CMV immediate early gene promoter, an SV40 early promoter, a Rous sarcoma virus long terminal repeat, a rat insulin promoter, or a glyceraldehyde-3-phosphate dehydrogenase promoter;

wherein the viral vector is an adenoviral vector or an adeno-associated viral (AAV) vector; and, wherein the viral vector is administered to the adult subject intravenously or by direct injection into cardiac tissue.

3. The method of claim 1, wherein expression or activity of the CITED4 polypeptide or fusion protein thereof is increased in a cardiomyocyte or a precursor thereof in the adult subject.

4. The method of claim 1, wherein the AAV vector is AAV1, AAV2, or AAV9.

5. The method of claim 2, wherein the AAV vector is AAV1, AAV2, or AAV9.

6. The method of claim 2, wherein expression or activity of the CITED4 polypeptide or fusion protein thereof is increased in a cardiomyocyte or a precursor thereof in the adult subject.

7. The method of claim 2, wherein the heart disease is myocardial infarction or ischemic injury; adverse remodeling after ischemic injury or infarction; myocarditis; heart failure, cardiomyopathy; or valvular heart disease.

8. The method of claim 2, wherein therapeutic efficacy is achieved by alleviating at least one symptom of the heart disease, or by inhibiting or retarding the worsening of the symptom.

9. The method of claim 8, wherein therapeutic efficacy is measured by a decrease in a symptom of heart failure, an augment in functional status, a decrease in natriuretic peptide level, and/or beneficial reverse left ventricular (LV) remodeling.

10. The method of claim 1, further comprising administering to the subject a second cardiac therapy.

11. The method of claim 10, wherein said second cardiac therapy is selected from the group consisting of a β blocker, an ionotrope, a diuretic, ACE-I, AII antagonist, BNP, a $Ca^{2+}$-blocker, an endothelin receptor antagonist, and an HDAC inhibitor.

12. The method of claim 2, wherein the heart disease is myocardial infarction, and wherein fibrosis and/or apoptosis in the infarct zone is reduced.

13. The method of claim 2, further comprising administering to the subject a second cardiac therapy.

14. The method of claim 13, wherein said second cardiac therapy is selected from the group consisting of a β blocker, an ionotrope, a diuretic, ACE-I, AII antagonist, BNP, a $Ca^{2+}$-blocker, an endothelin receptor antagonist, and an HDAC inhibitor.

15. The method of claim 1, wherein said adult subject is a human.

16. The method of claim 2, wherein said adult subject is a human.

17. The method of claim 1, wherein said viral vector is said AAV vector, and wherein said AAV vector is delivered to the adult subject via intracoronary infusion.

18. The method of claim 2, wherein said viral vector is said AAV vector, and wherein said AAV vector is delivered to the adult subject via intracoronary infusion.

19. The method of claim 10, wherein said second cardiac therapy is an antiarrhythmic agent, a sodium channel blocker, an antihypertensive agent, an anti-angiotensin II agent, a sympatholytic, a cardiovasculator therapeutic agent, an agent for the treatment of congestive heart failure, an antianginal agent, a surgery, or a combination thereof.

20. The method of claim 13, wherein said second cardiac therapy is an antiarrhythmic agent, a sodium channel blocker, an antihypertensive agent, an anti-angiotensin II agent, a sympatholytic, a cardiovasculator therapeutic agent, an agent for the treatment of congestive heart failure, an antianginal agent, a surgery, or a combination thereof.

\* \* \* \* \*